United States Patent
Wagner et al.

(10) Patent No.: US 11,918,604 B2
(45) Date of Patent: *Mar. 5, 2024

(54) CHIMERIC ANTIGEN RECEPTOR DENDRITIC CELL (CAR-DC) FOR TREATMENT OF CANCER

(71) Applicant: Myeloid Therapeutics, Inc., Cambridge, MA (US)

(72) Inventors: Samuel C. Wagner, San Diego, CA (US); Thomas E. Ichim, San Francisco, CA (US); Julia S. Szymanski, San Diego, CA (US); Santosh Kesari, San Diego, CA (US); Amit N. Patel, Salt Lake City, UT (US); Boris Minev, San Diego, CA (US)

(73) Assignee: MYELOID THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/715,710

(22) Filed: Apr. 7, 2022

(65) Prior Publication Data

US 2022/0233586 A1 Jul. 28, 2022

Related U.S. Application Data

(63) Continuation of application No. 17/559,967, filed on Dec. 22, 2021, which is a continuation of application No. 17/227,193, filed on Apr. 9, 2021, now abandoned, which is a continuation of application No. 15/048,922, filed on Feb. 19, 2016, now abandoned.

(60) Provisional application No. 62/118,027, filed on Feb. 19, 2015.

(51) Int. Cl.
| | | |
|---|---|---|
| *C12N 5/0786* | (2010.01) | |
| *A61K 35/15* | (2015.01) | |
| *A61K 38/17* | (2006.01) | |
| *C07K 16/00* | (2006.01) | |
| *C07K 16/30* | (2006.01) | |
| *C07K 16/32* | (2006.01) | |

(52) U.S. Cl.
CPC ............ *A61K 35/15* (2013.01); *A61K 38/177* (2013.01); *C07K 16/00* (2013.01); *C07K 16/30* (2013.01); *C07K 16/32* (2013.01); *C12N 5/0645* (2013.01); *C07K 2317/622* (2013.01); *C07K 2319/03* (2013.01); *C07K 2319/33* (2013.01); *C12N 2501/599* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,633,234 A | 5/1997 | August et al. |
| 5,773,244 A | 6/1998 | Ares, Jr. et al. |
| 5,776,910 A | 7/1998 | Schreiber et al. |
| 6,210,963 B1 | 4/2001 | Haddada et al. |
| 7,833,789 B2 | 11/2010 | Naldini et al. |
| 7,926,300 B2 | 4/2011 | Roberts et al. |
| 8,198,020 B2 | 6/2012 | Francois et al. |
| 8,709,412 B2 | 4/2014 | Jones et al. |
| 9,045,541 B2 | 6/2015 | Eckelman et al. |
| 9,149,519 B2 | 10/2015 | Landau et al. |
| 9,221,908 B2 | 12/2015 | Frazier et al. |
| 9,428,569 B2 | 8/2016 | Spencer et al. |
| 9,518,116 B2 | 12/2016 | Frazier et al. |
| 9,663,575 B2 | 5/2017 | Eckelman et al. |
| 9,745,368 B2 | 8/2017 | Milone et al. |
| 9,820,350 B2 | 11/2017 | Pyshos et al. |
| 9,845,345 B2 | 12/2017 | Ring et al. |
| 9,913,920 B2 | 3/2018 | Movahedi et al. |
| 10,034,900 B2 | 7/2018 | Senju |
| 10,081,680 B2 | 9/2018 | Weiskopf et al. |
| 10,106,609 B2 | 10/2018 | Yang et al. |
| 10,155,038 B2 | 12/2018 | Rabinovich et al. |
| 10,259,859 B2 | 4/2019 | Pons et al. |
| 10,259,873 B2 | 4/2019 | Frazier et al. |
| 10,299,335 B2 | 5/2019 | Pyshos et al. |
| 10,415,017 B2 | 9/2019 | O'Neill |

(Continued)

FOREIGN PATENT DOCUMENTS

| | | |
|---|---|---|
| CA | 2850380 C | 8/2015 |
| EP | 2626415 A2 | 8/2013 |

(Continued)

OTHER PUBLICATIONS

Scherberich, J. et al., Clin Chem Lab Med, 1999, vol. 37: pp. 209-213.*

(Continued)

*Primary Examiner* — Michael D Burkhart
(74) *Attorney, Agent, or Firm* — Wilson Sonsini Goodrich & Rosati

(57) ABSTRACT

The current invention provides monocytic cells transfected with chimeric antigen receptor (CAR) to selectively home to tumors and upon homing differentiate into dendritic cells capable of activating immunity which is inhibitory to said tumor. In one embodiment of the invention, monocytic cells are transfected with a construct encoding an antigen binding domain, a transcellular or structural domain, and an intracellular signaling domain. In one specific aspect of the invention, the antigen binding domain interacts with sufficient affinity to a tumor antigen, capable of triggering said intracellular domain to induce an activation signal to induce monocyte differentiation into DC.

25 Claims, No Drawings
Specification includes a Sequence Listing.

(56) References Cited

U.S. PATENT DOCUMENTS

| | | |
|---|---|---|
| 10,428,143 B2 | 10/2019 | Krummel et al. |
| 10,602,584 B2 | 3/2020 | Pyshos et al. |
| 10,774,125 B2 | 9/2020 | Ring et al. |
| 10,980,836 B1 | 4/2021 | Getts et al. |
| 11,034,749 B2 | 6/2021 | Gill et al. |
| 2004/0053873 A1 | 3/2004 | Barman et al. |
| 2005/0031628 A1 | 2/2005 | George et al. |
| 2006/0018889 A1 | 1/2006 | Li et al. |
| 2006/0188891 A1 | 8/2006 | Bickmore et al. |
| 2008/0254027 A1 | 10/2008 | Bernett et al. |
| 2011/0250203 A1 | 10/2011 | Klitgaard et al. |
| 2011/0287038 A1 | 11/2011 | Slawin et al. |
| 2011/0293603 A1 | 12/2011 | Saraiva et al. |
| 2012/0045389 A1 | 2/2012 | Gassull Duro et al. |
| 2013/0280285 A1 | 10/2013 | Schonfeld et al. |
| 2014/0134142 A1 | 5/2014 | Smith et al. |
| 2014/0140989 A1 | 5/2014 | Eckelman et al. |
| 2014/0161805 A1 | 6/2014 | Jamieson et al. |
| 2014/0242701 A1 | 8/2014 | Shiku et al. |
| 2015/0057161 A1 | 2/2015 | Schultze et al. |
| 2015/0274826 A1 | 10/2015 | Frazier et al. |
| 2016/0045551 A1* | 2/2016 | Brentjens ............ A61K 35/12 435/328 |
| 2016/0137733 A1 | 5/2016 | Frazier et al. |
| 2016/0145348 A1 | 5/2016 | Stephan |
| 2016/0250258 A1 | 9/2016 | Delaney et al. |
| 2016/0251435 A1 | 9/2016 | Eckelman et al. |
| 2017/0087185 A1 | 3/2017 | Crane et al. |
| 2017/0151281 A1 | 6/2017 | Wagner et al. |
| 2017/0151282 A1 | 6/2017 | Discher et al. |
| 2017/0166657 A1 | 6/2017 | O'Neill et al. |
| 2017/0226183 A1 | 8/2017 | Schiffer-Mannioui |
| 2017/0233452 A1 | 8/2017 | McIvor et al. |
| 2017/0246278 A1 | 8/2017 | Vera Valdes et al. |
| 2017/0283498 A1 | 10/2017 | Frazier et al. |
| 2017/0292118 A1 | 10/2017 | Duchateau et al. |
| 2018/0000899 A1 | 1/2018 | Francois et al. |
| 2018/0030553 A1 | 2/2018 | Tang et al. |
| 2018/0057592 A1 | 3/2018 | Frazier et al. |
| 2018/0104308 A1 | 4/2018 | Mamonkin et al. |
| 2018/0105600 A1 | 4/2018 | Pons et al. |
| 2018/0133252 A9 | 5/2018 | Wilson et al. |
| 2018/0142019 A1 | 5/2018 | Manning et al. |
| 2018/0155405 A1 | 6/2018 | Ring et al. |
| 2018/0171021 A1 | 6/2018 | Karlsson et al. |
| 2018/0186878 A1 | 7/2018 | Rosenthal |
| 2018/0221503 A1 | 8/2018 | Kadiyala et al. |
| 2018/0244748 A1 | 8/2018 | Gill et al. |
| 2018/0250395 A1 | 9/2018 | Pietsch et al. |
| 2018/0319883 A1 | 11/2018 | Weiskopf et al. |
| 2018/0325953 A1 | 11/2018 | Poznansky et al. |
| 2018/0334653 A1 | 11/2018 | O'Neill |
| 2018/0355011 A1 | 12/2018 | Lim et al. |
| 2019/0008897 A1 | 1/2019 | Scatena et al. |
| 2019/0010219 A1 | 1/2019 | Short |
| 2019/0023761 A1 | 1/2019 | Pule et al. |
| 2019/0038671 A1 | 2/2019 | Fan et al. |
| 2019/0062450 A1 | 2/2019 | De Palma et al. |
| 2019/0070277 A1 | 3/2019 | O'Neill et al. |
| 2019/0112373 A1 | 4/2019 | Manning et al. |
| 2019/0119379 A1 | 4/2019 | Gottschalk et al. |
| 2019/0119396 A1 | 4/2019 | Liu et al. |
| 2019/0144522 A1 | 5/2019 | Bari et al. |
| 2019/0169266 A1 | 6/2019 | Pons et al. |
| 2019/0233496 A1 | 8/2019 | Rosenthal |
| 2019/0240343 A1 | 8/2019 | Ahmed et al. |
| 2019/0248892 A1 | 8/2019 | Frazier et al. |
| 2019/0263928 A1 | 8/2019 | Watanabe et al. |
| 2019/0275150 A1 | 9/2019 | Pincetic et al. |
| 2019/0336615 A1 | 11/2019 | Thompson et al. |
| 2019/0345217 A1 | 11/2019 | Ma et al. |
| 2019/0381158 A1 | 12/2019 | Gunn |
| 2020/0247870 A1 | 8/2020 | Gill et al. |
| 2020/0345773 A1 | 11/2020 | Getts et al. |
| 2020/0345774 A1 | 11/2020 | Getts et al. |
| 2021/0002377 A1 | 1/2021 | Brogdon et al. |
| 2021/0046110 A1 | 2/2021 | Gill et al. |
| 2021/0095001 A1 | 4/2021 | Gill et al. |
| 2021/0252053 A1 | 8/2021 | Wagner et al. |
| 2022/0000917 A1 | 1/2022 | Klichinsky et al. |
| 2022/0000918 A1 | 1/2022 | Klichinsky et al. |
| 2022/0002375 A1 | 1/2022 | Gill et al. |
| 2022/0002376 A1 | 1/2022 | Gill et al. |
| 2022/0002377 A1 | 1/2022 | Gill et al. |
| 2022/0002675 A1 | 1/2022 | Klichinsky et al. |
| 2022/0033465 A1 | 2/2022 | Gill et al. |
| 2022/0033466 A1 | 2/2022 | Gill et al. |
| 2022/0033467 A1 | 2/2022 | Gill et al. |
| 2022/0033468 A1 | 2/2022 | Gill et al. |
| 2022/0041688 A1 | 2/2022 | Gill et al. |
| 2022/0073639 A1 | 3/2022 | Ruella et al. |
| 2022/0098273 A1 | 3/2022 | Corey |

FOREIGN PATENT DOCUMENTS

| | | |
|---|---|---|
| EP | 2953643 A1 | 12/2015 |
| EP | 2242512 B1 | 4/2016 |
| EP | 3197495 A1 | 8/2017 |
| EP | 3328402 A1 | 6/2018 |
| EP | 2956343 B1 | 12/2018 |
| EP | 3504244 A1 | 7/2019 |
| EP | 3519441 A1 | 8/2019 |
| EP | 3574018 A4 | 10/2020 |
| GB | 2572005 A | 9/2019 |
| WO | WO-1995005835 A1 | 3/1995 |
| WO | WO-02077029 A2 | 10/2002 |
| WO | WO-02077029 A3 | 5/2003 |
| WO | WO-2004050855 A2 | 6/2004 |
| WO | WO-2007113572 A1 | 10/2007 |
| WO | WO-2008011599 A2 | 1/2008 |
| WO | WO-2011028554 A1 | 3/2011 |
| WO | WO-2012005763 A1 | 1/2012 |
| WO | WO-2012045389 A1 | 4/2012 |
| WO | WO-2013123088 A1 | 8/2013 |
| WO | WO-2013185552 A1 | 12/2013 |
| WO | WO-2014055668 A1 | 4/2014 |
| WO | WO-2014123580 A1 | 8/2014 |
| WO | WO-2014153114 A1 | 9/2014 |
| WO | WO-2016033331 A1 | 3/2016 |
| WO | WO-2016040441 A1 | 3/2016 |
| WO | WO-2016070136 A1 | 5/2016 |
| WO | WO-2016126608 A1 | 8/2016 |
| WO | WO-2016149254 A1 | 9/2016 |
| WO | WO-2016172606 A1 | 10/2016 |
| WO | WO-2017025944 A2 | 2/2017 |
| WO | WO-2017044487 A1 | 3/2017 |
| WO | WO-2017050884 A1 | 3/2017 |
| WO | WO-2017025944 A3 | 4/2017 |
| WO | WO-2017136633 A1 | 8/2017 |
| WO | WO-2018038684 A1 | 3/2018 |
| WO | WO-2018064076 A1 | 4/2018 |
| WO | WO-2018140831 A3 | 8/2018 |
| WO | WO-2018169948 A1 | 9/2018 |
| WO | WO-2018231871 A1 | 12/2018 |
| WO | WO-2019005641 A1 | 1/2019 |
| WO | WO-2019032624 A1 | 2/2019 |
| WO | WO-2019067328 A1 | 4/2019 |
| WO | WO-2019070704 A1 | 4/2019 |
| WO | WO-2019086512 A1 | 5/2019 |
| WO | WO-2019129146 A1 | 7/2019 |
| WO | WO-2019191332 A1 | 10/2019 |
| WO | WO-2019191334 A1 | 10/2019 |
| WO | WO-2019191340 A1 | 10/2019 |
| WO | WO-2020095044 A1 | 5/2020 |
| WO | WO-2020097193 A1 | 5/2020 |
| WO | WO-2020223550 A1 | 11/2020 |
| WO | WO-2021263152 A1 | 12/2021 |

(56) References Cited

FOREIGN PATENT DOCUMENTS

| WO | WO-2022036265 A1 | 2/2022 |
|---|---|---|
| WO | WO-2022067033 A1 | 3/2022 |

OTHER PUBLICATIONS

Schroers, R. et al., Mol. Ther., 1999, vol. 1: pp. 171-179.*
Yong, C. et al., Open Gene Ther J., 2013, vol. 5: pp. 1-11.*
Villanueva, M., Nature, 2020, p. 308.*
Levine et al., Mol Ther. Methods Clin Dev., 2017: pp. 92-101.*
Ali, M. et al., "Induction of neoantigen-reactive T cells from healthy donors", Nature Protocols (2019).
Alvey C, Discher DE. 2017. Engineering macrophages to eat Cancer: from "marker of self" CD47 and phagocytosis to differentiation. Journal of Leukocyte Biology 102:31-40.
Alvey CM, Spinler KR, Irianto J, Pfeifer CR, Hayes B, Xia Y, Cho S, Dingal P, Hsu J, Smith L, Tewari M, Discher DE. 2017. SIRPA-Inhibited, Marrow-Derived macrophages engorge, accumulate, and differentiate in Antibody-Targeted regression of solid tumors. Current Biology 27:2065-2077.
Ancuta et al. (BMC Genomics 2009 10:403, pp. 1-19).
Andreesen R, Scheibenbogen C, Brugger W, Krause S, Meerpohl HG, Leser HG, Engler H, Lo hr GW. 1990. Adoptive transfer of tumor cytotoxic macrophages generated in vitro from circulating blood monocytes: a new approach to Cancer immunotherapy. Cancer Research 50:7450-7456.
Andreu N, Phelan J, de Sessions PF, Cliff JM, Clark TG, Hibberd ML. 2017. Primary macrophages and J774 cells respond differently to infection with Mycobacterium tuberculosis. Scientific Reports 7:42225.
"Application as filed for U.S. Appl. No. 17/202,018, filed Mar. 15, 2021".
Auffray et al. Blood monocytes: development, heterogeneity, and relationship with dendritic cells, Annual Rev. Immunol. 2009 27:669-92.
Batista FD, Iber D, Neuberger MS. 2001. B cells acquire antigen from target cells after synapse formation. Nature 411:489-494.
Beningo KA, Wang YL. 2002. Fc-receptor-mediated phagocytosis is regulated by mechanical properties of the target. Journal of Cell Science 115:849-856.
Berger, et al., Efficient Elutriation of monocytes within a closed system (Elutra™) Journal of Immunological Methods 298 (2005) 61-72.
Bhattacharjee, J., et al., "Monocytes isolated by positive and negative magnetic sorting techniques show different molecular characteristics and immunophenotypic behaviour", F100Research (2018) pp. 1-13.
Biglari, A., et al. Human monocytes expressing a CEA-specific chimeric CD64 receptor specifically target CEA-expressing tumour cells in vitro and in vivo, Gene Therapy (2006) 13, 602-610.
"Bournazos, S., The Role and Function of Fcγ Receptors on Myeloid Cells Microbiol Spectr. Dec. 2016 ; 4(6):1-29."
Brooks SR, Kirkham PM, Freeberg L, Carter RH. 2004. Binding of cytoplasmic proteins to the CD19 intracellular domain is high affinity, competitive, and multimeric. The Journal of Immunology 172:7556-7564.
Bu JY, Shaw AS, Chan AC. 1995. Analysis of the interaction of ZAP-70 and syk protein-tyrosine kinases with the T-cell antigen receptor by plasmon resonance. PNAS 92:5106-5110.
"Burgueno-Bucio et al. "The multiple faces of CD5" J. Leukoc Bio. (2019) 105:891-904".
Chao MP, Alizadeh AA, Tang C, Myklebust JH, Varghese B, Gill S, Jan M, Cha AC, Chan CK, Tan BT, Park CY, Zhao F, Kohrt HE, Malumbres R, Briones J, Gascoyne RD, Lossos IS, Levy R, Weissman IL, Majeti R. 2010. Anti-CD47 antibody synergizes with rituximab to promote phagocytosis and eradicate non-Hodgkin lymphoma. Cell 142:699-713.
Chen J, Zhong MC, Guo H, Davidson D, Mishel S, Lu Y, Rhee I, Pe' rez-Quintero LA, Zhang S, Cruz-Munoz ME, Wu N, Vinh DC, Sinha M, Calderon V, Lowell CA, Danska JS, Veillette A. 2017. SLAMF7 is critical for phagocytosis of haematopoietic tumour cells via Mac-1 integrin. Nature 544:493-497.
Corresponding PCT Application No. PCT/US2019/060052, filed Nov. 6, 2019.
Cros, et al., "Human CD14dim) Monocytes Patrol and Sense Nucleic Acids and viruses via TLR7 and TLR8 Receptors", Immunity 33, 375-386, Sep. 24, 2010.
Cross SE, Jin YS, Rao J, Gimzewski JK. 2007. Nanomechanical analysis of cells from cancer patients. Nature Nanotechnology 2:780-783.
Davis SJ, van der Merwe PA. 2006. The kinetic-segregation model: TCR triggering and beyond. Nature Immunology 7:803-809.
De Oliveria, S, et al., "Modification of Hematopoietic Stem/Progenitor Cells with CD19-Specific Chimeric Antigen Receptros as a Novel Approach for Cancer Immunotherapy" Human Gene Therapy 24:824-839 (Oct. 2013).
Edelstein A, Amodaj N, Hoover K, Vale R, Stuurman N. 2010. Computer control of microscopes using mmanager. Current Protocols in Molecular Biology 14:Unit14.20.
Engel P, Zhou LJ, Ord DC, Sato S, Koller B, Tedder TF. 1995. Abnormal B lymphocyte development, activation, and differentiation in mice that lack or overexpress the CD19 signal transduction molecule. Immunity 3:39-50.
Fesnak AD, June CH, Levine BL. 2016. Engineered T cells: the promise and challenges of cancer immunotherapy. Nature Reviews Cancer 16:566-581.
Fraser, A., et al, "Development, functional characterization and validation of methodology for GMP-compliant manufacture of phagocytic macrophages: A novel cellular therapeutic for liver cirrhosis", Cyotherapy, 2017, ISSN 1465-3249.
Freeman SA, Goyette J, Furuya W, Woods EC, Bertozzi CR, Bergmeier W, Hinz B, van der Merwe PA, Das R, Grinstein S. 2016. Integrins Form an Expanding Diffusional Barrier that Coordinates Phagocytosis. Cell 164: 128-140.
Freeman SA, Grinstein S. 2014. Phagocytosis: receptors, signal integration, and the cytoskeleton. Immunological Reviews 262:193-215.
Gardai SJ, McPhillips KA, Frasch SC, Janssen WJ, Starefeldt A, Murphy-Ullrich JE, Bratton DL, Oldenborg PA, Michalak M, Henson PM. 2005. Cell-surface calreticulin initiates clearance of viable or apoptotic cells through trans-activation of LRP on the phagocyte. Cell 123:321-334.
"Geissmann, et al., "Blood Monocytes Consist of Two Principal Subsets with Distinct Migratory Properties", Immunity, vol. 19, pp. 71-82, Jul. 2003".
Getts, Daniel R., "Microparticles bearing encephalitogenic peptides induce T-cell tolerance and ameliorate experimental autoimmune encephalomyelitis", Nat Biotechnol. Dec. 2012; 30(12): 1217-1224.
"Gordon, S., Phagocytosis and immunobiological process. Immunity 44, Mar. 15, 2016 p. 463-475."
Goudot, C. et al., "Aryl Hydrocarbon Receptro Controls Monocyte Differentiation into Dendritic Cells versus Macrophages", Sep. 19, 2017 Immunity 47, 582-596.
Harshyne LA, Zimmer MI, Watkins SC, Barratt-Boyes SM. 2003. A Role for Class A Scavenger Receptor in Dendritic Cell Nibbling from Live Cells. The Journal of Immunology 170:2302-2309.
Harshyne LA, Watkins SC, Gambotto A, Barratt-Boyes SM. 2001. Dendritic cells acquire antigens from live cells for Cross-Presentation to CTL. The Journal of Immunology 166:3717-3723.
Haso W, Lee DW, Shah NN, Stetler-Stevenson M, Yuan CM, Pastan IH, Dimitrov DS, Morgan RA, FitzGerald DJ, Barrett DM, Wayne AS, Mackall CL, Orentas RJ. 2013. Anti-CD22-chimeric antigen receptors targeting B-cell precursor acute lymphoblastic leukemia. Blood 121:1165-1174.
Huang, Min-Nung, et al., "Antigen-loaded monocyte administration induces potent therapeutic antitumor T cell responses", The Journal of Clinical Investigation, Jan. 6, 2020, pp. 1-15.
"Hui E., T cell costimulatory receptor CD28 is a primary target for PD-1-mediated inhibition, Science. Mar. 31, 2017; 355(6332): 1428-1433".

(56) References Cited

OTHER PUBLICATIONS

Hui E, Vale RD. 2014. In vitro membrane reconstitution of the T-cell receptor proximal signaling network. Nature Structural & Molecular Biology 21:133-142.
"Sica, F., Fingolimod Immune Effects Beyond Its Sequestration Ability, Neurol Ther (2019) 8:231-240".
"Silverstein RL., Mechanisms of Cell Signaling by the Scavenger Receptor CD36: Implications in Atherosclerosis and Thrombosis, Transactions of the American Clinical and Climatological Association, vol. 121, 2010".
Ingersoll, Ph.D., Brooke, "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160.
International Search Report and Written Opinion for PCT/US2020/030837 dated Oct. 1, 2020.
"International Search Report and Written Opinion for PCT/US2020/064686 dated Apr. 6, 2021".
"International Search Report and Written Opinion in corresponding PCT/US2020/064686 dated Apr. 6, 2021".
Jadus MR, Irwin MC, Irwin MR, Horansky RD, Sekhon S, Pepper KA, Kohn DB, Wepsic HT. 1996. Macrophages can recognize and kill tumor cells bearing the membrane isoform of macrophage colony-stimulating factor. Blood 87:5232-5241.
Jaiswal S, Jamieson CH, Pang WW, Park CY, Chao MP, Majeti R, Traver D, van Rooijen N, Weissman IL. 2009. CD47 is upregulated on circulating hematopoietic stem cells and leukemia cells to avoid phagocytosis. Cell 138:271-285.
James JR, Vale RD. 2012. Biophysical mechanism of T-cell receptor triggering in a reconstituted system. Nature 487:64-69.
Joly E, Hudrisier D. 2003. What is trogocytosis and what is its purpose? Nature Immunology 4:815.
Kao G, Huang CC, Hedgecock EM, Hall DH, Wadsworth WG. 2006. The role of the laminin beta subunit in laminin heterotrimer assembly and basement membrane function and development in C. elegans. Developmental Biology 290:211-219.
Kim, et al., "Monocyte Enrichment from Leukapheresis products by using the Elutra cell separator" Transfusion, vol. 47, Dec. 2007 pp. 2290-2296.
Kochenderfer JN, Feldman SA, Zhao Y, Xu H, Black MA, Morgan RA, Wilson WH, Rosenberg SA. 2009. Construction and preclinical evaluation of an anti-CD19 chimeric antigen receptor. Journal of Immunotherapy 32:689-702.
Lacerna LV, Stevenson GW, Stevenson HC. 1988. Adoptive cancer immunotherapy utilizing lymphokine activated killer cells and gamma interferon activated killer monocytes. Pharmacology & Therapeutics 38:453-465.
"Laird et al. (J. Leukocyte Biology 2009, 85: 966-977)".
Lee S, Kivimae S, Dolor A, Szoka FC. 2016. Macrophage-based cell therapies: the long and winding road. Journal of Controlled Release 240:527-540.
Lim WA, June CH, Huang J, Hodes RJ. 2017. The Principles of Engineering Immune Cells to Treat Cancer. Cell 168:724-740.
Liu X, Pu Y, Cron K, Deng L, Kline J, Frazier WA, Xu H, Peng H, Fu YX, Xu MM. 2015. CD47 blockade triggers T cell-mediated destruction of immunogenic tumors. Nature Medicine 21:1209-1215.
Majeti R, Chao MP, Alizadeh AA, Pang WW, Jaiswal S, Gibbs KD, van Rooijen N, Weissman IL. 2009. CD47 is an adverse prognostic factor and therapeutic antibody target on human acute myeloid leukemia stem cells. Cell 138:286-299.
"Matsuyoshi, Hidetake, et al., "Enchanced Priming of Antigen-Specific CTL's In Vivo by Embryonic Stem Cell-Derived Dendritic Cells Expressing Chemokine Along with Antigenic Protein: Application to Antitumor Vaccination", The Journal of Immunology (2004) 172:776-786".
Mayordomo JI, Zorina T, Storkus WJ, Zitvogel L, Celluzzi C, Falo LD, Melief CJ, Ildstad ST, Kast WM, Deleo AB. 1995. Bone marrow-derived dendritic cells pulsed with synthetic tumour peptides elicit protective and therapeutic antitumour immunity. Nature Medicine 1:1297-1302.
"McEver R, Selectins: initiators of leucocyte adhesion and signalling at the vascular wall, Cardiovascular Research (2015) 107, 331-339".
"Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171".
Morrissey, M., et al., "Chimeric antigen receptros that trigger phagocytosis", eLife 2018, pp. 1/21.
Mukherjee, R. et al., "Non-Classical monocytes display inflammatory features: Validation in Sepsis and Systemic Lupus Erythematous", Scientific Reports, (2015) pp. 1-14.
"Murshid, Ayesha, et al, "Hsp90-peptide complexes stimulate antigen presentation through the class II pathway after binding scavenger receptor SREC-1", Immunobiology, Dec. 2014; 219(12); 924-931".
"Soderberg et al. (J. Virology 1993 67(6): 3166-3175)".
Oviedo-Boyso J., The Phosphoinositide-3-Kinase-Akt Signaling Pathway is Important for *Staphylococcus aureus* Internalization by Endothelial Cells, Infection and Immunity, Nov. 2011, p. 4569-4577.
Passlick, et al., "Identification and Characterization of a Novel Monocyte Subpopulation in Human Peripheral Blood", Article in Blood, Dec. 1989, 74: 2527-2534.
"Patel, A., The fate and lifespan of human monocyte subsets in steady state and systemic inflammation, J. Exp. Med. 2017 vol. 214 No. 7 1913-1923".
PCT/US2019/060052 International Search Report and Written Opinion dated Apr. 30, 2020.
Penberthy KK, Ravichandran KS. 2016. Apoptotic cell recognition receptors and scavenger receptors. Immunological Reviews 269:44-59.
Ralston KS, Solga MD, Mackey-Lawrence NM, Somlata , Bhattacharya A, Petri WA. 2014. Trogocytosis by Entamoeba histolytica contributes to cell killing and tissue invasion. Nature 508:526-530.
Roberts EW, Broz ML, Binnewies M, Headley MB, Nelson AE, Wolf DM, Kaisho T, Bogunovic D, Bhardwaj N, Krummel MF. 2016. Critical Role for CD103(+)/CD141(+) Dendritic Cells Bearing CCR7 for Tumor Antigen Trafficking and Priming of T Cell Immunity in Melanoma. Cancer Cell 30:324-336.
Roberts, Margo R., et al."Antigen-Specific Cytolysis by Neutrophils and NK Cells Expressing Chimeric Immune Receptros Bearing xx Signaling Domains", J Immunol 1998; 161:375-384.
Rosales, C. et al, "Phagocytosis: A Fundamental Process in Immunity", BioMed Research International, vol. 2017, Article ID 9042851, 18 pages.
Ruiz-Aguilar, S., et al., "Human CD16+ and CD16+ monocyte subsets display unique effector properties in inflammatory conditions in vivo", Journal of Leukocyte Biology, (2011) vol. 90, pp. 1119-1131.
Schlam D, Bagshaw RD, Freeman SA, Collins RF, Pawson T, Fairn GD, Grinstein S. 2015. Phosphoinositide 3-kinase enables phagocytosis of large particles by terminating actin assembly through Rac/Cdc42 GTPase—activating proteins. Nature Communications 6:8623.
Schlam, et al., "Phosphoinositide 3-kinase enables phagocytosis of large particles by terminating actin assembly through Rac/Cdc42 GRPase-activating proteins" (2015) Nature Communications.
Senju, Satoru, et al., "Generation and genetic modification of dendritic cells derived from mouse embryonic stem cells derived from mouse embryonics stem cells", BLOOD, May 1, 2003, vol. 101, No. 9, pp. 3501-3508.
Su X, et al., Phase separation of signaling molecules promotes T cell receptor signal transduction, Science. Apr. 29, 2016; 352(6285): 595-599.
"Tippet et al. (J. Leukocyte Biology 2013 93: 913-920)".
"Strauss, O et al., The immunophenotype of antigen presenting cells of the mononuclear phagocyte system in normal human liver—A systematic review. Journal of Hepatology 2015 vol. 62, 458-468."
Tseng D, Volkmer JP, Willingham SB, Contreras-Trujillo H, Fathman JW, Fernhoff NB, Seita J, Inlay MA, Weiskopf K, Miyanishi M,

(56) References Cited

OTHER PUBLICATIONS

Weissman IL. 2013. Anti-CD47 antibody-mediated phagocytosis of cancer by macrophages primes an effective antitumor T-cell response. PNAS 110:11103-11108.
Tsutsui, et al. "The use of microbubbles to target drug delivery" Cardiovascular Ultrasound (2004) 2:23.
Tuveson DA, Carter RH, Soltoff SP, Fearon DT. 1993. CD19 of B cells as a surrogate kinase insert region to bindphosphatidylinositol 3-kinase. Science 260:986-989.
Weischenfeldt J, Porse B. 2008. Bone Marrow-Derived Macrophages (BMM): Isolation and Applications. Cold Spring Harbor Protocols 2008:pdb.prot5080.
"Wilkinson et al. (Med. Microbio. Immunol. 2015 204:273-284)".
Xiao X, Ho M, Zhu Z, Pastan I, Dimitrov DS. 2009. Identification and characterization of fully human anti-CD22 monoclonal antibodies. mAbs 1:297-303.
Yong, C., et al, "A role for multiple chimeric antigen receptor-expressing leukocytes in antigen-specific responses to cancer" (2016) Oncotarget, vol. 7, No. 23 pp. 34582-34598.
Blumenthal D. et al., (Nov. 10-14, 2021). "Development and Characterization of Chimeric Antigen Receptor Monocytes (CAR Mono), a Novel Cell Therapy Platform for Solid Tumor Immunotherapy." Poster Presentation. Society for Immunotherapy of Cancer (SITC) Meeting, Washington, DC, United States. https://secureservercdn.net/45.40.149.113/74d.fcf.myftpupload.com/wp-content/uploads/2021/11/Poster-104-Daniel-Blumenthal-Carisma-Therapeutics.pdf.
Blumenthal D. et al., (Apr. 8-13, 2022). "Pre-clinical development of CAR Monocytes (CAR Mono) for solid tumor immunotherapy." Poster Presentation. The American Association for Cancer Research (AACR) Annual Meeting, New Orleans, LA, United States. https://secureservercdn.net/45.40.149.113/74d.fcf.myftpupload.com/wp-content/uploads/2022/07/Poster-5000-Daniel-Blumenthal-Carisma-Therapeutics.pdf.
Calderwood, David, "Integrin Activation" Journal of Cell Science (2004) 117, pp. 657-666.
Daeron et al. Fc Receptors. Current Topics in Microbiology and Immunology, vol. 382. 2014.
Dotti et al. Design and Development of Therapies using Chimeric Antigen Receptor-Expressing T cells. Immunol Rev. 257(1):35 pgs (2014).
Gabitova L. et al., (Apr. 10-15 and May 17-21, 2021). "Anti-HER2 CAR monocytes demonstrate targeted anti-tumor activity and enable a single day cell manufacturing process." Poster Presentation. The American Association for Cancer Research (AACR) Annual Meeting, Philadelphia, PA, United States. https://secureservercdn.net/45.40.149.113/74d.fcf.myftpupload.com/wp-content/uploads/2021/09/Anti-HER2-CAR-monocytes_AACR2021.pdf.
"Getts, et al., "Microparticles bearing encephalitogenic peptides induce T-cell tolerance and ameliorate experimental autoimmune encephalomyelitis" (2012) Nat Biotechnol. 30(12) pp. 1217-1224".
"Harburger, et al., "Integrin signalling at a glance" (2009) Journal of Cell Sciences 122".
"Silverstein, et al., "Mechanisms of Cell Signaling by The Scavenger Receptor CD36: Implications in Atherosclerosis and Thrombosis" Transactions of the American Clinical and Climatological Association, vol. 121 (2010), vol. 121".
International Search Report and Written Opinion for corresponding PCT/US2020/030837 dated Oct. 1, 2020.
Italiani P, Boraschi D. "From Monocytes to M1/M2 Macrophages: Phenotypical vs. Functional Differentiation." Front Immunol. Oct. 17, 2014;5:514.
Jarrosson-Wuilleme et al.: Transduction of nondividing human macrophages with gammaretrovirus-derived vectors. J Virol. 80(3):1152-1159 doi:10.1128/JVI.80.3.1152-1159.2006 (2006).
Klichinsky M. et al., "CAR-Macrophage for Cancer Immunotherapy: Latest Findings from the CT-0508 Clinical Trial" YouTube, https://youtu.be/2Ag7SVM-fPg, published Jun. 27, 2022, https://carismatx.com/programs/ct-0508/.
Klichinsky M et al., "Human chimeric antigen receptor macrophages for cancer immunotherapy." Nat Biotechnol. Aug. 2020;38(8):947-953. Epub Mar. 23, 2020.
Lloyd et al. Modelling the human immune response: performance of a 1011 human antibody repertoire against a broad panel of therapeutically relevant antigens. Protein Eng Des Sel 22(3):159-168 (2009).
"McEver, et al., "Selectins: initiators of leucocyte adhesion and signalling at the vascular wall" Cardiovascular Research (2015) 107, pp. 331-339".
Murshid, et al., "Hsp90-peptide complexes stimulate antigen presentation through the class II pathway after binding scavenger receptor SREC-I" Immunobiology (2014) 219(12) pp. 924-931.
Olingy CE et al., "Monocyte heterogeneity and functions in cancer." J Leukoc Biol. Aug. 2019;106(2):309-322. doi: 10.1002/JLB.4RI0818-311R. Epub Feb. 18, 2019.
Orecchioni M et al., "Macrophage Polarization: Different Gene Signatures in M1(LPS+) vs. Classically and M2(LPS-) vs. Alternatively Activated Macrophages." Front Immunol. May 24, 2019;10:1084. Erratum in: Front Immunol. Feb. 25, 2020;11:234.
Oshi M, et al., "M1 Macrophage and M1/M2 ratio defined by transcriptomic signatures resemble only part of their conventional clinical characteristics in breast cancer." Sci Rep. Oct. 6, 2020;10(1):16554.
"Oviedo-Boyso, et al., "The Phosphoinositide-3-Kinase-Akt Signaling Pathway is Important for *Staphylococcus aureus* Internalization by Endothelial Cells" (2011) Infection and Immunity, vol. 79, No. 11, p. 4569-4577".
PCT/US2020/037312 International Search Report dated Nov. 30, 2020.
PCT/US2020/049240 International Search Report dated Mar. 26, 2021.
PCT/US2020/064686 International Search Report and Written Opinion dated Apr. 6, 2021.
Pierini S. et al., (Nov. 9-14, 2020). "Chimeric antigen receptor macrophages (CAR-M) elicit a systemic anti-tumor immune response and synergize with PD-1 blockade in immunocompetent mouse models of HER2+ solid tumors." Poster Presentation. Society for Immunotherapy of Cancer (SITC) Meeting, Virtual. https://secureservercdn.net/45.40.149.113/74d.fcf.myftpupload.com/wp-content/uploads/2021/09/CAR-M-syngeneic-model_SITC2020.pdf.
Pierini S. et al., (Apr. 8-13, 2022). "Chimeric antigen receptor macrophages (CAR-M) sensitize solid tumors to anti-PD1 immunotherapy." Poster Presentation. The American Association for Cancer Research (AACR) Annual Meeting, New Orleans, LA, United States. https://secureservercdn.net/45.40.149.113/74d.fcf.myftpupload.com/wp-content/uploads/2022/07/AACR2022_CARMaPD11.pdf.
Reiss K. et al., (Nov. 10-14, 2021). "LBA (951): A Phase 1 first in human study of adenovirally transduced anti-HER2 CAR Macrophages in subjects with HER2 overexpressing solid tumors: preliminary safety, pharmacokinetics, and TME reprogramming data." Poster Presentation. Society for Immunotherapy of Cancer (SITC) Meeting, Washington, DC, United States. https://secureservercdn.net/45.40.149.113/74d.fcf.myftpupload.com/wp-content/uploads/2021/11/Poster-LBA951-CT-0508-Study-101-SITC-FINAL.pdf.
Reiss K. et al., (Jun. 3-7, 2022). "A Phase 1, First-In-Human (FIH) Study of the Anti-HER2 CAR Macrophage CT-0508 in Participants with HER2 Overexpressing Solid Tumors." Poster Presentation. American Society of Clinical Oncology (ASCO) Annual Meeting, New Chicago, IL, United States. https://secureservercdn.net/45.40.149.113/74d.fcf.myftpupload.com/wp-content/uploads/2022/07/ASCO-Data-In-Person-2022.final_.pdf.
Senju, et al., "Generation of dendritic cells and macrophages from human induced pluripotent stem cells aiming at cell therapy" Gene Therapy (2011) 18, 874-883.
Sloas C. et al., (Nov. 10-14, 2021). "SIRPα-Deficient CAR-Macrophages Exhibit Enhanced Anti-Tumor Function and Bypass the CD47 Immune Checkpoint." Poster Presentation. Society for Immunotherapy of Cancer (SITC) Meeting, Washington, DC, United

(56) References Cited

OTHER PUBLICATIONS

States. https://secureservercdn.net/45.40.149.113/74d.fcf.myftpupload.com/wp-content/uploads/2021/11/CRISPR_CAR-M_Poster_101721_share-Read-Only.pdf.

"Strauss, et al., "The immunophenotype of antigen presenting cells of the mononuclear phagocyte system in a normal human liver—A systematic review" Journal of Hepatology, (2015) vol. 62, pp. 458-468".

Wong KL et al., "The three human monocyte subsets: implications for health and disease." Immunol Res. Sep. 2012;53(1-3):41-57. Epub Mar. 20, 2012.

Nakamizo, S. et al.: Single-cell analysis of human skin identifies CD14+ type 3 dendritic cells co-producing IL1B and IL23A in psoriasis. J Exp Med 218(9):e20202345 (2021); pp. 1-17. https://doi.org/10.1084/jem.20202345.

Oates, TCL et al.: Characterizing the polarization continuum of macrophage subtypes M1, M2a and M2c. bioRxiv (2022), pp. 1-33. doi: https://doi.org/10.1101/2022.06.13.495868.

* cited by examiner

CHIMERIC ANTIGEN RECEPTOR DENDRITIC CELL (CAR-DC) FOR TREATMENT OF CANCER

CROSS-REFERENCE TO RELATED APPLICATION

This application is a continuation of U.S. application Ser. No. 17/559,967 filed on Dec. 22, 2021, which is a continuation of U.S. application Ser. No. 17/227,193 filed on Apr. 9, 2021, which is a continuation of U.S. application Ser. No. 15/048,922 filed on Feb. 19, 2016 that claims the benefit of U.S. Provisional Application U.S. 62/118,027 filed on Feb. 19, 2015, the contents of which are incorporated herein by reference in its entirety.

SEQUENCE LISTING

The instant application contains a Sequence Listing which has been filed electronically in ASCII format and is hereby incorporated by reference in its entirety. Said ASCII copy, originally filed in Application U.S. Ser. No. 15/048,922, is named 56371-720_307_SL.txt and is 169,493 bytes in size.

FIELD OF THE INVENTION

The present disclosure generally relates to the fields of genetics, immunology and medicine. The invention pertains to the field of immunotherapy, more specifically the invention pertains to the utilization of monocytes that have been manipulated to home to tumor cells and upon binding to tumor antigens differentiating into monocytes with cytotoxic properties to tumors, or dendritic cells.

BACKGROUND OF THE INVENTION

The immune system possesses the power to cure cancers based on published reports of immunologically mediated spontaneous regressions, which have been document in colon, lung, melanoma, liver, breast. Intriguingly, spontaneous regression clinically, as well as in an animal model of spontaneous regression, seems to be associated primarily with stimulation of the innate immune system, comprising of macrophages, NK cells, NKT cells and neutrophils. Despite the original promising of immunotherapy, which will be mentioned, the field has focused on the adaptive immune response, specifically stimulation of T and B cells, and only recently has interest re-ignited in the innate immune system.

The use of the immune system to treat cancer is theoretically appealing due to the possibilty of low toxicity, immunological memory, and ability to attack metastatic disease. Early studies suggested that vaccination to tumor antigens and tumors themselves may be possible. Specifically, Prehn back in 1957, obtained murine tumors and exposed them to irradiation to increase immunogenicity. When these tumors were implanted into animals they were rejected. Subsequent administration of the original tumors resulted in rejection of the tumors, thus suggesting that tumor specific antigens exist, which can stimulate immunity, especially subsequent to addition of a cellular stress such as irradiation. Twenty years later, using the same system it was demonstrated that cytotoxic T cells infiltrated the tumors that were implanted after rejection of the radiation induced tumors, thus demonstrating conclusively that rejection was immunologically mediated, despite the fact that the tumors were syngeneic. In humans, one of the original observations of immunological response to neoplasia was in patients with paraneoplastic disease in which immune response to breast cancer antigens results in a multiple sclerosis-like disease caused by cross reactive immunity to neural antigens that are found on the breast cancer. Specific identification of tumor antigens on a molecular basis led to the discovery that some of the antigens are either self-proteins aberrantly expressed, or mutations of self proteins.

Originally observations were made in patients bearing metastatic melanomas, and then subsequently in other tumors, that the tumors are infiltrated with various immunological components. These tumor infiltrating lymphocytes (TILs), contain populations of cells and individual clones that demonstrate tumor specificity; they lyse autologous tumor cells but not natural killer targets, allogeneic tumor cells, or autologous fibroblasts.

By isolating and expanding TILs in vitro, and then molecularly identifying what they are responding to, a variety of the well-known tumor agents have been discovered such as MAGE-1, and MAGE-3, GAGE-1, MART-1, Melan-A, gp100, gp75 (TRP-2), tyrosinase, NY-ESO-1, mutated p16, and beta catenin. It is interesting that in the case of some antigens, such as gp75, the peptide that elicits tumor rejection results from translation of an alternative open reading frame of the same gene. Thus, the gp75 gene encodes two completely different polypeptides, gp75 as an antigen recognized by immunoglobulin G antibodies in sera from a patient with cancer, and a 24-amino acid product as a tumor rejection antigen recognized by T cells. Peptides used for immunization generally are 8-9 amino acids which have been demonstrated to be displayed in association with class I MHC molecules for recognition by T cells, and tumor cells have been shown to express these naturally processed epitopes.

Despite the intellectual appeal of peptide based cancer vaccines, the response rate has been disappointingly low. According to a review by Steven Rosenberg's group at the NIH, the rate of objective response out of 440 patients treated at his institute was a dismal 2.6%.

The ability to make a universal yet versatile system to generate T cells that are capable of recognizing various types of cancers has important clinical implications for the use of T cell-based therapies, this concept was approach initially by Rosenberg's group in the ex vivo expansion of tumor infiltrating lymphocytes. One current strategy incorporates the use of genetic engineering to express a chimeric antigen receptor (CAR) on T cells. The extracellular domain of a typical CAR consists of the $V_H$ and $V_L$ domains—single-chain fragment variable (scFv)—from the antigen binding sites of a monoclonal antibody. The scFv is linked to a flexible transmembrane domain followed by a tyrosine-based activation motif such as that from CD3ζ. The so-called second and third generation CARs include additional activation domains from co-stimulatory molecules such as CD28 and CD137 (41BB) which serve to enhance T cell survival and proliferation. CAR T cells offer the opportunity to seek out and destroy cancer cells by recognizing tumor-associated antigens (TAA) expressed on their surface. As such, the recognition of a tumor cells occurs via an MHC-independent mechanism.

Various preclinical and early-phase clinical trials highlight the efficacy of CAR T cells to treat cancer patients with solid tumors and hematopoietic malignancies. Despite of the promise that CAR T cells might have in treating cancer patients there are several limitations to the generalized clinical application of CAR T cells. First, since no single tumor antigen is universally expressed by all cancer types, scFv in CAR needs to be constructed for each tumor antigen to be targeted. Second, the financial cost and labor-intensive tasks associated with identifying and engineering scFvs against a variety of tumor antigens poses a major challenge. Third, tumor antigens targeted by CAR could be down-regulated or mutated in response to treatment resulting in tumor evasion. Since current CAR T cells recognize only one target antigen, such changes in tumors negate the therapeutic effects. Therefore, the generation of CAR T cells capable of recognizing multiple tumor antigens is highly desired. Finally, CAR T cells react with target antigen weakly expressed on non-tumor cells, potentially causing severe adverse effects. To avoid such "on-target off-tumor" reaction, use of scFvs with higher specificity to tumor antigen is required. And although ongoing studies are focused on generating methods to shut off CAR T cells in vivo this system has yet to be developed and might pose additional inherent challenges.

The current patent seeks to apply chimeric antigen receptor technology to activation of monocytes, which naturally home into tumors, to differentiated intratumorally said monocytes into dendritic cells which are capable of antigen presentation, as well as direct killing of tumors.

DETAILED DESCRIPTION OF THE INVENTION

Chimeric antigen receptor (CAR) cellular therapeutics have revolutionized the treatment of B cell malignancies achieving stunning success rates. Unfortunately, solid tumors have yet to benefit from this treatment. Additionally, patients treated with CAR-T cells lack B cells for the rest of their lives, as well as having the possibility of tumor lysis syndrome. This is in part due to the permanence of the CAR-T cells in the patients after treatment. The current invention applies the use of CAR technology to monocytes with the purpose of inducing differentiation to dendritic cells (DC) subsequent to contact with tumor antigens. Given that monocytes have a fixed mitotic index, fears of permanent manipulation of the host are diminished.

"Treating a cancer", "inhibiting cancer", "reducing cancer growth" refers to inhibiting or preventing oncogenic activity of cancer cells. Oncogenic activity can comprise inhibiting migration, invasion, drug resistance, cell survival, anchorage-independent growth, non-responsiveness to cell death signals, angiogenesis, or combinations thereof of the cancer cells.

The terms "cancer", "cancer cell", "tumor", and "tumor cell" are used interchangeably herein and refer generally to a group of diseases characterized by uncontrolled, abnormal growth of cells (e.g., a neoplasia). In some forms of cancer, the cancer cells can spread locally or through the bloodstream and lymphatic system to other parts of the body ("metastatic cancer").

"Ex vivo activated lymphocytes", "lymphocytes with enhanced antitumor activity" and "dendritic cell cytokine induced killers" are terms used interchangeably to refer to composition of cells that have been activated ex vivo and subsequently reintroduced within the context of the current invention. Although the word "lymphocyte" is used, this also includes heterogenous cells that have been expanded during the ex vivo culturing process including dendritic cells, NKT cells, gamma delta T cells, and various other innate and adaptive immune cells.

As used herein, "cancer" refers to all types of cancer or neoplasm or malignant tumors found in animals, including leukemias, carcinomas and sarcomas. Examples of cancers are cancer of the brain, melanoma, bladder, breast, cervix, colon, head and neck, kidney, lung, non-small cell lung, mesothelioma, ovary, prostate, sarcoma, stomach, uterus and Medulloblastoma.

The term "leukemia" is meant broadly progressive, malignant diseases of the hematopoietic organs/systems and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemi.

The term "carcinoma" refers to a malignant new growth made up of epithelial cells tending to infiltrate the surrounding tissues, and/or resist physiological and non-physiological cell death signals and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti.

The term "sarcoma" generally refers to a tumor which is made up of a substance like the embryonic connective tissue and is generally composed of closely packed cells embedded in a fibrillar, heterogeneous, or homogeneous substance. Sarcomas include, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma. Additional exemplary neoplasias include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some particular embodiments of the invention, the cancer treated is a melanoma. The term "melanoma" is taken to mean a tumor arising from the melanocytic system of the skin and other organs. Melanomas include, for example, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

The term "polypeptide" is used interchangeably with "peptide", "altered peptide ligand", and "flourocarbonated peptides."

The term "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

The term "T cell" is also referred to as T lymphocyte, and means a cell derived from thymus among lymphocytes involved in an immune response. The T cell includes any of a CD8-positive T cell (cytotoxic T cell: CTL), a CD4-positive T cell (helper T cell), a suppressor T cell, a regulatory T cell such as a controlling T cell, an effector cell, a naive T cell, a memory T cell, an αβT cell expressing TCR α and β chains, and a γδ T cell expressing TCR γ and δ chains. The T cell includes a precursor cell of a T cell in which differentiation into a T cell is directed.

Examples of "cell populations containing T cells" include, in addition to body fluids such as blood (peripheral blood, umbilical blood etc.) and bone marrow fluids, cell populations containing peripheral blood mononuclear cells (PBMC), hematopoietic cells, hematopoietic stem cells, umbilical blood mononuclear cells etc., which have been collected, isolated, purified or induced from the body fluids. Further, a variety of cell populations containing T cells and derived from hematopoietic cells can be used in the present invention. These cells may have been activated by cytokine such as IL-2 in vivo or ex vivo. As these cells, any of cells collected from a living body, or cells obtained via ex vivo culture, for example, a T cell population obtained by the method of the present invention as it is, or obtained by freeze preservation, can be used.

The term "antibody" is meant to include both intact molecules as well as fragments thereof that include the antigen-binding site. Whole antibody structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain.

The term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

The terms "individual", "host", "subject", and "patient" are used interchangeably herein, and refer to a mammal, including, but not limited to, primates, for example, human beings, as well as rodents, such as mice and rats, and other laboratory animals.

As used herein, the term "treatment regimen" refers to a treatment of a disease or a method for achieving a desired physiological change, such as increased or decreased response of the immune system to an antigen or immunogen, such as an increase or decrease in the number or activity of one or more cells, or cell types, that are involved in such response, wherein said treatment or method comprises administering to an animal, such as a mammal, especially a human being, a sufficient amount of two or more chemical agents or components of said regimen to effectively treat a disease or to produce said physiological change, wherein said chemical agents or components are administered together, such as part of the same composition, or administered separately and independently at the same time or at different times (i.e., administration of each agent or component is separated by a finite period of time from one or more of the agents or components) and where administration of said one or more agents or components achieves a result greater than that of any of said agents or components when administered alone or in isolation.

The term "anergy" and "unresponsiveness" includes unresponsiveness to an immune cell to stimulation, for example, stimulation by an activation receptor or cytokine. The anergy may occur due to, for example, exposure to an immune suppressor or exposure to an antigen in a high dose. Such anergy is generally antigen-specific, and continues even after completion of exposure to a tolerized antigen. For example, the anergy in a T cell and/or NK cell is characterized by failure of production of cytokine, for example, interleukin (IL)-2. The T cell anergy and/or NK cell anergy occurs in part when a first signal (signal via TCR or CD-3) is received in the absence of a second signal (costimulatory signal) upon exposure of a T cell and/or NK cell to an antigen.

The term "enhanced function of a T cell", "enhanced cytotoxicity" and "augmented activity" means that the effector function of the T cell and/or NK cell is improved. The enhanced function of the T cell and/or NK cell, which does not limit the present invention, includes an improvement in the proliferation rate of the T cell and/or NK cell, an increase in the production amount of cytokine, or an improvement in cytotoxity. Further, the enhanced function of the T cell and/or NK cell includes cancellation and suppression of tolerance of the T cell and/or NK cell in the suppressed state such as the anergy (unresponsive) state, or the rest state, that is, transfer of the T cell and/or NK cell from the suppressed state into the state where the T cell and/or NK cell responds to stimulation from the outside.

The term "expression" means generation of mRNA by transcription from nucleic acids such as genes, polynucleotides, and oligonucleotides, or generation of a protein or a polypeptide by transcription from mRNA. Expression may be detected by means including RT-PCR, Northern Blot, or in situ hybridization.

"Suppression of expression" refers to a decrease of a transcription product or a translation product in a significant amount as compared with the case of no suppression. The suppression of expression herein shows, for example, a decrease of a transcription product or a translation product in an amount of 30% or more, preferably 50% or more, more preferably 70% or more, and further preferably 90% or more.

In one embodiment of the invention the CAR-DC are antigen-loaded and co-cultured with T-lymphocytes to produce antigen-specific T-cells. As used herein, the term "antigen-specific T-cells" refers to T-cells that proliferate upon exposure to the antigen-loaded APCs of the present invention, as well as to develop the ability to attack cells having the specific antigen on their surfaces. Such T-cells, e.g., cytotoxic T-cells, lyse target cells by a number of methods, e.g., releasing toxic enzymes such as granzymes and perforin onto the surface of the target cells or by effecting the entrance of these lytic enzymes into the target cell interior. Generally, cytotoxic T-cells express CD8 on their cell surface. T-cells that express the CD4 antigen CD4, commonly known as "helper" T-cells, can also help promote specific cytotoxic activity and may also be activated by the antigen-loaded APCs of the present invention. In certain embodiments, the cancer cells, the APCs and even the T-cells can be derived from the same donor whose MNC yielded the DC, which can be the patient or an HLA—or obtained from the individual patient that is going to be treated. Alternatively, the cancer cells, the APCs and/or the T-cells can be allogeneic.

The invention provides means of inducing an anti-cancer response in a mammal, comprising the steps of initially "priming" the mammal by administering an agent that causes local accumulation of CAR-DC. Subsequently, a tumor antigen is administered in the local area where said agents causing accumulation of antigen presenting cells is administered. A time period is allowed to pass to allow for said antigen presenting cells to traffic to the lymph nodes. Subsequently a maturation signal, or a plurality of maturation signals are administered to enhance the ability of said antigen presenting cell to activate adaptive immunity. In some embodiments of the invention activators of adaptive immunity are concurrently given, as well as inhibitors of the tumor derived inhibitors are administered to derepress the immune system.

In one embodiment priming of the patient is achieved by administration of GM-CSF subcutaneously in the area in which antigen is to be injected. Various scenarios are known in the art for administration of GM-CSF prior to administration, or concurrently with administration of antigen. The practitioner of the invention is referred to the following publications for dosage regimens of GM-CSF and also of peptide antigens.

Subsequent to priming, the invention calls for administration of tumor antigen. Various tumor antigens may be utilized, in one preferred embodiment, lysed tumor cells from the same patient area utilized. Means for generation of lyzed tumor cells are well known in the art and described in the following references. One example method for generation of tumor lysate involves obtaining frozen autologous samples which are placed in hanks buffered saline solution (HBSS) and gentamycin 50 µg/ml followed by homogenization by a glass homogenizer. After repeated freezing and thawing, particle-containing samples are selected and frozen in aliquots after radiation with 25 kGy. Quality assessment for sterility and endotoxin content is performed before freezing. Cell lysates are subsequently administered into the patient in a preferred manner subcutaneously at the local areas where DC priming was initiated. After 12-72 hours, the patient is subsequently administered with an agent capable of inducing maturation of DC. Agents useful for the practice of the invention, in a preferred embodiment include BCG and HMGB1 peptide. Other useful agents include: a) histone DNA; b) imiqimod; c) beta-glucan; d) hsp65; e) hsp90; f) HMGB-1; g) lipopolysaccharide; h) Pam3CSK4; i) Poly I: Poly C; j) Flagellin; k) MALP-2; l) Imidazoquinoline; m) Resiquimod; n) CpG oligonucleotides; o) zymosan;

p) peptidoglycan; q) lipoteichoic acid; r) lipoprotein from gram-positive bacteria; s) lipoarabinomannan from mycobacteria; t) Polyadenylic-polyuridylic acid; u) monophosphoryl lipid A; v) single stranded RNA; w) double stranded RNA; x) 852A; y) rintatolimod; z) Gardiquimod; and aa) lipopolysaccharide peptides. The procedure is performed in a preferred embodiment with the administration of IDO silencing siRNA or shRNA containing the effector sequences a) UUAUAAUGACUGGAUGUUC; b) GUCUGGUGUAUGAAGGGUU; c) CUCCUAUUUUG-GUUUAUGC and d) GCAGCGUCUUUCAGUGCUU. siRNA or shRNA may be administered through various modalities including biodegradable matrices, pressure gradients or viral transfect. In another embodiment, autologous dendritic cells are generated and IDO is silenced, prior to, concurrent with or subsequent to silencing, said dendritic cells are pulsed with tumor antigen and administered systemically.

In one embodiment of the invention mature DC are modified with CAR transfection prior to administration. Culture of dendritic cells is well known in the art, for example, U.S. Pat. No. 6,936,468, issued to Robbins, et al., for the use of tolerogenic dendritic cells for enhancing tolerogenicity in a host and methods for making the same. Although the current invention aims to reduce tolerogenesis, the essential means of dendritic cell generation are disclosed in the patent. U.S. Pat. No. 6,734,014, issued to Hwu, et al., for methods and compositions for transforming dendritic cells and activating T cells. Briefly, recombinant dendritic cells are made by transforming a stem cell and differentiating the stem cell into a dendritic cell. The resulting dendritic cell is said to be an antigen presenting cell which activates T cells against MHC class 1-antigen targets. Antigens for use in dendritic cell loading are taught in, e.g., U.S. Pat. No. 6,602,709, issued to Albert, et al. This patent teaches methods for use of apoptotic cells to deliver antigen to dendritic cells for induction or tolerization of T cells. The methods and compositions are said to be useful for delivering antigens to dendritic cells that are useful for inducing antigen-specific cytotoxic T lymphocytes and T helper cells. The disclosure includes assays for evaluating the activity of cytotoxic T lymphocytes. The antigens targeted to dendritic cells are apoptotic cells that may also be modified to express non-native antigens for presentation to the dendritic cells. The dendritic cells are said to be primed by the apoptotic cells (and fragments thereof) capable of processing and presenting the processed antigen and inducing cytotoxic T lymphocyte activity or may also be used in vaccine therapies. U.S. Pat. No. 6,455,299, issued to Steinman, et al., teaches methods of use for viral vectors to deliver antigen to dendritic cells. Methods and compositions are said to be useful for delivering antigens to dendritic cells, which are then useful for inducing T antigen specific cytotoxic T lymphocytes. The disclosure provides assays for evaluating the activity of cytotoxic T lymphocytes. Antigens are provided to dendritic cells using a viral vector such as influenza virus that may be modified to express non-native antigens for presentation to the dendritic cells. The dendritic cells are infected with the vector and are said to be capable of presenting the antigen and inducing cytotoxic T lymphocyte activity or may also be used as vaccines.

Immune cells for use in the practice of the invention include DCs, the presence of which may be checked in the previously described method, are preferably selected from myeloid cells (such as monocytic cells and macrophages) expressing langerin, MHC (major histocompatibility complex) class 11, CCR2 (chemokine (C-C motif) receptor 2), CX3CR1 and/or Gr1 molecules in mice; myeloid cells expressing CD14, CD16, HLA dR (human leukocyte antigen disease resistance) molecule, langerin, CCR2 and/or CX3CR1 in humans; dendritic cells expressing CD11c, MHC class II molecules, and/or CCR7 molecules; and IL-1p producing dendritic cells. CD8 T cells, the presence of which may be checked in the previously described method, are preferably selected from CD3+, CD4+ and/or CD8+ T lymphocytes, FOXP3 (forkhead box P3) T lymphocytes, Granzyme B/TIA (Tcell-restricted intracellular antigen) T lymphocytes, and Tc1 cells (IFN-.gamma. producing CD8+ T lymphocytes). Immune cells expressing a protein that binds calreticulin, such immune cells may be selected from cells expressing at least one of the following proteins: LRP1 (Low density lipoprotein receptor-related protein 1, CD91), Ca.sup.++-binding proteins such as SCARF1 and SCARF2, MSR1 (Macrophage scavenger receptor 1), SRA, CD59 (protectin), CD207 (langerin), and THSD1 (thrombospondin). There are numerous means known in the art to identify cells expressing various antigens, these include immunochemistry, immunophenotyping, flow cytometry, Elispots assays, classical tetramer staining, and intracellular cytokine stainings.

Macrophages selectively phagocytose tumor cells, but this process is countered by protective molecules on tumor cells such as CD47, which binds macrophage signal-regulatory protein a to inhibit phagocytosis. Blockade of CD47 on tumor cells leads to phagocytosis by macrophages. In one embodiment of the invention CAR-MSC are administered together with an agent that blocks CD47 activity. It has been demonstrated that activation of TLR signaling pathways in macrophages synergizes with blocking CD47 on tumor cells to enhance tumor phagocytosis. Bruton's tyrosine kinase (Btk) mediates TLR signaling in macrophages. Calreticulin, previously shown to be a protein found on cancer cells that activated macrophage phagocytosis of tumors, is activated in macrophages for secretion and cell-surface exposure by TLR and Btk to target cancer cells for phagocytosis, even if the cancer cells themselves do not express calreticulin. In one embodiment of the invention TLR agonists are administered that stimulate expression of calreticulin and/or enhance macrophage phagocytosis of tumors.

IL-27 induces macrophage ability to kill tumor cells in vitro and in vivo, as well as altering the tumor promoting M2/myeloid suppressor cells into tumoricidal cells. In one embodiment of the invention addition of IL-27 or compounds capable of activating the IL-27 receptor signaling are administered together with IL-27 to enhance tumor phagocytosis by macrophages.

Tumor-associated macrophages, deriving from monocytes or migrating into the tumor, are an important constituent of tumor microenvironments, which in many cases modulates tumor growth, tumor angiogenesis, immune suppression, metastasis and chemoresistance. Mechanisms of macrophage promotion of tumor growth include production of EGF, M-CSF, VEGF.

Macrophage infiltration of tumors is associated with poor prognosis in renal, melanoma, breast, pancreatic, lung, endometrial, bladder, prostate.

Tumor growth are inhibited when monocytes/macrophages are ablated. There is ample evidence that many anticancer modalities currently used in the clinic have unique and distinct properties that modulate the recruitment, polarization and tumorigenic activities of macrophages in the tumor microenvironments. By manipulating tumor-associated macrophages significant impact on the clinical efficacies of and resistance to these anticancer modalities.

Accordingly, in one aspect of the invention, CAR-DC, CAR-monocytes, or CAR-macrophages are utilized to force the tumor microenvironment to stimulate tumor killing and inhibit macrophage or macrophage related cells from promoting tumor growth. Within the context of the invention, the use of drugs targeting tumor-associated macrophages, especially c-Fms kinase inhibitors and humanized antibodies targeting colony-stimulating factor-1 receptor, are envisioned.

Tumors mediate various effects to reprogram macrophages, these are usually mediated via IL-10 and other cytokines such as VEGF, TGF-beta, and M-CSF, which cause macrophages to lose tumor cytotoxicity and shift into tumor promoting, immune suppressive, angiogenic supporting cells. Related to tumor manipulated monocytes are myeloid derived suppressor cells, which are similar to myeloid progenitor cells, or the previously described "natural suppressor" cell.

Irradiated tissues induce a TLR-1 reprogramming of macrophages to promote tumor growth and angiogenesis. Macrophage promotion of tumor growth is seen in numerous situations, in one example, treating of tumor bearing animals with BRAF inhibitors results in upregulation of macrophage production of VEGF which accelerates tumor growth. Mechanistically, it is known that tumors produce factors such as GM-CSF which in part stimulate macrophages to produce CCL18, which promotes tumor metastasis. Additionally, the lactic acid microenvironment of the tumor has been shown to promote skewing of macrophages towards at tumor-promoting M2 type. It has been shown that lactic acid produced by tumour cells, as a by-product of aerobic or anaerobic glycolysis, possesses an essential role in inducing the expression of VEGF and the M2-like polarization of tumour-associated macrophages, specifically inducing expression of arginase 1 through a HIF-1alpha dependent pathway. Mechanistically, it is known that lactic acid in tumors is generated in a large part by lactate dehydrogenase-A (LDH-A), which converts pyruvate to lactate. siRNA silencing of LDH-A in Pan02 pancreatic cancer cells that are injected in C57BL/6 mice results in development of smaller tumors than mice injected with wild type, non-silenced Pan02 cells. Associated with the reduced tumor growth were observations of a decrease in the frequency of myeloid-derived suppressor cells (MDSCs) in the spleens of mice carrying LDH-A-silenced tumors. NK cells from LDH-A-depleted tumors had improved cytolytic function. Exogenous lactate administration was shown to increase the frequency of MDSCs generated from mouse bone marrow cells with GM-CSF and IL-6 in vitro. Furthermore lactate pretreatment of NK cells in vitro inhibited cytolytic function of both human and mouse NK cells. This reduction of NK cytotoxic activity was accompanied by lower expression of perforin and granzyme in NK cells. The expression of NKp46 was lower in lactate-treated NK cells. Accordingly, in one embodiment of the invention, depletion of glucose levels using a ketogenic diet to lower lactate production by glycolytic tumors is utilized to augment therapeutic effects of CAR-DC. Utilization of ketogenic diet has been previously described for immune modulation, and cancer therapy. Specific quantification of intratumoral lactate and its manipulation has been described and incorporated by reference. Potentiation of chemotherapeutic and radiotherapeutic effects by ketogenic diets have been reported and techniques are incorporated by reference for use with the current CAR-DC invention. Suppression of tumor growth and activity induced by ketogenic diet may be augmented by addition of hyperbaric oxygen, thus in one embodiment of the invention, the utilization of oxidative therapies, as disclosed in references incorporated, together with ketogenic diet is utilized to augment therapeutic efficacy of CAR-DC.

Not only has it been well known that monocytes and macrophages infiltrate tumors and appear to support tumor growth through growth factor production and secretion of angiogenic agents, but suggestions have been made that tumors themselves, as part of the epithelial mesenchymal transition may actually differentiate into monocytes in part associated with TGF-beta production. Specifically, a study reported performing gene-profiling analysis of mouse mammary EpRas tumor cells that had been allowed to adopt an epithelial to mesenchymal transition program after long-term treatment with TGF-$\beta$1 for 2 weeks. While the treated cells acquired traits of mesenchymal cell differentiation and migration, gene analysis revealed another cluster of induced genes, which was specifically enriched in monocyte-derived macrophages, mast cells, and myeloid dendritic cells, but less in other types of immune cells. Further studies revealed that this monocyte/macrophage gene cluster was enriched in human breast cancer cell lines displaying an EMT or a Basal B profile, and in human breast tumors with EMT and undifferentiated (ER-/PR-) characteristics. The plasticity of tumor cells to potentially monocytic lineages should come as no surprise given that tumor cells have been shown to differentiate directly into pericytes, and endothelial cells/vascular channels.

Dopamine possesses antiangiogenic effects as well as myeloprotective effects, in one embodiment of the invention addition of dopamine to the CAR-DC treatment is disclosed.

Vinblastine is a widely used chemotherapeutic agent that has been demonstrated to induce dendritic cell maturation. In one embodiment of the invention CAR-DC are utilized together with vinblastine therapy to induce augmented anticancer activity. Oxiplatin and anthracyclines have been demonstrated to not only directly kill tumor cells but also stimulate T cell immunity against tumor cells. It was demonstrated that these agents induce a rapid and prominent invasion of interleukin (IL)-17-producing $\gamma\delta$ (V$\gamma$4(+) and V$\gamma$6(+)) T lymphocytes ($\gamma\delta$ T17 cells) that precedes the accumulation of CD8 CTLs within the tumor bed. In T cell receptor $\delta$(-/-) or V$\gamma$4/6(-/-) mice, the therapeutic efficacy of chemotherapy was reduced and furthermore no IL-17 was produced by tumor-infiltrating T cells, and CD8 CTLs did not invade the tumor after treatment. Although $\gamma\delta$ Th17 cells could produce both IL-17A and IL-22, the absence of a functional IL-17A-IL-17R pathway significantly reduced tumor-specific T cell responses elicited by tumor cell death, and the efficacy of chemotherapy in four independent transplantable tumor models. The adoptive transfer of $\gamma\delta$ T cells to naïve mice restored the efficacy of chemotherapy in IL-17A(-/-) hosts. The anticancer effect of infused $\gamma\delta$ T cells was lost when they lacked either IL-1R1 or IL-17A.

Intratumoral injection of dendritic cells stimulates antitumor immunity in vivo in clinical situations, suggesting that modulating the antigen presenting cell in the tumor microenvironment will induce an antitumor response. Administration of radiotherapy to tumors to induce immunogenic cell death, followed by intratumoral administration of DC has been demonstrated to result in enhanced antigen presentation, accordingly, this technique may be modified to enhance effects of CAR-DC. The induction of immunity to tumors in the present invention is associated with the unique nature of: a) ongoing basal cell death within the tumor; and b) cell death induced by chemotherapy, radiotherapy, hyperthermia, or otherwise induced cell death. Cell death can be classified according to the morphological appearance of the lethal process (that may be apoptotic, necrotic, autophagic or associated with mitosis), enzymological criteria (with and without the involvement of nucleases or distinct classes of proteases, like caspases), functional aspects (programmed or accidental, physiological or pathological) or immunological characteristics (immunogenic or non-immunogenic). Cell death is defined as "immunogenic" or "immune stimulatory" if dying cells that express a specific antigen (for example a tumor associated antigen, phosphotidyl serine, or calreticulin), yet are uninfected (and hence lack pathogen-associated molecular patterns), and are injected subcutaneously into mice, in the absence of any adjuvant, cause a protective immune response against said specific antigen. Such a protective immune response precludes the growth of living transformed cells expressing the specific antigen injected into mice. When cancer cells succumb to an immunogenic cell death (or immunogenic apoptosis) modality, they stimulate the immune system, which then mounts a therapeutic anti-cancer immune response and contributes to the eradication of residual tumor cells. Conversely, when cancer cells succumb to a non-immunogenic death modality, they fail to elicit such a protective immune response. Regardless of the types of cell death that are ongoing, the tumor derived immune suppressive molecules contribute to general inhibition or inability of the tumor to be eliminated.

Within the practice of the invention, CAR-DC are administered concurrently, prior to, or subsequent to administration of an agent that induces immunogenic cell death in a patient. Methods of determining whether compounds induce immunogenic cell death are known in the art and include the following, which was described by Zitvogel et al. (a) treating the cells, the mammalian cells and inducing the cell death or apoptosis, typically of mammalian cancer cells capable of expressing calreticulin (CRT), by exposing said mammalian cells to a particular drug (the test drug), for example 18 hours; (b) inoculating (for example intradermally) the dying mammalian cells from step (a) in a particular area (for example a flank) of the mammal, typically a mouse, to induce an immune response in this area of the mammal; (c) inoculating (for example intradermally) the minimal tumorigenic dose of syngeneic live tumor cells in a distinct area (for example the opposite flank) from the same mammal, for example 7 days after step (b); and (d) comparing the size of the tumor in the inoculated mammal with a control mammal also exposed to the minimal tumorigenic dose of syngeneic live tumor cells of step (c) [for example a mouse devoid of T lymphocyte], the stabilization or regression of the tumor in the inoculated mammal being indicative of the drug immunogenicity. Other in vitro means are available for assessing the ability of various drugs or therapeutic approaches to induce immunogenic cell death. Specific characteristics to assess when screening for immunogenic cell death include: a) ability to induce dendritic cell maturation in vitro; b) ability to activate NK cells; and c) ability to induce activation of gamma delta T cells or NKT cells. Specific drugs known to induce immunogenic cell death include oxiplatine and anthracyclines, as well as radiotherapy, and hyperthermia. In the case of chemotherapies, certain chemotherapies that activate TLR4 through induction of HMGB1 have been observed to function suboptimally in patients that have a TLR4 polymorphism, thus suggesting actual contribution of TLR activation as a means of chemotherapy inhibition of cancer. Additionally, oncoviruses or oncolytic viruses are known to induce immunogenic cell death and may be useful for the practice of the invention.

The CAR-DC disclosed in the invention may be utilized in combination with conventional immune modulators including BCG, CpG DNA, interferon alpha, tumor bacterial therapy, checkpoint inhibitors, Treg depleting agents, and low dose cyclophosphamide.

In one embodiment of the invention CAR-DC cells are generated with specificity towards ROBO-4. Numerous means of generating CAR-T cells are known in the art, which are applied to CAR-DC. In one embodiment of the invention FMC63-28z CAR (Genebank identifier HM852952.1), is used as the template for the CAR except the anti-CD19, single-chain variable fragment sequence is replaced with an ROBO-4 fragment. The construct is synthesized and inserted into a pLNCX retroviral vector. Retroviruses encoding the ROBO-4-specific CAR are generated using the retrovirus packaging kit, Ampho (Takara), following the manufacturer's protocol. For generation of CAR-DC cells donor blood is obtained and after centrifugation on Ficoll-Hypaque density gradients (Sigma-Aldrich), PBMCs are plated at $2 \times 10(6)$ cells/mL in cell culture for 2 hours and the adherent cells are collected. The cells were then stimulated for 2 days on a tissue-culture-treated 24-well plate containing M-CSF at a concentration of 100 ng/ml For retrovirus transduction, a 24-well plate are coated with RetroNectin (Takara) at 4° C. overnight, according to the manufacturer's protocol, and then blocked with 2% BSA at room temperature for 30 min. The plate was then loaded with retrovirus supernatants at 300 µL/well and incubated at 37° C. for 6 h. Next, $1 \times 10(6)$ stimulated adherent cells in 1 mL of medium are added to 1 mL of retrovirus supernatants before being transferred to the pre-coated wells and cultured at 37° C. for 2 d. The cells are then transferred to a tissue-culture-treated plate at $1 \times 10(6)$ cells/mL and cultured in the presence of 100 U/mL of recombinant human M-CSF, applying the T cell protocol but not utilizing IL-2 or antiCD3/antiCD28.

Other means of generating CARs are known in the art and incorporated by reference. For example, Groner's group genetically modified T lymphocytes and endowed them with the ability to specifically recognize cancer cells. Tumor cells overexpressing the ErbB-2 receptor served as a model. The target cell recognition specificity was conferred to T lymphocytes by transduction of a chimeric gene encoding the zeta-chain of the TCR and a single chain antibody (scFv (FRP5)) directed against the human ErbB-2 receptor. The chimeric scFv(FRP5)-zeta gene was introduced into primary mouse T lymphocytes via retroviral gene transfer. Naive T lymphocytes were activated and infected by cocultivation with a retrovirus-producing packaging cell line. The scFv (FRP5)-zeta fusion gene was expressed in >75% of the T cells. These T cells lysed ErbB-2-expressing target cells in vitro with high specificity. In a syngeneic mouse model, mice were treated with autologous, transduced T cells. The adoptively transferred scFv(FRP5)-zeta-expressing T cells caused total regression of ErbB-2-expressing tumors. The presence of the transduced T lymphocytes in the tumor tissue was monitored. No humoral response directed against the transduced T cells was observed. Abs directed against the ErbB-2 receptor were detected upon tumor lysis. Hombach et al. constructed an anti-CEA chimeric receptor whose extracellular moiety is composed of a humanized scFv derived from the anti-CEA mAb BW431/26 and the CH2/CH3 constant domains of human IgG. The intracellular moiety consists of the gamma-signaling chain of the human Fc epsilon RI receptor constituting a completely humanized chimeric receptor. After transfection, the humBW431/26 scFv-CH2CH3-gamma receptor is expressed as a homodimer on the surface of MD45 T cells. Co-incubation with CEA+ tumor cells specifically activates grafted MD45 T cells indicated by IL-2 secretion and cytolytic activity against CEA+ tumor cells. Notably, the efficacy of receptor-mediated activation is not affected by soluble CEA up to 25 micrograms/ml demonstrating the usefulness of this chimeric receptor for specific cellular activation by membrane-bound CEA even in the presence of high concentrations of CEA, as found in patients during progression of the disease (200). These methods are described to guide one of skill in the art to practicing the invention, which in one embodiment is the utilization of CAR T cell approaches towards targeting tumor endothelium as compared to simply targeting the tumor itself.

Targeting of mucins associated with cancers has been performed with CAR T cells by grafting the antibody that binds to the mucin with CD3 zeta chain. For the purpose of the invention, this procedure is modified for CAR-DC. In an older publication chimeric immune receptor consisting of an extracellular antigen-binding domain derived from the CC49 humanized single-chain antibody, linked to the CD3zeta signaling domain of the T cell receptor, was generated (CC49-zeta). This receptor binds to TAG-72, a mucin antigen expressed by most human adenocarcinomas. CC49-zeta was expressed in CD4+ and CD8+ T cells and induced cytokine production on stimulation. Human T cells expressing CC49-zeta recognized and killed tumor cell lines and primary tumor cells expressing TAG-72. CC49-zeta T cells did not mediate bystander killing of TAG-72-negative cells. In addition, CC49-zeta T cells not only killed FasL-positive tumor cells in vitro and in vivo, but also survived in their presence, and were immunoprotective in intraperitoneal and subcutaneous murine tumor xenograft models with TAG-72-positive human tumor cells. Finally, receptor-positive T cells were still effective in killing TAG-72-positive targets in the presence of physiological levels of soluble TAG-72, and did not induce killing of TAG-72-negative cells under the same conditions.

For clinical practice of the invention several reports exist in the art that would guide the skilled artisan as to concentrations, cell numbers, and dosing protocols useful. While in the art CAR T cells have been utilized targeting surface tumor antigens, the main issue with this approach is the difficulty of T cells to enter tumors due to features specific to the tumor microenvironment. These include higher interstitial pressure inside the tumor compared to the surroundings, acidosis inside the tumor, and expression in the tumor of FasL which kills activated T cells. Accordingly the invention seeks to more effectively utilize CAR-DC cells by directly targeting them to tumor endothelium, which is in direct contact with blood and therefore not susceptible to intratumoral factors the limit efficacy of conventional T cell therapies. In other embodiments CAR-DC are targeting to tumor antigens.

In one embodiment of the invention, protocols similar to Kershaw et al. are utilized with the exception that tumor endothelial antigens are targeted as opposed to conventional tumor antigens. Such tumor endothelial antigens include CD93, TEM-1, VEGFR1, and survivin. Antibodies can be made for these proteins, methodologies for which are described in U.S. Pat. Nos. 5,225,539, 5,585,089, 5,693,761, and 5,639,641. In one example that may be utilized as a template for clinical development, T cells with reactivity against the ovarian cancer-associated antigen alpha-folate receptor (FR) were generated by genetic modification of autologous T cells with a chimeric gene incorporating an anti-FR single-chain antibody linked to the signaling domain of the Fc receptor gamma chain. Patients were assigned to one of two cohorts in the study. Eight patients in cohort 1 received a dose escalation of T cells in combination with high-dose interleukin-2, and six patients in cohort 2 received dual-specific T cells (reactive with both FR and allogeneic cells) followed by immunization with allogeneic peripheral blood mononuclear cells. Five patients in cohort 1 experienced some grade 3 to 4 treatment-related toxicity that was probably due to interleukin-2 administration, which could be managed using standard measures. Patients in cohort 2 experienced relatively mild side effects with grade 1 to 2 symptoms. No reduction in tumor burden was seen in any patient. Tracking 111In-labeled adoptively transferred T cells in cohort 1 revealed a lack of specific localization of T cells to tumor except in one patient where some signal was detected in a peritoneal deposit. PCR analysis showed that gene-modified T cells were present in the circulation in large numbers for the first 2 days after transfer, but these quickly declined to be barely detectable 1 month later in most patients. Similar CAR-T clinical studies have been reported for neuroblastoma, B cell malignancies, melanoma, ovarian cancer, renal cancer, mesothelioma, and head and neck cancer.

In one embodiment of the invention, PBMCs are derived from leukapheresis and CD14 monocytes are collected by MACS. After 3 days of culture, M-CSF at 100 ng/ml plasmid encoding the chimeric CAR-DC recognizing tumor-endothelium specific antigen and subsequently selected for gene integration by culture in G418. In another embodiment the generation of dual-specific T cells is performed, stimulation of allogeneic monocytic cells is achieved by coculture of patient PBMCs with irradiated (5,000 cGy) allogeneic donor PBMCs from cryopre-served apheresis product (mixed lymphocyte reaction). The MHC haplotype of allogeneic donors is determined before use, and donors that differed in at least four MHC class I alleles from the patient are used. Culture medium consisted of AimV medium (Invitrogen, Carlsbad, CA) supplemented with 5% human AB-serum (Valley Biomedical, Winchester, VA), penicillin (50 units/mL), streptomycin (50 mg/mL; Bio Whittaker, Walkersville, MD), amphotericin B (Fungizone, 1.25 mg/mL; Biofluids, Rockville, MD), L-glutamine (2 mmol/L; Mediatech, Herndon, VA), and human recombinant IL-2 (Proleukin, 300 IU/mL; Chiron). Mixed lymphocyte reaction consisted of $2\times10^6$ patient monocytes and $1\times10^7$ allogeneic stimulator PBMCs in 2 mL AimV per well in 24-well plates. Between 24 and 48 wells are cultured per patient for 3 days, at which time transduction is done by aspirating 1.5 mL of medium and replacing with 2.0 mL retroviral supernatant containing 300 IU/mL IL-2, 10 mmol/L HEPES, and 8 μg/mL polybrene (Sigma, St. Louis, MO) followed by covering with plastic wrap and centrifugation at 1,000×g for 1 hour at room temperature. After overnight culture at 37° C./5% $CO_2$, transduction is repeated on the following day, and then medium was replaced after another 24 hours. Cells are then resuspended at $1\times10^6$/mL in fresh medium containing 0.5 mg/mL G418 (Invitrogen) in 175-$cm^2$ flasks for 5 days before resuspension in media lacking G418. Cells are expanded to $2\times10^9$ and then restimulated with allogeneic PBMCs from the same donor to enrich for T cells specific for the donor allogeneic haplotype. Restimulation is done by incubating patient T cells ($1\times10^6$/mL) and stimulator PBMCs ($2\times10^6$/mL) in 3-liter Fenwall culture bags in AimV+additives and IL-2 (no G418). Cell numbers were adjusted to $1\times10^6$/mL, and IL-2 was added every 2 days, until sufficient numbers for treatment were achieved.

The present invention relates to a strategy of adoptive cell transfer of monocytes or DC transduced to express a chimeric antigen receptor (CAR). CARs are molecules that combine antibody-based specificity for a desired antigen (e.g., tumor endothelial antigen) with a T cell receptor-activating intracellular domain to generate a chimeric protein that exhibits a specific anti-tumor endothelium cellular immune activity. In one embodiment the present invention relates generally to the use of monocytes or DC cells genetically modified to stably express a desired CAR that possesses high affinity towards tumor associated endothelium. Monocytes or DC cells expressing a CAR are referred to herein as CAR-DC cells or CAR modified DC cells. Preferably, the cell can be genetically modified to stably express an antibody binding domain on its surface, conferring novel antigen specificity that is MHC independent. In some instances, the monocyte or DC cell is genetically modified to stably express a CAR that combines an antigen recognition domain of a specific antibody with an intracellular domain of the CD3-zeta chain or Fc.gamma.RI protein into a single chimeric protein. In another embodiment, TLR signaling molecules are engineered in the intracellular portion of the CAR, said molecules include TRIF, TRADD, and MyD99. In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8a hinge domain.

With respect to the cytoplasmic domain, the CAR of the invention can be designed to comprise the CD80 and/or CD86 and/or CD40L and/or OX40L signaling domain by itself or be combined with any other desired cytoplasmic domain(s) useful in the context of the CAR of the invention. In one embodiment, the cytoplasmic domain of the CAR can be designed to further comprise the signaling domain of MyD88. For example, the cytoplasmic domain of the CAR can include but is not limited to CD80 and/or CD86 and/or CD40L and/or OX40L signaling modules and combinations thereof. In another embodiment of the invention inhibition of TGF-beta is performed either by transfection with an shRNA possessing selectively towards TGF-beta or by constructing the CAR to possess a dominant negative mutant of TGF-beta receptor. This would render the CAR-DC cell resistant to inhibitory activities of the tumors. Accordingly, the invention provides CAR-DC cells and methods of their use for adoptive therapy. In one embodiment, the CAR-DC cells of the invention can be generated by introducing a lentiviral vector comprising a desired CAR, for example a CAR comprising anti-CD19, CD8a hinge and transmembrane domain, and MyD88, into the cells. The CAR-DC cells of the invention are able to replicate in vivo resulting in long-term persistence that can lead to sustained tumor control.

One skilled in the art will appreciate that these methods, compositions, and cells are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. It will be apparent to one skilled in the art that varying substitutions and modifications may be made to the invention disclosed herein without departing from the scope and spirit of the invention. Those skilled in the art recognize that the aspects and embodiments of the invention set forth herein may be practiced separate from each other or in conjunction with each other. Therefore, combinations of separate embodiments are within the scope of the invention as disclosed herein. All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

The invention claimed is:

1. A method of making a population of chimeric antigen receptor (CAR) encoded CD14+ cells, the method comprising:
   (a) extracting a leukapheresis sample or a PBMC sample from a human subject;
   (b) isolating CD14+ cells from CD3+ cells in the leukapheresis sample from (a) or the PBMC sample from (a);
   (c) after (b), culturing the isolated CD14+ cells ex vivo in the presence of (i) a growth factor, wherein the growth factor comprises recombinant human M-CSF and does not comprise GM-CSF and (ii) a cytokine that does not comprise IL-2,
   thereby obtaining an ex vivo population of CD14+ cells; and
   (d) introducing a recombinant polynucleic acid encoding a chimeric antigen receptor (CAR) into the ex vivo population of CD14+ cells, thereby obtaining the population of CAR encoded CD14+ cells;
   wherein the CAR comprises (i) an extracellular domain comprising an antigen binding domain; (ii) a transmembrane domain; and (iii) an intracellular domain comprising a CD3 zeta intracellular signaling domain.

2. The method of claim 1, wherein isolating CD14+ cells from the CD3+ cells in the leukapheresis sample from (a) or the PBMC sample from (a) comprises enriching CD14+ cells that are also positive for CD16.

3. The method of claim 1, wherein extracting comprises extracting a leukapheresis sample or a PBMC sample from a human subject with lymphoma or a solid tumor.

4. The method of claim 1, wherein extracting comprises extracting a leukapheresis sample or a PBMC sample from a human subject with a breast cancer or a metastatic cancer.

5. The method of claim 1, wherein extracting comprises extracting a leukapheresis sample or a PBMC sample from a human subject with an ErbB-2-expressing cancer.

6. The method of claim 1, wherein the recombinant polynucleic acid is a viral vector.

7. The method of claim 6, wherein introducing comprises transducing a viral vector encoding the CAR into the ex vivo population of CD14+ cells, thereby obtaining the population of CAR encoded CD14+ cells.

8. The method of claim 1, wherein introducing comprises transfecting the ex vivo population of CD14+ cells with the recombinant polynucleic acid encoding the CAR.

9. The method of claim 1, wherein the recombinant polynucleic acid is mRNA.

10. The method of claim 9, wherein introducing comprises introducing an mRNA encoding the CAR into the ex vivo population of CD14+ cells, thereby obtaining the population of CAR encoded CD14+ cells.

11. The method of claim 1, wherein the population of CAR encoded CD14+ cells is a population of virally transduced CAR encoded CD14+ cells.

12. The method of claim 1, wherein the population of CAR encoded CD14+ cells comprises a viral component.

13. The method of claim 1, wherein the population of CAR encoded CD14+ cells is a population of differentiated dendritic cells.

14. The method of claim 1, wherein isolating CD14+ cells from CD3+ cells in the leukapheresis sample or the PBMC sample comprises isolating CD14+ monocytes from CD3+ cells in the leukapheresis sample or the PBMC sample, isolating CD14+ macrophages CD3+ cells in from the leukapheresis sample or the PBMC sample or isolating CD14+ dendritic cells from CD3+ cells in the leukapheresis sample or the PBMC sample.

15. The method of claim 1, wherein the population of CAR encoded CD14+ cells is a population of cells that are positive for both CD14 and CD16.

16. The method of claim 1, wherein the population of CAR encoded CD14+ cells is a population of CAR encoded CD14+ monocytes, a population of CAR encoded CD14+ macrophages or a population of CAR encoded CD14+ dendritic cells.

17. The method of claim 1, wherein the population of CAR encoded CD14+ cells is phagocytic.

18. The method of claim 1, wherein the population of CAR encoded CD14+ cells is a population of differentiated M1 macrophages.

19. The method of claim 1, wherein the ex vivo population of CD14+ cells is a population of cells that are positive for both CD14 and CD16.

20. The method of claim 1, wherein the intracellular domain comprises two or more signaling domains.

21. The method of claim 1, wherein the transmembrane domain comprises a CD8a transmembrane domain or a TLR4 transmembrane domain.

22. The method of claim 1, wherein the extracellular domain further comprises a CD8a hinge domain.

23. The method of claim 1, wherein the antigen binding domain is a single domain antibody (sdAb) or a single chain variable fragment (scFv).

24. The method of claim 1, wherein the antigen binding domain is an anti-HER2/neu binding domain.

25. A pharmaceutical composition comprising a population of chimeric antigen receptor (CAR) encoded CD14+ cells made according to the method of claim 1.

* * * * *

UNITED STATES PATENT AND TRADEMARK OFFICE
CERTIFICATE OF CORRECTION

PATENT NO.        : 11,918,604 B2
APPLICATION NO.   : 17/715710
DATED             : March 5, 2024
INVENTOR(S)       : Samuel C. Wagner et al.

It is certified that error appears in the above-identified patent and that said Letters Patent is hereby corrected as shown below:

In the Claims

Claim 14, Column 122, Lines 15 and 16:
"isolating CD14+ macrophages CD3+ cells in from the leukapheresis sample" should read --isolating CD14+ macrophages from CD3+ cells in the leukapheresis sample--

Signed and Sealed this
Twenty-third Day of April, 2024

*Katherine Kelly Vidal*
Katherine Kelly Vidal
*Director of the United States Patent and Trademark Office*

SEQUENCE LISTING

```
<160> NUMBER OF SEQ ID NOS: 39

<210> SEQ ID NO 1
<211> LENGTH: 757
<212> TYPE: PRT
<213> ORGANISM: Human

<400> SEQUENCE: 1

Met Leu Leu Arg Leu Leu Leu Ala Trp Ala Ala Ala Gly Pro Thr Leu
1               5                   10                  15

Gly Gln Asp Pro Trp Ala Ala Glu Pro Arg Ala Ala Cys Gly Pro Ser
```

```
                20                  25                  30
    Ser Cys Tyr Ala Leu Phe Pro Arg Arg Thr Phe Leu Glu Ala Trp
                35                  40                  45

Arg Ala Cys Arg Glu Leu Gly Gly Asp Leu Ala Thr Pro Arg Thr Pro
    50                  55                  60

Glu Glu Ala Gln Arg Val Asp Ser Leu Val Gly Ala Gly Pro Ala Ser
    65                  70                  75                  80

Arg Leu Leu Trp Ile Gly Leu Gln Arg Gln Ala Arg Gln Cys Gln Leu
                    85                  90                  95

Gln Arg Pro Leu Arg Gly Phe Thr Trp Thr Thr Gly Asp Gln Asp Thr
                100                 105                 110

Ala Phe Thr Asn Trp Ala Gln Pro Ala Ser Gly Pro Cys Pro Ala
                115                 120                 125

Gln Arg Cys Val Ala Leu Glu Ala Ser Gly Glu His Arg Trp Leu Glu
                130                 135                 140

Gly Ser Cys Thr Leu Ala Val Asp Gly Tyr Leu Cys Gln Phe Gly Phe
    145                 150                 155                 160

Glu Gly Ala Cys Pro Ala Leu Gln Asp Glu Ala Gly Gln Ala Gly Pro
                    165                 170                 175

Ala Val Tyr Thr Thr Pro Phe His Leu Val Ser Thr Glu Phe Glu Trp
                180                 185                 190

Leu Pro Phe Gly Ser Val Ala Ala Val Gln Cys Gln Ala Gly Arg Gly
                195                 200                 205

Ala Ser Leu Leu Cys Val Lys Gln Pro Glu Gly Gly Val Gly Trp Ser
                210                 215                 220

Arg Ala Gly Pro Leu Cys Leu Gly Thr Gly Cys Ser Pro Asp Asn Gly
    225                 230                 235                 240

Gly Cys Glu His Glu Cys Val Glu Val Asp Gly His Val Ser Cys
                    245                 250                 255

Arg Cys Thr Glu Gly Phe Arg Leu Ala Ala Asp Gly Arg Ser Cys Glu
                260                 265                 270

Asp Pro Cys Ala Gln Ala Pro Cys Glu Gln Gln Cys Glu Pro Gly Gly
                275                 280                 285

Pro Gln Gly Tyr Ser Cys His Cys Arg Leu Gly Phe Arg Pro Ala Glu
                290                 295                 300

Asp Asp Pro His Arg Cys Val Asp Thr Asp Glu Cys Gln Ile Ala Gly
    305                 310                 315                 320

Val Cys Gln Gln Met Cys Val Asn Tyr Val Gly Gly Phe Glu Cys Tyr
                    325                 330                 335

Cys Ser Glu Gly His Glu Leu Glu Ala Asp Gly Ile Ser Cys Ser Pro
                340                 345                 350

Ala Gly Ala Met Gly Ala Gln Ala Ser Gln Asp Leu Gly Asp Glu Leu
                355                 360                 365

Leu Asp Asp Gly Glu Asp Glu Glu Asp Glu Asp Glu Ala Trp Lys Ala
                370                 375                 380

Phe Asn Gly Gly Trp Thr Glu Met Pro Gly Ile Leu Trp Met Glu Pro
    385                 390                 395                 400

Thr Gln Pro Pro Asp Phe Ala Leu Ala Tyr Arg Pro Ser Phe Pro Glu
                    405                 410                 415

Asp Arg Glu Pro Gln Ile Pro Tyr Pro Glu Pro Thr Trp Pro Pro
                420                 425                 430

Leu Ser Ala Pro Arg Val Pro Tyr His Ser Ser Val Leu Ser Val Thr
                435                 440                 445
```

```
Arg Pro Val Val Ser Ala Thr His Pro Thr Leu Pro Ser Ala His
    450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
                500                 505                 510

Gln Pro Pro Met Ile Ser Thr Lys Tyr Pro Glu Leu Phe Pro Ala His
            515                 520                 525

Gln Ser Pro Met Phe Pro Asp Thr Arg Val Ala Gly Thr Gln Thr Thr
    530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
                580                 585                 590

Thr Thr Thr Ser Arg Ser Pro Val Ser Pro Ala His Gln Ile Ser Val
            595                 600                 605

Pro Ala Ala Thr Gln Pro Ala Ala Leu Pro Thr Leu Leu Pro Ser Gln
    610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
                660                 665                 670

Glu Ala Gly Leu Ala Glu His Ser Gln Arg Asp Asp Arg Trp Leu Leu
            675                 680                 685

Val Ala Leu Leu Val Pro Thr Cys Val Phe Leu Val Val Leu Leu Ala
    690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
                740                 745                 750

Cys Arg Thr Ser Val
            755

<210> SEQ ID NO 2
<211> LENGTH: 1443
<212> TYPE: PRT
<213> ORGANISM: Human

<400> SEQUENCE: 2

Met Ser Leu Leu Met Phe Thr Gln Leu Leu Cys Gly Phe Leu Tyr
1               5                   10                  15

Val Arg Val Asp Gly Ser Arg Leu Arg Gln Glu Asp Phe Pro Pro Arg
                20                  25                  30

Ile Val Glu His Pro Ser Asp Val Ile Val Ser Lys Gly Glu Pro Thr
            35                  40                  45

Thr Leu Asn Cys Lys Ala Glu Gly Arg Pro Thr Pro Thr Ile Glu Trp
```

```
            50                  55                  60
Tyr Lys Asp Gly Glu Arg Val Glu Thr Asp Lys Asp Pro Arg Ser
 65                  70                  75                  80

His Arg Met Leu Leu Pro Ser Gly Ser Leu Phe Phe Leu Arg Ile Val
                     85                  90                  95

His Gly Arg Arg Ser Lys Pro Asp Glu Gly Ser Tyr Val Cys Val Ala
                100                 105                 110

Arg Asn Tyr Leu Gly Glu Ala Val Ser Arg Asn Ala Ser Leu Glu Val
                115                 120                 125

Ala Leu Leu Arg Asp Asp Phe Arg Gln Asn Pro Thr Asp Val Val Val
130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
                180                 185                 190

Thr Arg Lys Ser Asp Ala Gly Met Tyr Thr Cys Val Gly Thr Asn Met
                195                 200                 205

Val Gly Glu Arg Asp Ser Asp Pro Ala Glu Leu Thr Val Phe Glu Arg
210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
                260                 265                 270

Lys Asp Asp Tyr Thr Leu Arg Ile Lys Lys Thr Met Ser Thr Asp Glu
                275                 280                 285

Gly Thr Tyr Met Cys Ile Ala Glu Asn Arg Val Gly Lys Met Glu Ala
                290                 295                 300

Ser Ala Thr Leu Thr Val Arg Ala Arg Pro Val Ala Pro Gln Phe
305                 310                 315                 320

Val Val Arg Pro Arg Asp Gln Ile Val Ala Gln Gly Arg Thr Val Thr
                325                 330                 335

Phe Pro Cys Glu Thr Lys Gly Asn Pro Gln Pro Ala Val Phe Trp Gln
                340                 345                 350

Lys Glu Gly Ser Gln Asn Leu Leu Phe Pro Asn Gln Pro Gln Gln Pro
                355                 360                 365

Asn Ser Arg Cys Ser Val Ser Pro Thr Gly Asp Leu Thr Ile Thr Asn
370                 375                 380

Ile Gln Arg Ser Asp Ala Gly Tyr Tyr Ile Cys Gln Ala Leu Thr Val
385                 390                 395                 400

Ala Gly Ser Ile Leu Ala Lys Ala Gln Leu Glu Val Thr Asp Val Leu
                405                 410                 415

Thr Asp Arg Pro Pro Ile Ile Leu Gln Gly Pro Ala Asn Gln Thr
                420                 425                 430

Leu Ala Val Asp Gly Thr Ala Leu Leu Lys Cys Lys Ala Thr Gly Asp
                435                 440                 445

Pro Leu Pro Val Ile Ser Trp Leu Lys Glu Gly Phe Thr Phe Pro Gly
                450                 455                 460

Arg Asp Pro Arg Ala Thr Ile Gln Glu Gln Gly Thr Leu Gln Ile Lys
465                 470                 475                 480
```

```
Asn Leu Arg Ile Ser Asp Thr Gly Thr Tyr Thr Cys Val Ala Thr Ser
                485                 490                 495

Ser Ser Gly Glu Thr Ser Trp Ser Ala Val Leu Asp Val Thr Glu Ser
            500                 505                 510

Gly Ala Thr Ile Ser Lys Asn Tyr Asp Leu Ser Asp Leu Pro Gly Pro
            515                 520                 525

Pro Ser Lys Pro Gln Val Thr Asp Val Thr Lys Asn Ser Val Thr Leu
        530                 535                 540

Ser Trp Gln Pro Gly Thr Pro Gly Thr Leu Pro Ala Ser Ala Tyr Ile
545                 550                 555                 560

Ile Glu Ala Phe Ser Gln Ser Val Ser Asn Ser Trp Gln Thr Val Ala
                565                 570                 575

Asn His Val Lys Thr Thr Leu Tyr Thr Val Arg Gly Leu Arg Pro Asn
            580                 585                 590

Thr Ile Tyr Leu Phe Met Val Arg Ala Ile Asn Pro Gln Gly Leu Ser
            595                 600                 605

Asp Pro Ser Pro Met Ser Asp Pro Val Arg Thr Gln Asp Ile Ser Pro
        610                 615                 620

Pro Ala Gln Gly Val Asp His Arg Gln Val Lys Glu Leu Gly Asp
625                 630                 635                 640

Val Leu Val Arg Leu His Asn Pro Val Leu Thr Pro Thr Val
                645                 650                 655

Gln Val Thr Trp Thr Val Asp Arg Gln Pro Gln Phe Ile Gln Gly Tyr
                660                 665                 670

Arg Val Met Tyr Arg Gln Thr Ser Gly Leu Gln Ala Thr Ser Ser Trp
            675                 680                 685

Gln Asn Leu Asp Ala Lys Val Pro Thr Glu Arg Ser Ala Val Leu Val
690                 695                 700

Asn Leu Lys Lys Gly Val Thr Tyr Glu Ile Lys Val Arg Pro Tyr Phe
705                 710                 715                 720

Asn Glu Phe Gln Gly Met Asp Ser Glu Ser Lys Thr Val Arg Thr Thr
                725                 730                 735

Glu Glu Ala Pro Ser Ala Pro Pro Gln Ser Val Thr Val Leu Thr Val
            740                 745                 750

Gly Ser Tyr Asn Ser Thr Ser Ile Ser Val Ser Trp Asp Pro Pro
        755                 760                 765

Pro Asp His Gln Asn Gly Ile Ile Gln Glu Tyr Lys Ile Trp Cys Leu
        770                 775                 780

Gly Asn Glu Thr Arg Phe His Ile Asn Lys Thr Val Asp Ala Ala Ile
785                 790                 795                 800

Arg Ser Val Ile Ile Gly Gly Leu Phe Pro Gly Ile Gln Tyr Arg Val
                805                 810                 815

Glu Val Ala Ala Ser Thr Ser Ala Gly Val Gly Val Lys Ser Glu Pro
            820                 825                 830

Gln Pro Ile Ile Ile Gly Arg Arg Asn Glu Val Val Ile Thr Glu Asn
        835                 840                 845

Asn Asn Ser Ile Thr Glu Gln Ile Thr Asp Val Lys Gln Pro Ala
        850                 855                 860

Phe Ile Ala Gly Ile Gly Gly Ala Cys Trp Val Ile Leu Met Gly Phe
865                 870                 875                 880

Ser Ile Trp Leu Tyr Trp Arg Arg Lys Lys Arg Lys Gly Leu Ser Asn
            885                 890                 895
```

```
Tyr Ala Val Thr Phe Gln Arg Gly Asp Gly Leu Met Ser Asn Gly
            900                 905                 910

Ser Arg Pro Gly Leu Leu Asn Ala Gly Asp Pro Ser Tyr Pro Trp Leu
        915                 920                 925

Ala Asp Ser Trp Pro Ala Thr Ser Leu Pro Val Asn Asn Ser Asn Ser
    930                 935                 940

Gly Pro Asn Glu Ile Gly Asn Phe Gly Arg Gly Asp Val Leu Pro Pro
945                 950                 955                 960

Val Pro Gly Gln Gly Asp Lys Thr Ala Thr Met Leu Ser Asp Gly Ala
                965                 970                 975

Ile Tyr Ser Ser Ile Asp Phe Thr Thr Lys Thr Ser Tyr Asn Ser Ser
            980                 985                 990

Ser Gln Ile Thr Gln Ala Thr Pro Tyr Ala Thr Thr Gln Ile Leu His
        995                 1000                1005

Ser Asn Ser Ile His Glu Leu Ala Val Asp Leu Pro Asp Pro Gln
        1010                1015                1020

Trp Lys Ser Ser Ile Gln Gln Lys Thr Asp Leu Met Gly Phe Gly
        1025                1030                1035

Tyr Ser Leu Pro Asp Gln Asn Lys Gly Asn Asn Gly Gly Lys Gly
        1040                1045                1050

Gly Lys Lys Lys Asn Lys Asn Ser Ser Lys Pro Gln Lys Asn
        1055                1060                1065

Asn Gly Ser Thr Trp Ala Asn Val Pro Leu Pro Pro Pro Val
        1070                1075                1080

Gln Pro Leu Pro Gly Thr Glu Leu Glu His Tyr Ala Val Glu Gln
        1085                1090                1095

Gln Glu Asn Gly Tyr Asp Ser Asp Ser Trp Cys Pro Pro Leu Pro
        1100                1105                1110

Val Gln Thr Tyr Leu His Gln Gly Leu Glu Asp Glu Leu Glu Glu
        1115                1120                1125

Asp Asp Asp Arg Val Pro Thr Pro Pro Val Arg Gly Val Ala Ser
        1130                1135                1140

Ser Pro Ala Ile Ser Phe Gly Gln Gln Ser Thr Ala Thr Leu Thr
        1145                1150                1155

Pro Ser Pro Arg Glu Glu Met Gln Pro Met Leu Gln Ala His Leu
        1160                1165                1170

Asp Glu Leu Thr Arg Ala Tyr Gln Phe Asp Ile Ala Lys Gln Thr
        1175                1180                1185

Trp His Ile Gln Ser Asn Asn Gln Pro Pro Gln Pro Pro Val Pro
        1190                1195                1200

Pro Leu Gly Tyr Val Ser Gly Ala Leu Ile Ser Asp Leu Glu Thr
        1205                1210                1215

Asp Val Ala Asp Asp Asp Ala Asp Asp Glu Glu Glu Ala Leu Glu
        1220                1225                1230

Ile Pro Arg Pro Leu Arg Ala Leu Asp Gln Thr Pro Gly Ser Ser
        1235                1240                1245

Met Asp Asn Leu Asp Ser Ser Val Thr Gly Ser Met Val Asn Gly
        1250                1255                1260

Trp Gly Ser Ala Ser Asp Glu Asp Arg Asn Phe Ser Ser His Arg
        1265                1270                1275

Ser Ser Val Gly Ser Ser Ser Asp Gly Ser Ile Phe Ala Ser Gly
        1280                1285                1290

Ser Phe Ala Gln Ala Leu Val Ala Ala Ala Asp Lys Ala Gly Phe
```

```
                 1295                1300                1305
Arg Leu Asp Gly Thr Ser Leu Thr Arg Thr Gly Lys Ala Phe Thr
    1310                1315                1320

Ser Ser Gln Arg Pro Arg Pro Thr Ser Pro Phe Ser Thr Asp Ser
    1325                1330                1335

Asn Thr Ser Ala Ala Leu Ser Gln Ser Gln Arg Pro Arg Pro Thr
    1340                1345                1350

Lys Lys His Lys Gly Gly Arg Met Asp Gln Gln Pro Ala Leu Pro
    1355                1360                1365

His Arg Arg Glu Gly Met Thr Asp Glu Glu Ala Leu Val Pro Tyr
    1370                1375                1380

Ser Lys Pro Ser Phe Pro Ser Pro Gly Gly His Ser Ser Ser Gly
    1385                1390                1395

Thr Ala Ser Ser Lys Gly Ser Thr Gly Pro Arg Lys Thr Glu Val
    1400                1405                1410

Leu Arg Ala Gly His Gln Arg Asn Ala Ser Asp Leu Leu Asp Ile
    1415                1420                1425

Gly Tyr Met Gly Ser Asn Ser Gln Gly Gln Phe Thr Gly Glu Leu
    1430                1435                1440

<210> SEQ ID NO 3
<211> LENGTH: 712
<212> TYPE: PRT
<213> ORGANISM: Human

<400> SEQUENCE: 3

Met Gln Ser Lys Val Leu Leu Ala Val Ala Leu Trp Leu Cys Val Glu
 1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
 65                 70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Val Gly Tyr Arg Ile Tyr
    210                 215                 220
```

-continued

```
Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
            245                 250                 255

Asp Phe Asn Trp Glu Tyr Pro Ser Ser Lys His Gln His Lys Lys Leu
        260                 265                 270

Val Asn Arg Asp Leu Lys Thr Gln Ser Gly Ser Glu Met Lys Lys Phe
    275                 280                 285

Leu Ser Thr Leu Thr Ile Asp Gly Val Thr Arg Ser Asp Gln Gly Leu
290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
            325                 330                 335

Glu Ser Leu Val Glu Ala Thr Val Gly Glu Arg Val Arg Ile Pro Ala
        340                 345                 350

Lys Tyr Leu Gly Tyr Pro Pro Glu Ile Lys Trp Tyr Lys Asn Gly
    355                 360                 365

Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
            405                 410                 415

Val Tyr Val Pro Pro Gln Ile Gly Glu Lys Ser Leu Ile Ser Pro Val
        420                 425                 430

Asp Ser Tyr Gln Tyr Gly Thr Thr Gln Thr Leu Thr Cys Thr Val Tyr
    435                 440                 445

Ala Ile Pro Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
        500                 505                 510

Thr Val Ser Thr Leu Val Ile Gln Ala Ala Asn Val Ser Ala Leu Tyr
    515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
            565                 570                 575

Thr Phe Glu Asn Leu Thr Trp Tyr Lys Leu Gly Pro Gln Pro Leu Pro
        580                 585                 590

Ile His Val Gly Glu Leu Pro Thr Pro Val Cys Lys Asn Leu Asp Thr
    595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
```

-continued

```
                645                 650                 655
Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Gln Ile Met Trp Phe Lys Asp Asn
        690                 695                 700

Glu Thr Leu Val Glu Asp Ser Glu
705                 710

<210> SEQ ID NO 4
<211> LENGTH: 658
<212> TYPE: PRT
<213> ORGANISM: Human

<400> SEQUENCE: 4

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300
```

```
Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
            325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
            355                 360                 365

Thr Leu Val Leu Lys Lys Glu Leu Val Ala His Leu Lys Cys Thr Ile
370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
                420                 425                 430

Ser Ser Pro Gln Arg Lys Lys Val His Cys Leu Asn Met Asp Ser Leu
            435                 440                 445

Ser Phe Gln Leu Gly Leu Tyr Leu Ser Pro His Phe Leu Gln Ala Ser
450                 455                 460

Asn Thr Ile Glu Pro Gly Gln Gln Ser Phe Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
            515                 520                 525

Arg Phe Ser Phe Leu Leu His Phe Tyr Thr Val Pro Ile Pro Lys Thr
            530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
            595                 600                 605

Ala Leu Trp Tyr Ile Tyr Ser His Thr Arg Ser Pro Ser Lys Arg Glu
            610                 615                 620

Pro Val Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                645                 650                 655

Met Ala

<210> SEQ ID NO 5
<211> LENGTH: 117
<212> TYPE: PRT
<213> ORGANISM: Human

<400> SEQUENCE: 5

Met Gly Ala Pro Thr Leu Pro Pro Ala Trp Gln Pro Phe Leu Lys Asp
1               5                   10                  15
```

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
         35                  40                  45

Glu Asn Glu Pro Asp Leu Ala Gln Trp Val Phe Cys Phe Lys Glu Leu
     50                  55                  60

Glu Gly Trp Glu Pro Asp Asp Pro Ile Glu His Lys Lys His
65                  70                  75                  80

Ser Ser Gly Cys Ala Phe Leu Ser Val Lys Gln Phe Glu Glu Leu
                85                  90                  95

Thr Leu Gly Glu Phe Leu Lys Leu Val Arg Glu Thr Leu Pro Pro Pro
            100                 105                 110

Arg Ser Phe Ile Arg
        115

<210> SEQ ID NO 6
<211> LENGTH: 652
<212> TYPE: PRT
<213> ORGANISM: Human

<400> SEQUENCE: 6

Met Ala Thr Ser Met Gly Leu Leu Leu Leu Leu Leu Leu Leu Leu Thr
1               5                   10                  15

Gln Pro Gly Ala Gly Thr Gly Ala Asp Thr Glu Ala Val Val Cys Val
            20                  25                  30

Gly Thr Ala Cys Tyr Thr Ala His Ser Gly Lys Leu Ser Ala Ala Glu
         35                  40                  45

Ala Gln Asn His Cys Asn Gln Asn Gly Gly Asn Leu Ala Thr Val Lys
     50                  55                  60

Ser Lys Glu Glu Ala Gln His Val Gln Arg Val Leu Ala Gln Leu Leu
65                  70                  75                  80

Arg Arg Glu Ala Ala Leu Thr Ala Arg Met Ser Lys Phe Trp Ile Gly
                85                  90                  95

Leu Gln Arg Glu Lys Gly Lys Cys Leu Asp Pro Ser Leu Pro Leu Lys
            100                 105                 110

Gly Phe Ser Trp Val Gly Gly Glu Asp Thr Pro Tyr Ser Asn Trp
         115                 120                 125

His Lys Glu Leu Arg Asn Ser Cys Ile Ser Lys Arg Cys Val Ser Leu
     130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190

Leu Gly Gly Pro Gly Gln Val Thr Tyr Thr Thr Pro Phe Gln Thr Thr
         195                 200                 205

Ser Ser Ser Leu Glu Ala Val Pro Phe Ala Ser Ala Ala Asn Val Ala
     210                 215                 220

Cys Gly Glu Gly Asp Lys Asp Glu Thr Gln Ser His Tyr Phe Leu Cys
225                 230                 235                 240

Lys Glu Lys Ala Pro Asp Val Phe Asp Trp Gly Ser Ser Gly Pro Leu
                245                 250                 255

Cys Val Ser Pro Lys Tyr Gly Cys Asn Phe Asn Asn Gly Gly Cys His
            260                 265                 270

```
Gln Asp Cys Phe Glu Gly Gly Asp Gly Ser Phe Leu Cys Gly Cys Arg
        275                 280                 285

Pro Gly Phe Arg Leu Leu Asp Asp Leu Val Thr Cys Ala Ser Arg Asn
    290                 295                 300

Pro Cys Ser Ser Pro Cys Arg Gly Ala Thr Cys Val Leu
305                 310                 315                 320

Pro His Gly Lys Asn Tyr Thr Cys Arg Cys Pro Gln Gly Tyr Gln Leu
                325                 330                 335

Asp Ser Ser Gln Leu Asp Cys Val Asp Val Asp Glu Cys Gln Asp Ser
            340                 345                 350

Pro Cys Ala Gln Glu Cys Val Asn Thr Pro Gly Gly Phe Arg Cys Glu
        355                 360                 365

Cys Trp Val Gly Tyr Glu Pro Gly Pro Gly Glu Gly Ala Cys Gln
    370                 375                 380

Asp Val Asp Glu Cys Ala Leu Gly Arg Ser Pro Cys Ala Gln Gly Cys
385                 390                 395                 400

Thr Asn Thr Asp Gly Ser Phe His Cys Ser Cys Glu Glu Gly Tyr Val
                405                 410                 415

Leu Ala Gly Glu Asp Gly Thr Gln Cys Gln Asp Val Asp Glu Cys Val
            420                 425                 430

Gly Pro Gly Gly Pro Leu Cys Asp Ser Leu Cys Phe Asn Thr Gln Gly
        435                 440                 445

Ser Phe His Cys Gly Cys Leu Pro Gly Trp Val Leu Ala Pro Asn Gly
    450                 455                 460

Val Ser Cys Thr Met Gly Pro Val Ser Leu Gly Pro Pro Ser Gly Pro
465                 470                 475                 480

Pro Asp Glu Glu Asp Lys Gly Glu Lys Glu Gly Ser Thr Val Pro Arg
                485                 490                 495

Ala Ala Thr Ala Ser Pro Thr Arg Gly Pro Glu Gly Thr Pro Lys Ala
            500                 505                 510

Thr Pro Thr Thr Ser Arg Pro Ser Leu Ser Ser Asp Ala Pro Ile Thr
        515                 520                 525

Ser Ala Pro Leu Lys Met Leu Ala Pro Ser Gly Ser Gly Val Trp
    530                 535                 540

Arg Glu Pro Ser Ile His His Ala Thr Ala Ala Ser Gly Pro Gln Glu
545                 550                 555                 560

Pro Ala Gly Gly Asp Ser Ser Val Ala Thr Gln Asn Asn Asp Gly Thr
                565                 570                 575

Asp Gly Gln Lys Leu Leu Leu Phe Tyr Ile Leu Gly Thr Val Val Ala
            580                 585                 590

Ile Leu Leu Leu Leu Ala Leu Ala Leu Gly Leu Leu Val Tyr Arg Lys
        595                 600                 605

Arg Arg Ala Lys Arg Glu Glu Lys Lys Glu Lys Lys Pro Gln Asn Ala
    610                 615                 620

Ala Asp Ser Tyr Ser Trp Val Pro Glu Arg Ala Glu Ser Arg Ala Met
625                 630                 635                 640

Glu Asn Gln Tyr Ser Pro Thr Pro Gly Thr Asp Cys
                645                 650

<210> SEQ ID NO 7
<211> LENGTH: 277
<212> TYPE: PRT
<213> ORGANISM: Human
```

-continued

```
<400> SEQUENCE: 7

Met Trp Pro Gly Ile Leu Val Gly Ala Arg Val Ala Ser Cys Arg
1               5                   10                  15

Tyr Pro Ala Leu Gly Pro Arg Leu Ala Ala His Phe Pro Ala Gln Arg
                20                  25                  30

Pro Pro Gln Arg Thr Leu Gln Asn Gly Leu Ala Leu Gln Arg Cys Leu
            35                  40                  45

His Ala Thr Ala Thr Arg Ala Leu Pro Leu Ile Pro Ile Val Val Glu
        50                  55                  60

Gln Thr Gly Arg Gly Glu Arg Ala Tyr Asp Ile Tyr Ser Arg Leu Leu
65                  70                  75                  80

Arg Glu Arg Ile Val Cys Val Met Gly Pro Ile Asp Asp Ser Val Ala
                85                  90                  95

Ser Leu Val Ile Ala Gln Leu Leu Phe Leu Gln Ser Glu Ser Asn Lys
                100                 105                 110

Lys Pro Ile His Met Tyr Ile Asn Ser Pro Gly Gly Val Val Thr Ala
            115                 120                 125

Gly Leu Ala Ile Tyr Asp Thr Met Gln Tyr Ile Leu Asn Pro Ile Cys
        130                 135                 140

Thr Trp Cys Val Gly Gln Ala Ala Ser Met Gly Ser Leu Leu Leu Ala
145                 150                 155                 160

Ala Gly Thr Pro Gly Met Arg His Ser Leu Pro Asn Ser Arg Ile Met
                165                 170                 175

Ile His Gln Pro Ser Gly Gly Ala Arg Gly Gln Ala Thr Asp Ile Ala
            180                 185                 190

Ile Gln Ala Glu Glu Ile Met Lys Leu Lys Gln Leu Tyr Asn Ile
        195                 200                 205

Tyr Ala Lys His Thr Lys Gln Ser Leu Gln Val Ile Glu Ser Ala Met
        210                 215                 220

Glu Arg Asp Arg Tyr Met Ser Pro Met Glu Ala Gln Glu Phe Gly Ile
225                 230                 235                 240

Leu Asp Lys Val Leu Val His Pro Pro Gln Asp Gly Glu Asp Glu Pro
                245                 250                 255

Thr Leu Val Gln Lys Glu Pro Val Glu Ala Ala Pro Ala Glu Pro
            260                 265                 270

Val Pro Ala Ser Thr
            275

<210> SEQ ID NO 8
<211> LENGTH: 285
<212> TYPE: PRT
<213> ORGANISM: Human

<400> SEQUENCE: 8

Met Ala Ala Ala Glu Ala Ala Asn Cys Ile Met Glu Val Ser Cys Gly
1               5                   10                  15

Gln Ala Glu Ser Ser Glu Lys Pro Asn Ala Glu Asp Met Thr Ser Lys
                20                  25                  30

Asp Tyr Tyr Phe Asp Ser Tyr Ala His Phe Gly Ile His Glu Glu Met
            35                  40                  45

Leu Lys Asp Glu Val Arg Thr Leu Thr Tyr Arg Asn Ser Met Phe His
        50                  55                  60

Asn Arg His Leu Phe Lys Asp Lys Val Val Leu Asp Val Gly Ser Gly
65                  70                  75                  80
```

```
Thr Gly Ile Leu Cys Met Phe Ala Ala Lys Ala Gly Ala Arg Lys Val
                85                  90                  95

Ile Gly Ile Glu Cys Ser Ser Ile Ser Asp Tyr Ala Val Lys Ile Val
            100                 105                 110

Lys Ala Asn Lys Leu Asp His Val Val Thr Ile Ile Lys Gly Lys Val
        115                 120                 125

Glu Glu Val Glu Leu Pro Val Glu Lys Val Asp Ile Ile Ser Glu
    130                 135                 140

Trp Met Gly Tyr Cys Leu Phe Tyr Glu Ser Met Leu Asn Thr Val Leu
145                 150                 155                 160

Tyr Ala Arg Asp Lys Trp Leu Glu Val Asp Ile Tyr Thr Val Lys Val
                165                 170                 175

Glu Asp Leu Thr Phe Thr Ser Pro Phe Cys Leu Gln Val Lys Arg Asn
            180                 185                 190

Asp Tyr Val His Ala Leu Val Ala Tyr Phe Asn Ile Glu Phe Thr Arg
        195                 200                 205

Cys His Lys Arg Thr Gly Phe Ser Thr Ser Pro Glu Ser Pro Tyr Thr
    210                 215                 220

His Trp Lys Gln Thr Val Phe Tyr Met Glu Asp Tyr Leu Thr Val Lys
225                 230                 235                 240

Thr Gly Glu Glu Ile Phe Gly Thr Ile Gly Met Arg Pro Asn Ala Lys
                245                 250                 255

Asn Asn Arg Asp Leu Asp Phe Thr Ile Asp Leu Asp Phe Lys Gly Gln
            260                 265                 270

Leu Cys Glu Leu Ser Cys Ser Thr Asp Tyr Arg Met Arg
        275                 280                 285

<210> SEQ ID NO 9
<211> LENGTH: 609
<212> TYPE: PRT
<213> ORGANISM: Human

<400> SEQUENCE: 9

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65              70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175
```

```
Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
            245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
        290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
            325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
        370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
            405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Ala Thr Cys Cys Gln Leu
450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
            485                 490                 495

Val Gly Gln Cys Cys Thr Ser Ser Tyr Ala Asn Arg Arg Pro Cys Phe
        500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
        530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
            565                 570                 575

Gly Leu Leu Glu Lys Cys Cys Gln Gly Gln Glu Gln Glu Val Cys Phe
            580                 585                 590
```

```
Ala Glu Glu Gly Gln Lys Leu Ile Ser Lys Thr Arg Ala Ala Leu Gly
            595                 600                 605
Val

<210> SEQ ID NO 10
<211> LENGTH: 43
<212> TYPE: PRT
<213> ORGANISM: Human

<400> SEQUENCE: 10

Met Ala Ala Arg Ala Val Phe Leu Ala Leu Ser Ala Gln Leu Leu Gln
1               5                   10                  15

Ala Arg Leu Met Lys Glu Glu Ser Pro Val Val Ser Trp Arg Leu Glu
                20                  25                  30

Pro Glu Asp Gly Thr Ala Leu Cys Phe Ile Phe
            35                  40

<210> SEQ ID NO 11
<211> LENGTH: 198
<212> TYPE: PRT
<213> ORGANISM: Human

<400> SEQUENCE: 11

Leu Val Ser Glu Val Ile Arg Phe Ile Leu Phe Lys Phe His Gln Ser
1               5                   10                  15

Ser Gly Thr Pro Ile Lys Arg Glu Asp Leu Thr Gln Ile Val Thr Lys
                20                  25                  30

Asn Tyr Arg Gln Arg Asn Leu Ala Thr His Val Ile Asn Glu Ala Lys
            35                  40                  45

Lys Lys Leu Ser Asn Val Phe Gly Tyr Asp Leu Lys Glu Leu Gln Arg
    50                  55                  60

Ala Arg Ala Ser Ser Thr Gly Gln Ser Arg Leu Pro Gln Ser Gln Ser
65                  70                  75                  80

Ser Val Asp Ser Lys Ser Tyr Val Leu Val Ser Glu Leu Pro Leu Glu
                85                  90                  95

Val Phe Lys Lys His Val Val Asp Glu Thr Thr Ser Pro Val Thr Gly
                100                 105                 110

Phe Thr Phe Val Val Leu Ala Ile Val Gln Leu Ala Gly Gly Lys Ile
            115                 120                 125

Pro Glu Glu Thr Leu Trp His His Leu Lys Arg Met Gly Leu His Glu
    130                 135                 140

Asn Asp Glu His Asn Pro Val Phe Gly Asn Asn Lys Gln Thr Leu Glu
145                 150                 155                 160

Thr Leu Val Gln Gln Arg Phe Leu Gln Lys Glu Lys Val Ser Gly Pro
                165                 170                 175

Glu Gly Ser Thr Leu Val Tyr Asp Leu Ala Glu Arg Ala Leu Asp Pro
            180                 185                 190

Gln Val Ser Glu Lys Val
        195

<210> SEQ ID NO 12
<211> LENGTH: 562
<212> TYPE: PRT
<213> ORGANISM: Human

<400> SEQUENCE: 12

Met Ser Asn Gln Tyr Gln Glu Glu Gly Cys Ser Glu Arg Pro Glu Cys
1               5                   10                  15
```

```
Lys Ser Lys Ser Pro Thr Leu Leu Ser Ser Tyr Cys Ile Asp Ser Ile
            20                  25                  30

Leu Gly Arg Arg Ser Pro Cys Lys Met Arg Leu Leu Gly Ala Ala Gln
        35                  40                  45

Ser Leu Pro Ala Pro Leu Thr Ser Arg Ala Asp Pro Glu Lys Ala Val
    50                  55                  60

Gln Gly Ser Pro Lys Ser Ser Ala Pro Phe Glu Ala Glu Leu His
65                  70                  75                  80

Leu Pro Pro Lys Leu Arg Arg Leu Tyr Gly Pro Gly Gly Arg Leu
                85                  90                  95

Leu Gln Gly Ala Ala Ala Ala Ala Ala Ala Ala Ala Ala Ala
            100                 105                 110

Ala Ala Ala Thr Ala Thr Ala Gly Pro Arg Gly Glu Ala Pro Pro
            115                 120                 125

Pro Pro Pro Thr Ala Arg Pro Gly Glu Arg Pro Asp Gly Ala Gly Ala
130                 135                 140

Ala Ala Ala Ala Ala Ala Ala Ala Ala Trp Asp Thr Leu Lys
145                 150                 155                 160

Ile Ser Gln Ala Pro Gln Val Ser Ile Ser Arg Ser Lys Ser Tyr Arg
                165                 170                 175

Glu Asn Gly Ala Pro Phe Val Pro Pro Pro Ala Leu Asp Glu Leu
            180                 185                 190

Gly Gly Pro Gly Gly Val Thr His Pro Glu Glu Arg Leu Gly Val Ala
        195                 200                 205

Gly Gly Pro Gly Ser Ala Pro Ala Ala Gly Gly Thr Gly Thr Glu
    210                 215                 220

Asp Asp Glu Glu Glu Leu Leu Glu Asp Glu Glu Asp Glu Glu
225                 230                 235                 240

Glu Glu Leu Leu Glu Asp Asp Glu Glu Glu Leu Leu Glu Asp Asp Ala
                245                 250                 255

Arg Ala Leu Leu Lys Glu Pro Arg Arg Cys Pro Val Ala Ala Thr Gly
            260                 265                 270

Ala Val Ala Ala Ala Ala Ala Val Ala Thr Glu Gly Gly Glu
        275                 280                 285

Leu Ser Pro Lys Glu Glu Leu Leu His Pro Glu Asp Ala Glu Gly
    290                 295                 300

Lys Asp Gly Glu Asp Ser Val Cys Leu Ser Ala Gly Ser Asp Ser Glu
305                 310                 315                 320

Glu Gly Leu Leu Lys Arg Lys Gln Arg Arg Tyr Arg Thr Thr Phe Thr
                325                 330                 335

Ser Tyr Gln Leu Glu Glu Leu Glu Arg Ala Phe Gln Lys Thr His Tyr
            340                 345                 350

Pro Asp Val Phe Thr Arg Glu Glu Leu Ala Met Arg Leu Asp Leu Thr
        355                 360                 365

Glu Ala Arg Val Gln Val Trp Phe Gln Asn Arg Arg Ala Lys Trp Arg
    370                 375                 380

Lys Arg Glu Lys Ala Gly Ala Gln Thr His Pro Pro Gly Leu Pro Phe
385                 390                 395                 400

Pro Gly Pro Leu Ser Ala Thr His Pro Leu Ser Pro Tyr Leu Asp Ala
                405                 410                 415

Ser Pro Phe Pro Pro His His Pro Ala Leu Asp Ser Ala Trp Thr Ala
            420                 425                 430
```

-continued

```
Ala Ala Ala Ala Ala Ala Ala Phe Pro Ser Leu Pro Pro Pro
            435                 440                 445

Gly Ser Ala Ser Leu Pro Pro Ser Gly Ala Pro Leu Gly Leu Ser Thr
450                 455                 460

Phe Leu Gly Ala Ala Val Phe Arg His Pro Ala Phe Ile Ser Pro Ala
465                 470                 475                 480

Phe Gly Arg Leu Phe Ser Thr Met Ala Pro Leu Thr Ser Ala Ser Thr
                485                 490                 495

Ala Ala Ala Leu Leu Arg Gln Pro Thr Pro Ala Val Glu Gly Ala Val
                500                 505                 510

Ala Ser Gly Ala Leu Ala Asp Pro Ala Thr Ala Ala Asp Arg Arg
            515                 520                 525

Ala Ser Ser Ile Ala Ala Leu Arg Leu Lys Ala Lys Glu His Ala Ala
530                 535                 540

Gln Leu Thr Gln Leu Asn Ile Leu Pro Gly Thr Ser Thr Gly Lys Glu
545                 550                 555                 560

Val Cys

<210> SEQ ID NO 13
<211> LENGTH: 501
<212> TYPE: PRT
<213> ORGANISM: Human

<400> SEQUENCE: 13

Met Ala Pro Asp Lys Phe Leu Ser Thr Ile Thr Ala Gly Leu Met Asn
1               5                   10                  15

Phe Thr Gly Ala Asp Ile Pro Pro Leu Ser Thr Arg Asp Gln Tyr Ala
                20                  25                  30

Thr Val Asn His His Val His Glu Ala Arg Met Glu Asn Gly Gln Arg
            35                  40                  45

Lys Gln Asp Asn Val Leu Ser Asn Val Leu Ser Gly Leu Ile Asn Met
50                  55                  60

Ala Gly Ala Ser Ile Pro Ala Met Ser Ser Arg Asp Leu Tyr Ala Thr
65                  70                  75                  80

Ile Thr His Ser Val Arg Glu Glu Lys Met Glu Ser Gly Lys Pro Gln
                85                  90                  95

Thr Asp Lys Val Ile Ser Asn Asp Ala Pro Gln Leu Gly His Met Ala
                100                 105                 110

Ala Gly Gly Ile Pro Ser Met Ser Thr Lys Asp Leu Tyr Ala Thr Val
            115                 120                 125

Thr Gln Asn Val His Glu Glu Arg Met Glu Asn Asn Gln Pro Gln Pro
130                 135                 140

Ser Tyr Asp Leu Ser Thr Val Leu Pro Gly Leu Thr Tyr Leu Thr Val
145                 150                 155                 160

Ala Gly Ile Pro Ala Met Ser Thr Arg Asp Gln Tyr Ala Thr Val Thr
                165                 170                 175

His Asn Val His Glu Glu Lys Ile Lys Asn Gly Gln Ala Ala Ser Asp
                180                 185                 190

Asn Val Phe Ser Thr Val Pro Pro Ala Phe Ile Asn Met Ala Ala Thr
            195                 200                 205

Gly Val Ser Ser Met Ser Thr Arg Asp Gln Tyr Ala Ala Val Thr His
210                 215                 220

Asn Ile Arg Glu Glu Lys Ile Asn Asn Ser Gln Pro Ala Pro Gly Asn
225                 230                 235                 240
```

```
Ile Leu Ser Thr Ala Pro Pro Trp Leu Arg His Met Ala Ala Ala Gly
                245                 250                 255

Ile Ser Ser Thr Ile Thr Arg Asp Leu Tyr Val Thr Ala Thr His Ser
            260                 265                 270

Val His Glu Glu Lys Met Thr Asn Gly Gln Gln Ala Pro Asp Asn Ser
        275                 280                 285

Leu Ser Thr Val Pro Pro Gly Cys Ile Asn Leu Ser Gly Ala Gly Ile
    290                 295                 300

Ser Cys Arg Ser Thr Arg Asp Leu Tyr Ala Thr Val Ile His Asp Ile
305                 310                 315                 320

Gln Glu Glu Glu Met Glu Asn Asp Gln Thr Pro Pro Asp Gly Phe Leu
                325                 330                 335

Ser Asn Ser Asp Ser Pro Glu Leu Ile Asn Met Thr Gly His Cys Met
            340                 345                 350

Pro Pro Asn Ala Leu Asp Ser Phe Ser His Asp Phe Thr Ser Leu Ser
        355                 360                 365

Lys Asp Glu Leu Leu Tyr Lys Pro Asp Ser Asn Glu Phe Ala Val Gly
    370                 375                 380

Thr Lys Asn Tyr Ser Val Ser Ala Gly Asp Pro Pro Val Thr Val Met
385                 390                 395                 400

Ser Leu Val Glu Thr Val Pro Asn Thr Pro Gln Ile Ser Pro Ala Met
                405                 410                 415

Ala Lys Lys Ile Asn Asp Asp Ile Lys Tyr Gln Leu Met Lys Glu Val
            420                 425                 430

Arg Arg Phe Gly Gln Asn Tyr Glu Arg Ile Phe Ile Leu Leu Glu Glu
        435                 440                 445

Val Gln Gly Ser Met Lys Val Lys Arg Gln Phe Val Glu Phe Thr Ile
    450                 455                 460

Lys Glu Ala Ala Arg Phe Lys Lys Val Val Leu Ile Gln Gln Leu Glu
465                 470                 475                 480

Lys Ala Leu Lys Glu Ile Asp Ser His Cys His Leu Arg Lys Val Lys
                485                 490                 495

His Met Arg Lys Arg
            500

<210> SEQ ID NO 14
<211> LENGTH: 636
<212> TYPE: PRT
<213> ORGANISM: Human

<400> SEQUENCE: 14

Met Ser Phe Leu Ile Lys Gly Ala Gln Lys His Gly Phe Ile Cys Gln
1               5                   10                  15

Thr His Lys Glu Leu Phe Lys Arg Cys Ile Leu Lys Ser Ser Lys Thr
                20                  25                  30

Phe Asn Gly Gln Lys Met Ile Ser Ser Gln Ala Ser Ser Pro Val Asn
            35                  40                  45

Ser Lys Asn Met Asp Ser Phe Asn Tyr Ile Ile Val Gly Ala Gly Ser
    50                  55                  60

Ala Gly Cys Val Leu Ala Asn Arg Leu Thr Glu Asn Pro His Asn Thr
65                  70                  75                  80

Val Lys Leu Leu Glu Ala Gly Pro Lys Asp Thr Val Leu Gly Ser Lys
                85                  90                  95

Gln Leu Ser Trp Lys Ile His Met Pro Ala Ala Leu Thr Tyr Asn Leu
            100                 105                 110
```

```
Cys Asp Glu Lys Tyr Asn Trp Tyr Tyr His Thr Thr Pro Gln Lys His
            115                 120                 125

Met Asp Asn Arg Ile Leu Tyr Trp Pro Arg Gly Arg Val Trp Gly Gly
130                 135                 140

Ser Ser Ser Leu Asn Ala Met Val Tyr Ile Arg Gly His Ala Glu Asp
145                 150                 155                 160

Tyr Asn Arg Trp Ser Lys Glu Gly Ala Val Gly Trp Asp Tyr Glu Phe
                165                 170                 175

Cys Leu Pro Tyr Phe Lys Lys Ala Gln Thr His Glu Leu Gly Ala Asp
            180                 185                 190

Leu Tyr Arg Gly Gly Asp Gly Pro Leu His Val Ser Arg Gly Lys Thr
        195                 200                 205

Lys Asn Pro Leu His Cys Ala Phe Leu Asp Ala Ala Gln Gln Ala Gly
210                 215                 220

Tyr Pro Phe Thr Asp Asp Met Asn Gly Phe Gln Gln Glu Gly Phe Gly
225                 230                 235                 240

Trp Met Asp Met Thr Ile Tyr Glu Asp Phe Pro Arg Ala Val Tyr His
                245                 250                 255

Thr Glu Ile Ser Tyr Ile Ile Cys Ile Gly Tyr Cys Tyr Asn Lys Asn
            260                 265                 270

Val Tyr Phe Val Gly Lys Arg Trp Asn Thr Ala Ser Ala Tyr Leu Arg
        275                 280                 285

Pro Ala Leu Ser Arg Pro Asn Leu Ser Ala Glu Val Ser Thr Leu Val
290                 295                 300

Thr Lys Val Leu Phe Glu Gly Thr Lys Ala Ile Gly Ile Glu Tyr Ile
305                 310                 315                 320

Lys Asn Gly Glu Lys Lys Val Phe Ala Ser Lys Glu Val Ile Leu
                325                 330                 335

Ser Gly Gly Ala Ile Asn Ser Pro Gln Leu Leu Met Leu Ser Gly Val
            340                 345                 350

Gly Val Gly Gln Asn Leu Gln Asp His Leu Glu Val Tyr Ile Gln Gln
        355                 360                 365

Lys Cys Thr Gln Pro Leu Thr Leu Tyr Lys Ser Gln Lys Pro Leu Gln
370                 375                 380

Met Ile Lys Ile Gly Leu Glu Trp Phe Trp Lys Ser Thr Gly Asp Gly
385                 390                 395                 400

Ala Thr Ala His Leu Glu Thr Gly Gly Phe Ile Arg Ser Arg Pro Gly
                405                 410                 415

Ile Ser His Pro Asp Ile Gln Phe His Phe Leu Pro Ser Gln Val Ile
            420                 425                 430

Asp His Gly Arg Val Ala Ser Gln Leu Glu Ala Tyr Gln Val His Ile
        435                 440                 445

Gly Pro Met Arg Ser Thr Ser Val Gly Lys Leu Lys Leu Lys Ser Ser
450                 455                 460

Asp Pro Thr Glu His Pro Ile Leu Glu Pro Asn Tyr Leu Ser Thr Glu
465                 470                 475                 480

Met Asp Val Trp Glu Phe Arg Gln Cys Val Lys Leu Ala Arg Glu Ile
                485                 490                 495

Phe Ala Gln Lys Ala Phe Glu Glu Phe Arg Gly Pro Glu Ile Gln Pro
            500                 505                 510

Gly Glu His Ile Gln Ser Asp Lys Glu Ile Asp Ala Phe Ile Arg Gln
        515                 520                 525
```

```
Lys Ser Asp Ser Ala Tyr His Pro Ser Cys Thr Cys Lys Met Gly Gln
    530                 535                 540

Asn Ser Asp Pro Met Ala Val Val Asn Pro Glu Thr Lys Val Ile Gly
545                 550                 555                 560

Thr Glu Asn Leu Arg Val Val Asp Ala Ser Ile Met Pro Ser Ile Val
                565                 570                 575

Ser Gly Asn Leu Asn Ala Pro Thr Ile Met Ile Ala Glu Lys Ala Ala
            580                 585                 590

Asp Ile Ile Leu Gly Leu Pro Leu Gln Lys Asn Val Pro Val
        595                 600                 605

Tyr Lys Pro Lys Thr Leu Glu Thr Gln His Asn Pro Asp Lys Val Ala
    610                 615                 620

Trp Gln Asn Lys Ser Ile Tyr Pro Met Leu Ile Lys
625                 630                 635

<210> SEQ ID NO 15
<211> LENGTH: 140
<212> TYPE: PRT
<213> ORGANISM: Human

<400> SEQUENCE: 15

Leu Leu Tyr Lys Pro Val Asp Arg Val Thr Arg Ser Thr Leu Val Leu
1               5                   10                  15

His Asp Leu Leu Lys His Thr Pro Ala Ser His Pro Asp His Pro Leu
            20                  25                  30

Leu Gln Asp Ala Leu Arg Ile Ser Gln Asn Phe Leu Ser Ser Ile Asn
        35                  40                  45

Glu Glu Ile Thr Pro Arg Arg Gln Ser Met Thr Val Lys Lys Gly Glu
50                  55                  60

Gly Glu Asp Arg Met Lys Ala Ser Ser Thr Arg Lys Arg Leu Leu Leu
65                  70                  75                  80

Met Glu Glu Ala Leu Gln Arg Pro Val Ala Ser Asp Phe Glu Pro Gln
                85                  90                  95

Gly Leu Ser Glu Ala Ala Arg Trp Asn Ser Lys Glu Asn Leu Leu Ala
            100                 105                 110

Gly Pro Ser Glu Asn Asp Pro Asn Leu Phe Val Ala Leu Tyr Asp Phe
        115                 120                 125

Val Ala Ser Gly Asp Asn Thr Leu Ser Ile Thr Lys
    130                 135                 140

<210> SEQ ID NO 16
<211> LENGTH: 109
<212> TYPE: PRT
<213> ORGANISM: Human

<400> SEQUENCE: 16

Met Leu Met Ala Gln Glu Ala Leu Ala Phe Leu Met Ala Gln Gly Ala
1               5                   10                  15

Met Leu Ala Ala Gln Glu Arg Arg Val Pro Arg Ala Ala Glu Val Pro
            20                  25                  30

Gly Ala Gln Gly Gln Gln Gly Pro Arg Gly Arg Glu Glu Ala Pro Arg
        35                  40                  45

Gly Val Arg Met Ala Val Pro Leu Leu Arg Arg Met Glu Gly Ala Pro
    50                  55                  60

Ala Gly Pro Gly Gly Arg Thr Ala Ala Cys Phe Ser Cys Thr Ser Arg
65                  70                  75                  80
```

```
Cys Leu Ser Arg Arg Pro Trp Lys Arg Ser Trp Ala Gly Ser Cys
                85                  90                  95

Pro Gly Met Pro His Leu Ser Pro Asp Gln Gly Arg Phe
            100                 105
```

<210> SEQ ID NO 17
<211> LENGTH: 222
<212> TYPE: PRT
<213> ORGANISM: Human

<400> SEQUENCE: 17

```
Met Phe Ser Leu Ser Thr Val Ala Phe Leu Val Leu Leu Ser Thr Ser
1               5                   10                  15

Gly His Ala Ser Met Cys Pro Asp Asn Asn Gly Met Ser Asp Glu Val
            20                  25                  30

Arg Asn Thr Phe Leu Lys Lys His Asn Ala Tyr Arg Thr Leu Val Ala
        35                  40                  45

Lys Gly Glu Ala Lys Asn Ala Lys Glu Ile Gly Gly Tyr Ala Pro Lys
    50                  55                  60

Ala Ala Arg Met Leu Lys Val Thr Tyr Asp Cys Ala Ile Glu Glu Asn
65                  70                  75                  80

Thr Met Asn Phe Ala Lys Lys Cys Val Phe Ala His Asn Ser Tyr Lys
                85                  90                  95

Asp Arg Asn Tyr Trp Gly Gln Asn Phe Tyr Met Thr Ser Ile Leu Asn
            100                 105                 110

Gln Asn Lys Thr Val Ala Ala Glu Ser Val Asp Leu Trp Phe Asp
        115                 120                 125

Glu Leu Gln Gln Asn Gly Val Pro Val Asp Asn Val Met Thr Met Ala
130                 135                 140

Val Phe Asn Arg Gly Val Gly His Tyr Thr Gln Val Val Trp Gln Trp
145                 150                 155                 160

Ser Asn Lys Ile Gly Cys Ala Val Glu Trp Cys Ser Asp Met Thr Phe
                165                 170                 175

Val Ala Cys Glu Tyr Asp Ser Ala Gly Asn Tyr Met Gly Met Pro Ile
            180                 185                 190

Tyr Glu Val Gly Asn Pro Cys Thr Asn Asn Glu Asp Cys Lys Cys Thr
        195                 200                 205

Asn Cys Val Cys Ser Arg Glu Glu Ala Leu Cys Ile Ala Pro
    210                 215                 220
```

<210> SEQ ID NO 18
<211> LENGTH: 702
<212> TYPE: PRT
<213> ORGANISM: Human

<400> SEQUENCE: 18

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80
```

-continued

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro

```
                500             505             510
Val Glu Asp Lys Asp Ala Val Ala Phe Thr Cys Glu Pro Glu Ala Gln
            515                 520                 525

Asn Thr Thr Tyr Leu Trp Trp Val Asn Gly Gln Ser Leu Pro Val Ser
            530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
            595                 600                 605

Ala Asn Leu Asn Leu Ser Cys His Ser Ala Ser Asn Pro Ser Pro Gln
            610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
            675                 680                 685

Val Gly Ile Met Ile Gly Val Leu Val Gly Val Ala Leu Ile
            690                 695                 700

<210> SEQ ID NO 19
<211> LENGTH: 278
<212> TYPE: PRT
<213> ORGANISM: Human

<400> SEQUENCE: 19

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
            115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175
```

```
Asp Tyr Glu Glu Phe Ser Lys Gly Glu Leu Cys Gly Val Met Thr
                180             185                 190
Ile Ser Asp Ser Pro Arg Glu Gln Asp Ser Glu Ser Gln Thr Leu Asp
        195                 200                 205
Lys Val Tyr Gln Met Lys Ser Lys Pro Arg Gly Tyr Cys Leu Ile Ile
        210                 215                 220
Asn Asn His Asn Phe Ala Lys Ala Arg Glu Lys Val Pro Lys Leu His
225                 230                 235                 240
Ser Ile Arg Asp Arg Asn Gly Thr His Leu Asp Ala Gly Ser His Ser
                245                 250                 255
Val Ala Gln Ala Gly Val Gln Trp Cys Asp Leu Gly Ser Leu Gln Pro
                260                 265                 270
Pro Pro Pro Trp Phe Gly
            275

<210> SEQ ID NO 20
<211> LENGTH: 303
<212> TYPE: PRT
<213> ORGANISM: Human

<400> SEQUENCE: 20

Met Ala Thr Ser Arg Tyr Glu Pro Val Ala Glu Ile Gly Val Gly Ala
1               5                   10                  15
Tyr Gly Thr Val Tyr Lys Ala Arg Asp Pro His Ser Gly His Phe Val
                20                  25                  30
Ala Leu Lys Ser Val Arg Val Pro Asn Gly Gly Gly Gly Gly Gly Gly
            35                  40                  45
Leu Pro Ile Asn Thr Val Arg Glu Val Ala Leu Leu Arg Arg Leu Glu
50                  55                  60
Ala Phe Glu His Pro Asn Val Val Arg Leu Met Asp Val Cys Ala Thr
65                  70                  75                  80
Ser Arg Thr Asp Arg Glu Ile Lys Val Thr Leu Val Phe Glu His Val
                85                  90                  95
Asp Gln Asp Leu Arg Thr Tyr Leu Asp Lys Ala Pro Pro Pro Gly Leu
            100                 105                 110
Pro Ala Glu Thr Ile Lys Asp Leu Met Arg Gln Phe Leu Arg Gly Leu
            115                 120                 125
Asp Phe Leu His Ala Asn Cys Ile Val His Arg Asp Leu Lys Pro Glu
        130                 135                 140
Asn Ile Leu Val Thr Ser Gly Gly Thr Val Lys Leu Ala Asp Phe Gly
145                 150                 155                 160
Leu Ala Arg Ile Tyr Ser Tyr Gln Met Ala Leu Thr Pro Val Val Val
                165                 170                 175
Thr Leu Trp Tyr Arg Ala Pro Glu Val Leu Leu Gln Ser Thr Tyr Ala
            180                 185                 190
Thr Pro Val Asp Met Trp Ser Val Gly Cys Ile Phe Ala Glu Met Phe
        195                 200                 205
Arg Arg Lys Pro Leu Phe Cys Gly Asn Ser Glu Ala Asp Gln Leu Gly
    210                 215                 220
Lys Ile Phe Asp Leu Ile Gly Leu Pro Pro Glu Asp Asp Trp Pro Arg
225                 230                 235                 240
Asp Val Ser Leu Pro Arg Gly Ala Phe Pro Pro Arg Gly Pro Arg Pro
                245                 250                 255
Val Gln Ser Val Val Pro Glu Met Glu Glu Ser Gly Ala Gln Leu Leu
            260                 265                 270
```

Leu Glu Met Leu Thr Phe Asn Pro His Lys Arg Ile Ser Ala Phe Arg
            275                 280                 285

Ala Leu Gln His Ser Tyr Leu His Lys Asp Glu Gly Asn Pro Glu
    290                 295                 300

<210> SEQ ID NO 21
<211> LENGTH: 823
<212> TYPE: PRT
<213> ORGANISM: Human

<400> SEQUENCE: 21

Met Thr Val Leu Gln Glu Pro Val Gln Ala Ala Ile Trp Gln Ala Leu
1               5                   10                  15

Asn His Tyr Ala Tyr Arg Asp Ala Val Phe Leu Ala Glu Arg Leu Tyr
            20                  25                  30

Ala Glu Val His Ser Glu Glu Ala Leu Phe Leu Leu Ala Thr Cys Tyr
        35                  40                  45

Tyr Arg Ser Gly Lys Ala Tyr Lys Ala Tyr Arg Leu Leu Lys Gly His
    50                  55                  60

Ser Cys Thr Thr Pro Gln Cys Lys Tyr Leu Leu Ala Lys Cys Cys Val
65                  70                  75                  80

Asp Leu Ser Lys Leu Ala Glu Gly Glu Gln Ile Leu Ser Gly Gly Val
                85                  90                  95

Phe Asn Lys Gln Lys Ser His Asp Asp Ile Val Thr Glu Phe Gly Asp
            100                 105                 110

Ser Ala Cys Phe Thr Leu Ser Leu Leu Gly His Val Tyr Cys Lys Thr
        115                 120                 125

Asp Arg Leu Ala Lys Gly Ser Glu Cys Tyr Gln Lys Ser Leu Ser Leu
    130                 135                 140

Asn Pro Phe Leu Trp Ser Pro Phe Glu Ser Leu Cys Glu Ile Gly Glu
145                 150                 155                 160

Lys Pro Asp Pro Asp Gln Thr Phe Lys Phe Thr Ser Leu Gln Asn Phe
                165                 170                 175

Ser Asn Cys Leu Pro Asn Ser Cys Thr Thr Gln Val Pro Asn His Ser
            180                 185                 190

Leu Ser His Arg Gln Pro Glu Thr Val Leu Thr Glu Thr Pro Gln Asp
        195                 200                 205

Thr Ile Glu Leu Asn Arg Leu Asn Leu Glu Ser Ser Asn Ser Lys Tyr
    210                 215                 220

Ser Leu Asn Thr Asp Ser Ser Val Ser Tyr Ile Asp Ser Ala Val Ile
225                 230                 235                 240

Ser Pro Asp Thr Val Pro Leu Gly Thr Gly Thr Ser Ile Leu Ser Lys
                245                 250                 255

Gln Val Gln Asn Lys Pro Lys Thr Gly Arg Ser Leu Leu Gly Gly Pro
            260                 265                 270

Ala Ala Leu Ser Pro Leu Thr Pro Ser Phe Gly Ile Leu Pro Leu Glu
        275                 280                 285

Thr Pro Ser Pro Gly Asp Gly Ser Tyr Leu Gln Asn Tyr Thr Asn Thr
    290                 295                 300

Pro Pro Val Ile Asp Val Pro Ser Thr Gly Ala Pro Ser Lys Lys Ser
305                 310                 315                 320

Val Ala Arg Ile Gly Gln Thr Gly Thr Lys Ser Val Phe Ser Gln Ser
                325                 330                 335

Gly Asn Ser Arg Glu Val Thr Pro Ile Leu Ala Gln Thr Gln Ser Ser

```
                    340                 345                 350
Gly Pro Gln Thr Ser Thr Thr Pro Gln Val Leu Ser Pro Thr Ile Thr
            355                 360                 365
Ser Pro Pro Asn Ala Leu Pro Arg Arg Ser Ser Arg Leu Phe Thr Ser
        370                 375                 380
Asp Ser Ser Thr Thr Lys Glu Asn Ser Lys Lys Leu Lys Met Lys Phe
385                 390                 395                 400
Pro Pro Lys Ile Pro Asn Arg Lys Thr Lys Ser Lys Thr Asn Lys Gly
                405                 410                 415
Gly Ile Thr Gln Pro Asn Ile Asn Asp Ser Leu Glu Ile Thr Lys Leu
            420                 425                 430
Asp Ser Ser Ile Ile Ser Glu Gly Lys Ile Ser Thr Ile Thr Pro Gln
        435                 440                 445
Ile Gln Ala Phe Asn Leu Gln Lys Ala Ala Gly Leu Met Ser Leu
    450                 455                 460
Leu Arg Glu Met Gly Lys Gly Tyr Leu Ala Leu Cys Ser Tyr Asn Cys
465                 470                 475                 480
Lys Glu Ala Ile Asn Ile Leu Ser His Leu Pro Ser His His Tyr Asn
                485                 490                 495
Thr Gly Trp Val Leu Cys Gln Ile Gly Arg Ala Tyr Phe Glu Leu Ser
            500                 505                 510
Glu Tyr Met Gln Ala Glu Arg Ile Phe Ser Glu Val Arg Arg Ile Glu
        515                 520                 525
Asn Tyr Arg Val Glu Gly Met Glu Ile Tyr Ser Thr Thr Leu Trp His
    530                 535                 540
Leu Gln Lys Asp Val Ala Leu Ser Val Leu Ser Lys Asp Leu Thr Asp
545                 550                 555                 560
Met Asp Lys Asn Ser Pro Glu Ala Trp Cys Ala Ala Gly Asn Cys Phe
                565                 570                 575
Ser Leu Gln Arg Glu His Asp Ile Ala Ile Lys Phe Phe Gln Arg Ala
            580                 585                 590
Ile Gln Val Asp Pro Asn Tyr Ala Tyr Ala Tyr Thr Leu Leu Gly His
        595                 600                 605
Glu Phe Val Leu Thr Glu Glu Leu Asp Lys Ala Leu Ala Cys Phe Arg
    610                 615                 620
Asn Ala Ile Arg Val Asn Pro Arg His Tyr Asn Ala Trp Tyr Gly Leu
625                 630                 635                 640
Gly Met Ile Tyr Tyr Lys Gln Glu Lys Phe Ser Leu Ala Glu Met His
                645                 650                 655
Phe Gln Lys Ala Leu Asp Ile Asn Pro Gln Ser Ser Val Leu Leu Cys
            660                 665                 670
His Ile Gly Val Val Gln His Ala Leu Lys Lys Ser Glu Lys Ala Leu
        675                 680                 685
Asp Thr Leu Asn Lys Ala Ile Val Ile Asp Pro Lys Asn Pro Leu Cys
    690                 695                 700
Lys Phe His Arg Ala Ser Val Leu Phe Arg Asn Glu Lys Tyr Lys Ser
705                 710                 715                 720
Ala Leu Gln Glu Leu Glu Glu Leu Lys Gln Ile Val Pro Lys Glu Ser
                725                 730                 735
Leu Val Tyr Phe Leu Ile Gly Lys Val Tyr Lys Lys Leu Gly Gln Thr
            740                 745                 750
His Leu Ala Leu Met Asn Phe Ser Trp Ala Met Asp Leu Asp Pro Lys
        755                 760                 765
```

```
Gly Ala Asn Asn Gln Ile Lys Glu Ala Ile Asp Lys Arg Tyr Leu Pro
            770                 775                 780

Asp Asp Glu Glu Pro Ile Thr Gln Glu Glu Gln Ile Met Gly Thr Asp
785                 790                 795                 800

Glu Ser Gln Glu Ser Ser Met Thr Asp Ala Asp Asp Thr Gln Leu His
                805                 810                 815

Ala Ala Glu Ser Asp Glu Phe
            820

<210> SEQ ID NO 22
<211> LENGTH: 382
<212> TYPE: PRT
<213> ORGANISM: Human

<400> SEQUENCE: 22

Met Gly Leu Leu Leu Pro Leu Ala Leu Cys Ile Leu Val Leu Cys Cys
1               5                   10                  15

Gly Ala Met Ser Pro Pro Gln Leu Ala Leu Asn Pro Ser Ala Leu Leu
            20                  25                  30

Ser Arg Gly Cys Asn Asp Ser Asp Val Leu Ala Val Ala Gly Phe Ala
        35                  40                  45

Leu Arg Asp Ile Asn Lys Asp Arg Lys Asp Gly Tyr Val Leu Arg Leu
50                  55                  60

Asn Arg Val Asn Asp Ala Gln Glu Tyr Arg Arg Gly Gly Leu Gly Ser
65                  70                  75                  80

Leu Phe Tyr Leu Thr Leu Asp Val Leu Glu Thr Asp Cys His Val Leu
                85                  90                  95

Arg Lys Lys Ala Trp Gln Asp Cys Gly Met Arg Ile Phe Phe Glu Ser
            100                 105                 110

Val Tyr Gly Gln Cys Lys Ala Ile Phe Tyr Met Asn Asn Pro Ser Arg
        115                 120                 125

Val Leu Tyr Leu Ala Ala Tyr Asn Cys Thr Leu Arg Pro Val Ser Lys
130                 135                 140

Lys Lys Ile Tyr Met Thr Cys Pro Asp Cys Pro Ser Ser Ile Pro Thr
145                 150                 155                 160

Asp Ser Ser Asn His Gln Val Leu Glu Ala Ala Thr Glu Ser Leu Ala
                165                 170                 175

Lys Tyr Asn Asn Glu Asn Thr Ser Lys Gln Tyr Ser Leu Phe Lys Val
            180                 185                 190

Thr Arg Ala Ser Ser Gln Trp Val Val Gly Pro Ser Tyr Phe Val Glu
        195                 200                 205

Tyr Leu Ile Lys Glu Ser Pro Cys Thr Lys Ser Gln Ala Ser Ser Cys
210                 215                 220

Ser Leu Gln Ser Ser Asp Ser Val Pro Val Gly Leu Cys Lys Gly Ser
225                 230                 235                 240

Leu Thr Arg Thr His Trp Glu Lys Phe Val Ser Val Thr Cys Asp Phe
                245                 250                 255

Phe Glu Ser Gln Ala Pro Ala Thr Gly Ser Glu Asn Ser Ala Val Asn
            260                 265                 270

Gln Lys Pro Thr Asn Leu Pro Lys Val Glu Glu Ser Gln Gln Lys Asn
        275                 280                 285

Thr Pro Pro Thr Asp Ser Pro Ser Lys Ala Gly Pro Arg Gly Pro Val
290                 295                 300

Gln Tyr Leu Pro Asp Leu Asp Asp Lys Asn Ser Gln Glu Lys Gly Pro
```

```
                    305                 310                 315                 320
Gln Glu Ala Phe Pro Val His Leu Asp Leu Thr Thr Asn Pro Gln Gly
                325                 330                 335

Glu Thr Leu Asp Ile Ser Phe Leu Phe Leu Glu Pro Met Glu Glu Lys
                340                 345                 350

Leu Val Val Leu Pro Phe Pro Lys Glu Lys Ala Arg Thr Ala Glu Cys
                355                 360                 365

Pro Gly Pro Ala Gln Asn Ala Ser Pro Leu Val Leu Pro Pro
                370                 375                 380

<210> SEQ ID NO 23
<211> LENGTH: 257
<212> TYPE: PRT
<213> ORGANISM: Human

<400> SEQUENCE: 23

Met Pro Phe Ile Ser His His Tyr Pro His Asp His Ser Cys Arg Trp
1               5                   10                  15

Val Glu Pro Phe Ile Gly Gly Ala Val Phe Leu Asn Met Phe Ala
                20                  25                  30

Gln Asn Ala Leu Leu Ala Asp Ser Asn Pro Asp Leu Ile Asn Leu Tyr
                35                  40                  45

Arg Thr Ile Gln Arg Gln Lys Thr Asn Phe Ile Asn Gln Val Gln Asn
    50                  55                  60

Leu Ala Asp Lys Thr Phe Val Glu Lys Asp Tyr Tyr Glu Met Arg Asp
65                  70                  75                  80

Arg Phe Asn Lys Thr Cys Ile Ser Gly Gln Pro Leu Gln Arg Ala Ala
                85                  90                  95

Leu Phe Tyr Ser Leu Asn Arg Leu Gly Tyr Asn Gly Met Cys Arg Tyr
                100                 105                 110

Asn Ser Glu Arg Ile Tyr Ser Val Pro Trp Gly Lys His Thr Glu Leu
                115                 120                 125

Lys Leu Asp Phe Asn Lys Ile Asp Tyr Leu Ser Phe Arg Leu Ser Gly
    130                 135                 140

Ile Glu Leu Ile Thr Ala Gly Phe Glu Glu Thr Leu Ala Ala Thr Gly
145                 150                 155                 160

Glu Gly Asp Gln Ile Tyr Cys Asp Pro Pro Tyr Asp Lys Thr Ser Lys
                165                 170                 175

Thr Ser Phe Val Ser Tyr Asp Gly Lys Pro Phe Ser Gln Ser Asp His
                180                 185                 190

Val Leu Leu Ala Asn Met Leu Val Asp Ala His Arg Lys Gly Ala Ala
                195                 200                 205

Val Ala Ile Ser Asn Ser Leu Thr Pro Phe Thr Leu Gly Leu Tyr Glu
    210                 215                 220

Glu Arg Gly Phe Val Ile His Arg Leu Ser Ala Tyr Arg Ser Val Gly
225                 230                 235                 240

Ser Lys Pro Asn Thr Arg Lys Thr Glu Thr Glu Ile Leu Ala Val Leu
                245                 250                 255

Lys

<210> SEQ ID NO 24
<211> LENGTH: 288
<212> TYPE: PRT
<213> ORGANISM: Human

<400> SEQUENCE: 24
```

Met Asn Ala Lys Lys Asn Pro Leu Val Lys Pro Phe Leu Trp Ala
1               5                   10                  15

Gly Gly Lys Arg Gln Leu Leu Pro Glu Ile Leu Lys Tyr Leu Pro Lys
            20                  25                  30

Asn Ile Gly Lys Thr Thr Tyr Phe Glu Pro Phe Leu Gly Gly Ala
        35                  40                  45

Leu Leu Phe Glu Leu Gln Pro Lys Gln Ala Ile Val Asn Asp Ser Asn
50                  55                  60

Arg Glu Leu Ile Asn Cys Tyr Arg Val Ile Lys Asp Asn Val Glu Glu
65                  70                  75                  80

Leu Ile Glu Val Leu Lys Val His Lys Ala Lys Asn Ser Lys Glu Tyr
                85                  90                  95

Phe Asp Tyr Leu Arg Glu Arg Asp Arg Leu Lys Gln Tyr Asn Lys Phe
                100                 105                 110

Ser Asp Ile Gln Lys Ala Ala Arg Ile Ile Tyr Leu Asn Lys Thr Cys
            115                 120                 125

Tyr Asn Gly Leu Phe Arg Val Asn Ser Lys Gly Gln Phe Asn Val Pro
        130                 135                 140

Phe Gly Ser Tyr Lys Asn Pro Asn Ile Leu Asp Glu Ala Val Leu Arg
145                 150                 155                 160

Gly Val Asn Asp Tyr Leu Asn Gln Lys Ser Val Thr Phe Leu Asn Ile
                165                 170                 175

Asp Phe Ala Glu Ala Val Lys Asp Ala Lys Lys Gly Asp Phe Val Tyr
            180                 185                 190

Phe Asp Pro Pro Tyr Asp Pro Val Ser Asn Thr Ala Ser Phe Thr Gly
        195                 200                 205

Tyr Asp Ile Asn Gly Phe Asn Gln Asn Glu Gln Arg Arg Leu Lys Gln
210                 215                 220

Val Val Asp Glu Leu Thr Glu Lys Gly Cys Asn Val Met Leu Ser Asn
225                 230                 235                 240

Ser Ala Thr Asp Phe Ile Leu Asp Leu Tyr Lys Asp His Lys Tyr Thr
                245                 250                 255

Ile Glu Thr Val Ser Ala Thr Arg Ser Ile Asn Ser Asn Ala Leu Lys
            260                 265                 270

Arg Gly Lys Ile Asn Glu Val Leu Val Leu Asn Tyr Val Pro Lys Leu
        275                 280                 285

<210> SEQ ID NO 25
<211> LENGTH: 395
<212> TYPE: PRT
<213> ORGANISM: Human

<400> SEQUENCE: 25

Gly Pro Gly Cys Asn Thr Lys Lys Pro Asn Leu Asp Ala Glu Leu Asp
1               5                   10                  15

Gln Leu Leu Gln Gly His Tyr Ile Lys Gly Tyr Pro Lys Gln Tyr Thr
            20                  25                  30

Tyr Phe Leu Glu Asp Gly Lys Val Lys Val Ser Arg Pro Glu Gly Val
        35                  40                  45

Lys Ile Ile Pro Pro Gln Ser Asp Arg Gln Lys Ile Val Leu Gln Ala
    50                  55                  60

His Asn Leu Ala His Thr Gly Arg Glu Ala Thr Leu Leu Lys Ile Ala
65                  70                  75                  80

Asn Leu Tyr Trp Trp Pro Asn Met Arg Lys Asp Val Val Lys Gln Leu

```
                        85                  90                  95
Gly Arg Cys Gln Gln Cys Leu Ile Thr Asn Ala Ser Asn Lys Ala Ser
            100                 105                 110

Gly Pro Ile Leu Arg Pro Asp Arg Pro Gln Lys Pro Phe Asp Lys Phe
            115                 120                 125

Phe Ile Asp Tyr Ile Gly Pro Leu Pro Pro Ser Gln Gly Tyr Leu Tyr
    130                 135                 140

Val Leu Val Val Val Asp Gly Met Thr Gly Phe Thr Trp Leu Tyr Pro
145                 150                 155                 160

Thr Lys Ala Pro Ser Thr Ser Ala Thr Val Lys Ser Leu Asn Val Leu
                165                 170                 175

Thr Ser Ile Ala Ile Pro Lys Val Ile His Ser Asp Gln Gly Ala Ala
                180                 185                 190

Phe Thr Ser Ser Thr Phe Ala Glu Trp Ala Lys Glu Arg Gly Ile His
            195                 200                 205

Leu Glu Phe Ser Thr Pro Tyr His Pro Gln Ser Ser Gly Lys Val Glu
    210                 215                 220

Arg Lys Asn Ser Asp Ile Lys Arg Leu Leu Thr Lys Leu Leu Val Gly
225                 230                 235                 240

Arg Pro Thr Lys Trp Tyr Asp Leu Leu Pro Val Val Gln Leu Ala Leu
                245                 250                 255

Asn Asn Thr Tyr Ser Pro Val Leu Lys Tyr Thr Pro His Gln Leu Leu
                260                 265                 270

Phe Gly Ile Asp Ser Asn Thr Pro Phe Ala Asn Gln Asp Thr Leu Asp
            275                 280                 285

Leu Thr Arg Glu Glu Glu Leu Ser Leu Leu Gln Glu Ile Arg Thr Ser
    290                 295                 300

Leu Tyr His Pro Ser Thr Pro Pro Ala Ser Ser Arg Ser Trp Ser Pro
305                 310                 315                 320

Val Val Gly Gln Leu Val Gln Glu Arg Val Ala Arg Pro Ala Ser Leu
                325                 330                 335

Arg Pro Arg Trp His Lys Pro Ser Thr Val Leu Lys Val Leu Asn Pro
            340                 345                 350

Arg Thr Val Val Ile Leu Asp His Leu Gly Asn Asn Arg Thr Val Ser
    355                 360                 365

Ile Asp Asn Leu Lys Pro Thr Ser His Gln Asn Gly Thr Thr Asn Asp
370                 375                 380

Thr Ala Thr Met Asp His Leu Glu Lys Asn Glu
385                 390                 395

<210> SEQ ID NO 26
<211> LENGTH: 395
<212> TYPE: PRT
<213> ORGANISM: Human

<400> SEQUENCE: 26

Gly Pro Gly Cys Asn Thr Lys Lys Pro Asn Leu Asp Ala Glu Leu Asp
1               5                   10                  15

Gln Leu Leu Gln Gly His Tyr Ile Lys Gly Tyr Pro Lys Gln Tyr Thr
            20                  25                  30

Tyr Phe Leu Glu Asp Gly Lys Val Lys Val Ser Arg Pro Glu Gly Val
        35                  40                  45

Lys Ile Ile Pro Pro Gln Ser Asp Arg Gln Lys Ile Val Leu Gln Ala
    50                  55                  60
```

```
His Asn Leu Ala His Thr Gly Arg Glu Ala Thr Leu Leu Lys Ile Ala
 65                  70                  75                  80

Asn Leu Tyr Trp Trp Pro Asn Met Arg Lys Asp Val Val Lys Gln Leu
                 85                  90                  95

Gly Arg Cys Gln Gln Cys Leu Ile Thr Asn Ala Ser Asn Lys Ala Ser
            100                 105                 110

Gly Pro Ile Leu Arg Pro Asp Arg Pro Gln Lys Pro Phe Asp Lys Phe
        115                 120                 125

Phe Ile Asp Tyr Ile Gly Pro Leu Pro Pro Ser Gln Gly Tyr Leu Tyr
130                 135                 140

Val Leu Val Val Asp Gly Met Thr Gly Phe Thr Trp Leu Tyr Pro
145                 150                 155                 160

Thr Lys Ala Pro Ser Thr Ser Ala Thr Val Lys Ser Leu Asn Val Leu
                165                 170                 175

Thr Ser Ile Ala Ile Pro Lys Val Ile His Ser Asp Gln Gly Ala Ala
            180                 185                 190

Phe Thr Ser Ser Thr Phe Ala Glu Trp Ala Lys Glu Arg Gly Ile His
        195                 200                 205

Leu Glu Phe Ser Thr Pro Tyr His Pro Gln Ser Ser Gly Lys Val Glu
210                 215                 220

Arg Lys Asn Ser Asp Ile Lys Arg Leu Leu Thr Lys Leu Leu Val Gly
225                 230                 235                 240

Arg Pro Thr Lys Trp Tyr Asp Leu Leu Pro Val Val Gln Leu Ala Leu
                245                 250                 255

Asn Asn Thr Tyr Ser Pro Val Leu Lys Tyr Thr Pro His Gln Leu Leu
            260                 265                 270

Phe Gly Ile Asp Ser Asn Thr Pro Phe Ala Asn Gln Asp Thr Leu Asp
        275                 280                 285

Leu Thr Arg Glu Glu Glu Leu Ser Leu Leu Gln Glu Ile Arg Thr Ser
290                 295                 300

Leu Tyr His Pro Ser Thr Pro Pro Ala Ser Ser Arg Ser Trp Ser Pro
305                 310                 315                 320

Val Val Gly Gln Leu Val Gln Glu Arg Val Ala Arg Pro Ala Ser Leu
                325                 330                 335

Arg Pro Arg Trp His Lys Pro Ser Thr Val Leu Lys Val Leu Asn Pro
            340                 345                 350

Arg Thr Val Val Ile Leu Asp His Leu Gly Asn Asn Arg Thr Val Ser
        355                 360                 365

Ile Asp Asn Leu Lys Pro Thr Ser His Gln Asn Gly Thr Thr Asn Asp
370                 375                 380

Thr Ala Thr Met Asp His Leu Glu Lys Asn Glu
385                 390                 395

<210> SEQ ID NO 27
<211> LENGTH: 407
<212> TYPE: PRT
<213> ORGANISM: Human

<400> SEQUENCE: 27

Met Gly Val Leu Thr Lys Ser Leu Gln Lys Glu Ser Ala Lys Thr Asn
1               5                   10                  15

Lys Arg Asp Asp Tyr Ser Ala Ala Asp Leu Met His Val Pro Thr Gly
            20                  25                  30

Phe Asp Ala Ile Asp Tyr Glu Gly Gly Thr Ile Val Glu Asp Ile Asp
        35                  40                  45
```

Gly Asp Pro Met Leu Asn Ile Gly Leu Pro Met Gly Lys Ile Ile Leu
            50                  55                  60

Cys Cys Gly Asn Ser Gln Ala Gly Lys Thr Thr Gly Ala Leu Gln Phe
 65                  70                  75                  80

Ala Asn Gly Met Ala Ser His Leu Asp Gly Asp Val Val Ile Phe Asp
                    85                  90                  95

Phe Glu Arg Gly Ile Leu Asp Pro Arg Ser Arg Ile Arg Asn Leu Cys
                100                 105                 110

Arg Leu Ser Asn Asp Glu Tyr Asp Asn Arg Phe Thr Ile Tyr Lys Asn
                115                 120                 125

Ala Gly Met Ser Val Glu Phe Phe Lys Lys Gln Ile Phe Lys Ile Val
                130                 135                 140

Glu Leu Lys Glu Lys Leu Ala Lys Ala Asp Met Val Asp Trp Tyr Met
145                 150                 155                 160

Leu Asn Gly Ala Pro Val Lys Ile Tyr Pro Pro Thr Tyr Val Leu Leu
                165                 170                 175

Asp Ser Ile Pro Ser Met Lys Pro Glu Asp Val Leu Asn Asp Ser Ser
                180                 185                 190

Leu Asp Asn Asn Met Val Phe Ser Lys Met Ala Ala Ala Asn Ser Ala
                195                 200                 205

Met Leu Thr Ser Ile Val Asn Val Leu Glu Lys Tyr Asn Ile Thr Leu
                210                 215                 220

Ile Cys Ile Asn His Ile Thr Thr Lys Ile Ile Ile Asn Ala Tyr Gly
225                 230                 235                 240

Pro Arg Lys Val Leu Leu Pro Gly Met Glu Pro Glu Glu Asn Leu Pro
                245                 250                 255

Gly Gly Asn Lys Phe Val Tyr Leu Pro Ser Tyr Val Leu Lys Phe Ala
                260                 265                 270

Ser Gly Lys Ala Leu Asn Lys Asp Lys Asp Phe Lys Val Asn Gly Arg
                275                 280                 285

Val Thr Asn Cys Thr Phe Leu Lys Ser Arg Ser Ser Phe Asn Gly Ala
                290                 295                 300

Lys Leu Pro Leu Ala Val Thr Glu Lys His Gly Phe Ser Asn Val Met
305                 310                 315                 320

Thr Asn Ile Leu Ala Met Lys Glu Glu Lys Met Leu Lys Gly Thr Gly
                325                 330                 335

Gln Gly Gly Phe Trp Phe Glu Gly His Glu Asp Met Lys Phe Lys Gln
                340                 345                 350

Ser Glu Phe Ile Lys Lys Tyr Asn Lys Asp Thr Glu Phe Gln Glu Met
                355                 360                 365

Phe Asp Glu Val Ser Ser Glu Phe Trp Gln Gly Arg Leu Glu Asp Arg
                370                 375                 380

Phe Gly Asp Glu Tyr Asp Ser Val Glu Lys Ser Lys Gly Asn Asp Phe
385                 390                 395                 400

Asp Asp Asp Asp Asp Glu
                405

<210> SEQ ID NO 28
<211> LENGTH: 661
<212> TYPE: PRT
<213> ORGANISM: Human

<400> SEQUENCE: 28

Met Asp Leu Val Leu Lys Arg Cys Leu Leu His Leu Ala Val Ile Gly

```
1               5                   10                  15
Ala Leu Leu Ala Val Gly Ala Thr Lys Val Pro Arg Asn Gln Asp Trp
                20                  25                  30
Leu Gly Val Ser Arg Gln Leu Arg Thr Lys Ala Trp Asn Arg Gln Leu
                35                  40                  45
Tyr Pro Glu Trp Thr Glu Ala Gln Arg Leu Asp Cys Trp Arg Gly Gly
                50                  55                  60
Gln Val Ser Leu Lys Val Ser Asn Asp Gly Pro Thr Leu Ile Gly Ala
65                  70                  75                  80
Asn Ala Ser Phe Ser Ile Ala Leu Asn Phe Pro Gly Ser Gln Lys Val
                85                  90                  95
Leu Pro Asp Gly Gln Val Ile Trp Val Asn Asn Thr Ile Ile Asn Gly
                100                 105                 110
Ser Gln Val Trp Gly Gln Pro Val Tyr Pro Gln Glu Thr Asp Asp
                115                 120                 125
Ala Cys Ile Phe Pro Asp Gly Gly Pro Cys Pro Ser Gly Ser Trp Ser
                130                 135                 140
Gln Lys Arg Ser Phe Val Tyr Val Trp Lys Thr Trp Gly Gln Tyr Trp
145                 150                 155                 160
Gln Val Leu Gly Gly Pro Val Ser Gly Leu Ser Ile Gly Thr Gly Arg
                165                 170                 175
Ala Met Leu Gly Thr His Thr Met Glu Val Thr Val Tyr His Arg Arg
                180                 185                 190
Gly Ser Arg Ser Tyr Val Pro Leu Ala His Ser Ser Ala Phe Thr
                195                 200                 205
Ile Thr Asp Gln Val Pro Phe Ser Val Ser Val Ser Gln Leu Arg Ala
                210                 215                 220
Leu Asp Gly Gly Asn Lys His Phe Leu Arg Asn Gln Pro Leu Thr Phe
225                 230                 235                 240
Ala Leu Gln Leu His Asp Pro Ser Gly Tyr Leu Ala Glu Ala Asp Leu
                245                 250                 255
Ser Tyr Thr Trp Asp Phe Gly Asp Ser Ser Gly Thr Leu Ile Ser Arg
                260                 265                 270
Ala Leu Val Val Thr His Thr Tyr Leu Glu Pro Gly Pro Val Thr Ala
                275                 280                 285
Gln Val Val Leu Gln Ala Ala Ile Pro Leu Thr Ser Cys Gly Ser Ser
                290                 295                 300
Pro Val Pro Gly Thr Thr Asp Gly His Arg Pro Thr Ala Glu Ala Pro
305                 310                 315                 320
Asn Thr Thr Ala Gly Gln Val Pro Thr Thr Glu Val Val Gly Thr Thr
                325                 330                 335
Pro Gly Gln Ala Pro Thr Ala Glu Pro Ser Gly Thr Thr Ser Val Gln
                340                 345                 350
Val Pro Thr Thr Glu Val Ile Ser Thr Ala Pro Val Gln Met Pro Thr
                355                 360                 365
Ala Glu Ser Thr Gly Met Thr Pro Glu Lys Val Pro Val Ser Glu Val
                370                 375                 380
Met Gly Thr Thr Leu Ala Glu Met Ser Thr Pro Glu Ala Thr Gly Met
385                 390                 395                 400
Thr Pro Ala Glu Val Ser Ile Val Val Leu Ser Gly Thr Thr Ala Ala
                405                 410                 415
Gln Val Thr Thr Thr Glu Trp Val Glu Thr Thr Ala Arg Glu Leu Pro
                420                 425                 430
```

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
        450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
            645                 650                 655

Ser Gly Gln Gln Val
            660

<210> SEQ ID NO 29
<211> LENGTH: 648
<212> TYPE: PRT
<213> ORGANISM: Human

<400> SEQUENCE: 29

Met Ser His His Gly Gly Ala Pro Lys Ala Ser Thr Trp Val Val Ala
1               5                   10                  15

Ser Arg Arg Ser Ser Thr Val Ser Arg Ala Pro Glu Arg Arg Pro Ala
            20                  25                  30

Glu Glu Leu Asn Arg Thr Gly Pro Glu Gly Tyr Ser Val Gly Arg Gly
        35                  40                  45

Gly Arg Trp Arg Gly Thr Ser Arg Pro Pro Glu Ala Val Ala Ala Gly
    50                  55                  60

His Glu Glu Leu Pro Leu Cys Phe Ala Leu Lys Ser His Phe Val Gly
65                  70                  75                  80

Ala Val Ile Gly Arg Gly Gly Ser Lys Ile Lys Asn Ile Gln Ser Thr
                85                  90                  95

Thr Asn Thr Thr Ile Gln Ile Ile Gln Glu Gln Pro Glu Ser Leu Val
            100                 105                 110

Lys Ile Phe Gly Ser Lys Ala Met Gln Thr Lys Ala Lys Ala Val Ile
        115                 120                 125

Asp Asn Phe Val Lys Lys Leu Glu Glu Asn Tyr Asn Ser Glu Cys Gly

-continued

```
            130                 135                 140
Ile Asp Thr Ala Phe Gln Pro Ser Val Gly Lys Asp Gly Ser Thr Asp
145                 150                 155                 160

Asn Asn Val Val Ala Gly Asp Arg Pro Leu Ile Asp Trp Asp Gln Ile
                165                 170                 175

Arg Glu Glu Gly Leu Lys Trp Gln Thr Lys Trp Ala Asp Leu Pro
                180                 185                 190

Pro Ile Lys Lys Asn Phe Tyr Lys Glu Ser Thr Ala Thr Ser Ala Met
            195                 200                 205

Ser Lys Val Glu Ala Asp Ser Trp Arg Lys Glu Asn Phe Asn Ile Thr
        210                 215                 220

Trp Asp Asp Leu Lys Asp Gly Glu Lys Arg Pro Ile Pro Asn Pro Thr
225                 230                 235                 240

Cys Thr Phe Asp Asp Ala Phe Gln Cys Tyr Pro Glu Val Met Glu Asn
                245                 250                 255

Ile Lys Lys Ala Gly Phe Gln Lys Pro Thr Pro Ile Gln Ser Gln Ala
                260                 265                 270

Trp Pro Ile Val Leu Gln Gly Ile Asp Leu Ile Gly Val Ala Gln Thr
            275                 280                 285

Gly Thr Gly Lys Thr Leu Cys Tyr Leu Met Pro Gly Phe Ile His Leu
        290                 295                 300

Val Leu Gln Pro Ser Leu Lys Gly Gln Arg Asn Arg Pro Gly Met Leu
305                 310                 315                 320

Val Leu Thr Pro Thr Arg Glu Leu Ala Leu Gln Val Glu Gly Glu Cys
                325                 330                 335

Cys Lys Tyr Ser Tyr Lys Gly Leu Arg Ser Val Cys Val Tyr Gly Gly
                340                 345                 350

Gly Asn Arg Asp Glu Gln Ile Glu Glu Leu Lys Lys Gly Val Asp Ile
            355                 360                 365

Ile Ile Ala Thr Pro Gly Arg Leu Asn Asp Leu Gln Met Ser Asn Phe
        370                 375                 380

Val Asn Leu Lys Asn Ile Thr Tyr Leu Val Leu Asp Glu Ala Asp Lys
385                 390                 395                 400

Met Leu Asp Met Gly Phe Glu Pro Gln Ile Met Lys Ile Leu Leu Asp
                405                 410                 415

Val Arg Pro Asp Arg Gln Thr Val Met Thr Ser Ala Thr Trp Pro His
                420                 425                 430

Ser Val His Arg Leu Ala Gln Ser Tyr Leu Lys Glu Pro Met Ile Val
            435                 440                 445

Tyr Val Gly Thr Leu Asp Leu Val Ala Val Ser Ser Val Lys Gln Asn
        450                 455                 460

Ile Ile Val Thr Thr Glu Glu Lys Trp Ser His Met Gln Thr Phe
465                 470                 475                 480

Leu Gln Ser Met Ser Ser Thr Asp Lys Val Ile Val Phe Val Ser Arg
                485                 490                 495

Lys Ala Val Ala Asp His Leu Ser Ser Asp Leu Ile Leu Gly Asn Ile
                500                 505                 510

Ser Val Glu Ser Leu His Gly Asp Arg Glu Gln Arg Asp Arg Glu Lys
            515                 520                 525

Ala Leu Glu Asn Phe Lys Thr Gly Lys Val Arg Ile Leu Ile Ala Thr
        530                 535                 540

Asp Leu Ala Ser Arg Gly Leu Asp Val His Asp Val Thr His Val Tyr
545                 550                 555                 560
```

Asn Phe Asp Phe Pro Arg Asn Ile Glu Glu Tyr Val His Arg Ile Gly
            565                 570                 575

Arg Thr Gly Arg Ala Gly Arg Thr Gly Val Ser Ile Thr Thr Leu Thr
            580                 585                 590

Arg Asn Asp Trp Arg Val Ala Ser Glu Leu Ile Asn Ile Leu Glu Arg
            595                 600                 605

Ala Asn Gln Ser Ile Pro Glu Glu Leu Val Ser Met Ala Glu Arg Phe
            610                 615                 620

Lys Ala His Gln Gln Lys Arg Glu Met Glu Arg Lys Met Glu Arg Pro
625                 630                 635                 640

Gln Gly Arg Pro Lys Lys Phe His
            645

<210> SEQ ID NO 30
<211> LENGTH: 1240
<212> TYPE: PRT
<213> ORGANISM: Human

<400> SEQUENCE: 30

Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr

```
                  275                 280                 285
Leu Ser Thr Asp Val Gly Ser Cys Thr Leu Val Cys Pro Leu His Asn
    290                 295                 300
Gln Glu Val Thr Ala Glu Asp Gly Thr Gln Arg Cys Glu Lys Cys Ser
305                 310                 315                 320
Lys Pro Cys Ala Arg Val Cys Tyr Gly Leu Gly Met Glu His Leu Arg
                325                 330                 335
Glu Val Arg Ala Val Thr Ser Ala Asn Ile Gln Glu Phe Ala Gly Cys
                340                 345                 350
Lys Lys Ile Phe Gly Ser Leu Ala Phe Leu Pro Glu Ser Phe Asp Gly
                355                 360                 365
Asp Pro Ala Ser Asn Thr Ala Pro Leu Gln Pro Glu Gln Leu Gln Val
            370                 375                 380
Phe Glu Thr Leu Glu Glu Ile Thr Gly Tyr Leu Tyr Ile Ser Ala Trp
385                 390                 395                 400
Pro Asp Ser Leu Pro Asp Leu Ser Val Phe Gln Asn Leu Gln Val Ile
                405                 410                 415
Arg Gly Arg Ile Leu His Asn Gly Ala Tyr Ser Leu Thr Leu Gln Gly
                420                 425                 430
Leu Gly Ile Ser Trp Leu Gly Leu Arg Ser Leu Arg Glu Leu Gly Ser
                435                 440                 445
Gly Leu Ala Leu Ile His His Asn Thr His Leu Cys Phe Val His Thr
            450                 455                 460
Val Pro Trp Asp Gln Leu Phe Arg Asn Pro His Gln Ala Leu Leu His
465                 470                 475                 480
Thr Ala Asn Arg Pro Glu Asp Glu Cys Val Gly Glu Gly Leu Ala Cys
                485                 490                 495
His Gln Leu Cys Ala Arg Gly His Cys Trp Gly Pro Gly Pro Thr Gln
                500                 505                 510
Cys Val Asn Cys Ser Gln Phe Leu Arg Gly Gln Glu Cys Val Glu Glu
                515                 520                 525
Cys Arg Val Leu Gln Gly Leu Pro Arg Glu Tyr Val Asn Ala Arg His
            530                 535                 540
Cys Leu Pro Cys His Pro Glu Cys Gln Pro Gln Asn Gly Ser Val Thr
545                 550                 555                 560
Cys Phe Gly Pro Glu Ala Asp Gln Cys Val Ala Cys Ala His Tyr Lys
                565                 570                 575
Asp Pro Pro Phe Cys Val Ala Arg Cys Pro Ser Gly Val Lys Pro Asp
                580                 585                 590
Leu Ser Tyr Met Pro Ile Trp Lys Phe Pro Asp Glu Glu Gly Ala Cys
                595                 600                 605
Gln Pro Cys Pro Ile Asn Cys Thr His Ser Cys Val Asp Leu Asp Asp
            610                 615                 620
Lys Gly Cys Pro Ala Glu Gln Arg Ala Ser Pro Leu Thr Ser Ile Ile
625                 630                 635                 640
Ser Ala Val Val Gly Ile Leu Leu Val Val Leu Gly Val Val Phe
                645                 650                 655
Gly Ile Leu Ile Lys Arg Arg Gln Gln Lys Ile Arg Lys Tyr Thr Met
                660                 665                 670
Arg Arg Leu Leu Gln Glu Thr Glu Leu Val Glu Pro Leu Thr Pro Ser
                675                 680                 685
Gly Ala Met Pro Asn Gln Ala Gln Met Arg Ile Leu Lys Glu Thr Glu
            690                 695                 700
```

-continued

```
Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
            725                 730                 735

Ile Lys Val Leu Arg Glu Asn Thr Ser Pro Lys Ala Asn Lys Glu Ile
        740                 745                 750

Leu Asp Glu Ala Tyr Val Met Ala Gly Val Gly Ser Pro Tyr Val Ser
            755                 760                 765

Arg Leu Leu Gly Ile Cys Leu Thr Ser Thr Val Gln Leu Val Thr Gln
770                 775                 780

Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
        835                 840                 845

Phe Gly Leu Ala Arg Leu Leu Asp Ile Asp Glu Thr Glu Tyr His Ala
850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
        915                 920                 925

Pro Pro Ile Cys Thr Ile Asp Val Tyr Met Ile Met Val Lys Cys Trp
930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly Asp Leu Val Asp Ala Glu Glu Tyr
        995                 1000                1005

Leu Val Pro Gln Gln Gly Phe Phe Cys Pro Asp Pro Ala Pro Gly
    1010                1015                1020

Ala Gly Gly Met Val His His Arg His Arg Ser Ser Ser Thr Arg
    1025                1030                1035

Ser Gly Gly Gly Asp Leu Thr Leu Gly Leu Glu Pro Ser Glu Glu
    1040                1045                1050

Glu Ala Pro Arg Ser Pro Leu Ala Pro Ser Glu Gly Ala Gly Ser
    1055                1060                1065

Asp Val Phe Asp Gly Asp Leu Gly Met Gly Ala Ala Lys Gly Leu
    1070                1075                1080

Gln Ser Leu Pro Thr His Asp Pro Ser Pro Leu Gln Arg Tyr Ser
    1085                1090                1095

Glu Asp Pro Thr Val Pro Leu Pro Ser Glu Thr Asp Gly Tyr Val
    1100                1105                1110
```

```
Ala Pro Leu Thr Cys Ser Pro Gln Pro Glu Tyr Val Asn Gln Pro
    1115                1120                1125

Asp Val Arg Pro Gln Pro Pro Ser Pro Arg Glu Gly Pro Leu Pro
    1130                1135                1140

Ala Ala Arg Pro Ala Gly Ala Thr Leu Glu Arg Pro Lys Thr Leu
    1145                1150                1155

Ser Pro Gly Lys Asn Gly Val Val Lys Asp Val Phe Ala Phe Gly
    1160                1165                1170

Gly Ala Val Glu Asn Pro Glu Tyr Leu Thr Pro Gln Gly Gly Ala
    1175                1180                1185

Ala Pro Gln Pro His Pro Pro Ala Phe Ser Pro Ala Phe Asp
    1190                1195                1200

Asn Leu Tyr Tyr Trp Asp Gln Asp Pro Pro Glu Arg Gly Ala Pro
    1205                1210                1215

Pro Ser Thr Phe Lys Gly Thr Pro Thr Ala Glu Asn Pro Glu Tyr
    1220                1225                1230

Leu Gly Leu Asp Val Pro Val
    1235                1240

<210> SEQ ID NO 31
<211> LENGTH: 44
<212> TYPE: PRT
<213> ORGANISM: Human

<400> SEQUENCE: 31

Met Asn His Pro Gly Leu Phe Leu Phe Leu Gly Leu Thr Ala Val
1               5                   10                  15

Gln Leu Leu Leu Leu Val Phe Leu Leu Phe Phe Phe Leu Val Trp Trp
                20                  25                  30

Asp Gln Phe Gly Cys Arg Cys Asp Gly Phe Ile Leu
                35                  40

<210> SEQ ID NO 32
<211> LENGTH: 580
<212> TYPE: PRT
<213> ORGANISM: Human

<400> SEQUENCE: 32

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Asp
                20                  25                  30

Ala Thr Cys His Gln Val Arg Ser Phe Phe Gln Arg Leu Gln Pro Gly
                35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
                100                 105                 110

Glu Ala Phe Glu Ile Val Val Arg His Ala Lys Asn Tyr Thr Asn Ala
                115                 120                 125

Met Phe Lys Asn Asn Tyr Pro Ser Leu Thr Pro Gln Ala Phe Glu Phe
                130                 135                 140
```

-continued

```
Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
            165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
            195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
            245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
            275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
    435                 440                 445

Glu Leu Lys Met Lys Gly Pro Glu Pro Val Val Ser Gln Ile Ile Asp
450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
            485                 490                 495

Asp Cys Gly Asp Asp Glu Asp Glu Cys Ile Gly Gly Ser Gly Asp Gly
        500                 505                 510

Met Ile Lys Val Lys Asn Gln Leu Arg Phe Leu Ala Glu Leu Ala Tyr
            515                 520                 525

Asp Leu Asp Val Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
```

```
                       565                 570                 575

Phe Leu Val His
            580

<210> SEQ ID NO 33
<211> LENGTH: 1069
<212> TYPE: PRT
<213> ORGANISM: Human

<400> SEQUENCE: 33

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Leu
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350
```

```
Ser Leu Thr Gly Ala Arg Arg Leu Val Glu Thr Ile Phe Leu Gly Ser
            355                 360                 365

Arg Pro Trp Met Pro Gly Thr Pro Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
```

```
                770               775               780
Pro Leu Arg Asp Ala Val Val Ile Glu Gln Ser Ser Ser Leu Asn Glu
785               790               795               800

Ala Ser Ser Gly Leu Phe Asp Val Phe Leu Arg Phe Met Cys His His
            805               810               815

Ala Val Arg Ile Arg Gly Lys Ser Tyr Val Gln Cys Gln Gly Ile Pro
            820               825               830

Gln Gly Ser Ile Leu Ser Thr Leu Leu Cys Ser Leu Cys Tyr Gly Asp
            835               840               845

Met Glu Asn Lys Leu Phe Ala Gly Ile Arg Arg Asp Gly Leu Leu Leu
            850               855               860

Arg Leu Val Asp Asp Phe Leu Leu Val Thr Pro His Leu Thr His Ala
865               870               875               880

Lys Thr Phe Leu Ser Tyr Ala Arg Thr Ser Ile Arg Ala Ser Leu Thr
            885               890               895

Phe Asn Arg Gly Phe Lys Ala Gly Arg Asn Met Arg Lys Leu Phe
            900               905               910

Gly Val Leu Arg Leu Lys Cys His Ser Leu Phe Leu Asp Leu Gln Val
            915               920               925

Asn Ser Leu Gln Thr Val Cys Thr Asn Ile Tyr Lys Ile Leu Leu Leu
930               935               940

Gln Ala Tyr Arg Phe His Ala Cys Val Leu Gln Leu Pro Phe His Gln
945               950               955               960

Gln Val Trp Lys Asn Pro Thr Phe Phe Leu Arg Val Ile Ser Asp Thr
            965               970               975

Ala Ser Leu Cys Tyr Ser Ile Leu Lys Ala Lys Asn Ala Gly Met Ser
            980               985               990

Leu Gly Ala Lys Gly Ala Ala Gly  Pro Leu Pro Ser Glu  Ala Val Gln
            995               1000              1005

Trp Leu  Cys His Gln Ala Phe  Leu Leu Lys Leu Thr  Arg His Arg
    1010              1015              1020

Val Thr  Tyr Val Pro Leu Leu  Gly Ser Leu Arg Thr  Ala Gln Thr
    1025              1030              1035

Gln Leu  Ser Arg Lys Leu Pro  Gly Thr Thr Leu Thr  Ala Leu Glu
    1040              1045              1050

Ala Ala  Ala Asn Pro Ala Leu  Pro Ser Asp Phe Lys  Thr Ile Leu
    1055              1060              1065

Asp

<210> SEQ ID NO 34
<211> LENGTH: 404
<212> TYPE: PRT
<213> ORGANISM: Human

<400> SEQUENCE: 34

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
```

```
                65                  70                  75                  80
        Ser Tyr Leu Ala Gly Thr Leu Gly Leu Ser Ala Asp Gln Thr Ser Gly
                         85                  90                  95

Asn Tyr Leu Asn Met Gln Asp Ser Gln Gly Val Leu Ser Ser Phe Pro
                        100                 105                 110

Ala Pro Gln Ala Val Gln Asp Asn Pro Ala Met Pro Thr Ser Ser Gly
                        115                 120                 125

Ser Glu Gly Asn Val Lys Leu Cys Ser Leu Glu Glu Ala Gln Arg Ile
                        130                 135                 140

Trp Lys Gln Lys Ser Ala Glu Ile Tyr Pro Ile Met Asp Lys Ser Ser
        145                 150                 155                 160

Arg Thr Arg Leu Ala Leu Ile Ile Cys Asn Glu Glu Phe Asp Ser Ile
                        165                 170                 175

Pro Arg Arg Thr Gly Ala Glu Val Asp Ile Thr Gly Met Thr Met Leu
                        180                 185                 190

Leu Gln Asn Leu Gly Tyr Ser Val Asp Val Lys Lys Asn Leu Thr Ala
                        195                 200                 205

Ser Asp Met Thr Thr Glu Leu Glu Ala Phe Ala His Arg Pro Glu His
                        210                 215                 220

Lys Thr Ser Asp Ser Thr Phe Leu Val Phe Met Ser His Gly Ile Arg
        225                 230                 235                 240

Glu Gly Ile Cys Gly Lys Lys His Ser Glu Gln Val Pro Asp Ile Leu
                        245                 250                 255

Gln Leu Asn Ala Ile Phe Asn Met Leu Asn Thr Lys Asn Cys Pro Ser
                        260                 265                 270

Leu Lys Asp Lys Pro Lys Val Ile Ile Ile Gln Ala Cys Arg Gly Asp
                        275                 280                 285

Ser Pro Gly Val Val Trp Phe Lys Asp Ser Val Gly Val Ser Gly Asn
                        290                 295                 300

Leu Ser Leu Pro Thr Thr Glu Glu Phe Glu Asp Asp Ala Ile Lys Lys
        305                 310                 315                 320

Ala His Ile Glu Lys Asp Phe Ile Ala Phe Cys Ser Ser Thr Pro Asp
                        325                 330                 335

Asn Val Ser Trp Arg His Pro Thr Met Gly Ser Val Phe Ile Gly Arg
                        340                 345                 350

Leu Ile Glu His Met Gln Glu Tyr Ala Cys Ser Cys Asp Val Glu Glu
                        355                 360                 365

Ile Phe Arg Lys Val Arg Phe Ser Phe Glu Gln Pro Asp Gly Arg Ala
                        370                 375                 380

Gln Met Pro Thr Thr Glu Arg Val Thr Leu Thr Arg Cys Phe Tyr Leu
        385                 390                 395                 400

Phe Pro Gly His

<210> SEQ ID NO 35
        <211> LENGTH: 118
        <212> TYPE: PRT
        <213> ORGANISM: Human

<400> SEQUENCE: 35

Met Pro Arg Glu Asp Ala His Phe Ile Tyr Gly Tyr Pro Lys Lys Gly
        1               5                   10                  15

His Gly His Ser Tyr Thr Thr Ala Glu Glu Ala Ala Gly Ile Gly Ile
                        20                  25                  30

Leu Thr Val Ile Leu Gly Val Leu Leu Leu Ile Gly Cys Trp Tyr Cys
```

```
            35                  40                  45
Arg Arg Arg Asn Gly Tyr Arg Ala Leu Met Asp Lys Ser Leu His Val
 50                  55                  60

Gly Thr Gln Cys Ala Leu Thr Arg Arg Cys Pro Gln Glu Gly Phe Asp
 65                  70                  75                  80

His Arg Asp Ser Lys Val Ser Leu Gln Glu Lys Asn Cys Glu Pro Val
                 85                  90                  95

Val Pro Asn Ala Pro Ala Tyr Glu Lys Leu Ser Ala Glu Gln Ser
            100                 105                 110

Pro Pro Pro Tyr Ser Pro
            115

<210> SEQ ID NO 36
<211> LENGTH: 1255
<212> TYPE: PRT
<213> ORGANISM: Human

<400> SEQUENCE: 36

Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
 50                  55                  60

Ser Pro Gly Ser Gly Ser Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
            275                 280                 285
```

```
Gly Ser Thr Ala Pro Pro Ala His Gly Val Thr Ser Ala Pro Asp Thr
290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
                355                 360                 365

Gly Ser Thr Ala Pro Pro Ala His Gly Val Thr Ser Ala Pro Asp Thr
370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
                435                 440                 445

Gly Ser Thr Ala Pro Pro Ala His Gly Val Thr Ser Ala Pro Asp Thr
450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
                515                 520                 525

Gly Ser Thr Ala Pro Pro Ala His Gly Val Thr Ser Ala Pro Asp Thr
530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
                595                 600                 605

Gly Ser Thr Ala Pro Pro Ala His Gly Val Thr Ser Ala Pro Asp Thr
610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
                660                 665                 670

Pro Pro Ala His Gly Val Thr Ser Ala Pro Asp Thr Arg Pro Ala Pro
                675                 680                 685

Gly Ser Thr Ala Pro Pro Ala His Gly Val Thr Ser Ala Pro Asp Thr
690                 695                 700

Arg Pro Ala Pro Gly Ser Thr Ala Pro Pro Ala His Gly Val Thr Ser
```

```
          705                 710                 715                 720
Ala Pro Asp Thr Arg Pro Ala Pro Gly Ser Thr Ala Pro Pro Ala His
                    725                 730                 735

Gly Val Thr Ser Ala Pro Asp Thr Arg Pro Ala Pro Gly Ser Thr Ala
                    740                 745                 750

Pro Pro Ala His Gly Val Thr Ser Ala Pro Asp Thr Arg Pro Ala Pro
                    755                 760                 765

Gly Ser Thr Ala Pro Pro Ala His Gly Val Thr Ser Ala Pro Asp Thr
                    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                    805                 810                 815

Gly Val Thr Ser Ala Pro Asp Thr Arg Pro Ala Pro Gly Ser Thr Ala
                    820                 825                 830

Pro Pro Ala His Gly Val Thr Ser Ala Pro Asp Thr Arg Pro Ala Pro
                    835                 840                 845

Gly Ser Thr Ala Pro Pro Ala His Gly Val Thr Ser Ala Pro Asp Thr
                    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                    885                 890                 895

Gly Val Thr Ser Ala Pro Asp Thr Arg Pro Ala Pro Gly Ser Thr Ala
                    900                 905                 910

Pro Pro Ala His Gly Val Thr Ser Ala Pro Asp Thr Arg Pro Ala Pro
                    915                 920                 925

Gly Ser Thr Ala Pro Pro Ala His Gly Val Thr Ser Ala Pro Asp Asn
                    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                    965                 970                 975

Thr Ser Ala Arg Ala Thr Thr Thr Pro Ala Ser Lys Ser Thr Pro Phe
                    980                 985                 990

Ser Ile Pro Ser His His Ser Asp Thr Pro Thr Thr Leu Ala Ser His
                    995                 1000                1005

Ser Thr Lys Thr Asp Ala Ser Ser Thr His His Ser Ser Val Pro
            1010                1015                1020

Pro Leu Thr Ser Ser Asn His Ser Thr Ser Pro Gln Leu Ser Thr
            1025                1030                1035

Gly Val Ser Phe Phe Phe Leu Ser Phe His Ile Ser Asn Leu Gln
            1040                1045                1050

Phe Asn Ser Ser Leu Glu Asp Pro Ser Thr Asp Tyr Tyr Gln Glu
            1055                1060                1065

Leu Gln Arg Asp Ile Ser Glu Met Phe Leu Gln Ile Tyr Lys Gln
            1070                1075                1080

Gly Gly Phe Leu Gly Leu Ser Asn Ile Lys Phe Arg Pro Gly Ser
            1085                1090                1095

Val Val Val Gln Leu Thr Leu Ala Phe Arg Glu Gly Thr Ile Asn
            1100                1105                1110

Val His Asp Val Glu Thr Gln Phe Asn Gln Tyr Lys Thr Glu Ala
            1115                1120                1125
```

-continued

```
Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 37
<211> LENGTH: 317
<212> TYPE: PRT
<213> ORGANISM: Human

<400> SEQUENCE: 37

Met Pro Ala Leu Gly Ser Pro Arg Arg Leu Leu Gly Ser Leu Asn Cys
1               5                   10                  15

Thr Pro Pro Ala Thr Leu Pro Leu Thr Leu Ala Pro Asn Arg Thr Gly
                20                  25                  30

Pro Gln Cys Leu Glu Val Ser Ile Pro Asp Gly Leu Phe Leu Ser Leu
            35                  40                  45

Gly Leu Val Ser Leu Val Glu Asn Val Leu Val Val Ala Ala Ile Ala
        50                  55                  60

Lys Asn Arg Asn Leu His Ser Pro Met Tyr Tyr Phe Ile Cys Cys Leu
65                  70                  75                  80

Ala Met Ser Asp Leu Leu Val Ser Val Ser Asn Val Leu Glu Thr Ala
                85                  90                  95

Val Met Leu Leu Leu Glu Ala Gly Val Leu Ala Thr Arg Ala Ala Val
            100                 105                 110

Val Gln Gln Leu Asp Asn Val Ile Asp Val Leu Ile Cys Ser Ser Met
        115                 120                 125

Val Ser Ser Leu Cys Phe Leu Gly Ala Ile Ala Val Asp Arg Tyr Ile
    130                 135                 140

Ser Ile Phe Tyr Ala Leu Arg Tyr His Ser Val Val Thr Leu Pro Arg
145                 150                 155                 160

Ala Trp Arg Ile Ile Ala Ala Ile Trp Val Ala Ser Ile Leu Thr Ser
                165                 170                 175

Val Leu Ser Ile Thr Tyr Tyr Asn His Thr Val Val Leu Leu Cys Leu
            180                 185                 190

Val Gly Phe Phe Ile Ala Met Leu Ala Leu Met Ala Val Leu Tyr Val
        195                 200                 205

His Met Leu Ala Arg Ala Cys Gln His Ala Arg Gly Ile Ala Arg Leu
    210                 215                 220

Gln Lys Arg Gln Arg Pro Ile His Gln Gly Phe Gly Leu Lys Gly Ala
```

```
                225                 230                 235                 240
Ala Thr Leu Thr Ile Leu Leu Gly Val Phe Phe Leu Cys Trp Gly Pro
                245                 250                 255
Phe Phe Leu His Leu Ser Leu Ile Val Leu Cys Pro Gln His Pro Thr
                260                 265                 270
Cys Gly Cys Ile Phe Lys Asn Phe Asn Leu Phe Leu Ala Leu Ile Ile
                275                 280                 285
Cys Asn Ala Ile Val Asp Pro Leu Ile Tyr Ala Phe Arg Ser Gln Glu
                290                 295                 300
Leu Arg Lys Thr Leu Gln Glu Val Leu Gln Cys Ser Trp
305                 310                 315

<210> SEQ ID NO 38
<211> LENGTH: 683
<212> TYPE: PRT
<213> ORGANISM: Human

<400> SEQUENCE: 38

Met Ser Ser Gly Thr Met Lys Phe Asn Gly Tyr Leu Arg Val Arg Ile
1               5                   10                  15
Gly Glu Ala Val Gly Leu Gln Pro Thr Arg Trp Ser Leu Arg His Ser
                20                  25                  30
Leu Phe Lys Lys Gly His Gln Leu Leu Asp Pro Tyr Leu Thr Val Ser
                35                  40                  45
Val Asp Gln Val Arg Val Gly Gln Thr Ser Thr Lys Gln Lys Thr Asn
            50                  55                  60
Lys Pro Thr Tyr Asn Glu Phe Cys Ala Asn Val Thr Asp Gly Gly
65                  70                  75                  80
His Leu Glu Leu Ala Val Phe His Glu Thr Pro Leu Gly Tyr Asp His
                85                  90                  95
Phe Val Ala Asn Cys Thr Leu Gln Phe Gln Glu Leu Leu Arg Thr Thr
                100                 105                 110
Gly Ala Ser Asp Thr Phe Glu Gly Trp Val Asp Leu Glu Pro Glu Gly
                115                 120                 125
Lys Val Phe Val Val Ile Thr Leu Thr Gly Ser Phe Thr Glu Ala Thr
                130                 135                 140
Leu Gln Arg Asp Arg Ile Phe Lys His Phe Thr Arg Lys Arg Gln Arg
145                 150                 155                 160
Ala Met Arg Arg Arg Val His Gln Ile Asn Gly His Lys Phe Met Ala
                165                 170                 175
Thr Tyr Leu Arg Gln Pro Thr Tyr Cys Ser His Cys Arg Glu Phe Ile
                180                 185                 190
Trp Gly Val Phe Gly Lys Gln Gly Tyr Gln Cys Gln Val Cys Thr Cys
                195                 200                 205
Val Val His Lys Arg Cys His His Leu Ile Val Thr Ala Cys Thr Cys
                210                 215                 220
Gln Asn Asn Ile Asn Lys Val Asp Ser Lys Ile Ala Glu Gln Arg Phe
225                 230                 235                 240
Gly Ile Asn Ile Pro His Lys Phe Ser Ile His Asn Tyr Lys Val Pro
                245                 250                 255
Thr Phe Cys Asp His Cys Gly Ser Leu Leu Trp Gly Ile Met Arg Gln
                260                 265                 270
Gly Leu Gln Cys Lys Ile Cys Lys Met Asn Val His Ile Arg Cys Gln
                275                 280                 285
```

```
Ala Asn Val Ala Pro Asn Cys Gly Val Asn Ala Val Glu Leu Ala Lys
            290                 295                 300

Thr Leu Ala Gly Met Gly Leu Gln Pro Gly Asn Ile Ser Pro Thr Ser
305                 310                 315                 320

Lys Leu Val Ser Arg Ser Thr Leu Arg Arg Gln Gly Lys Glu Ser Ser
                325                 330                 335

Lys Glu Gly Asn Gly Ile Gly Val Asn Ser Ser Asn Arg Leu Gly Ile
            340                 345                 350

Asp Asn Phe Glu Phe Ile Arg Val Leu Gly Lys Gly Ser Phe Gly Lys
                355                 360                 365

Val Met Leu Ala Arg Val Lys Glu Thr Gly Asp Leu Tyr Ala Val Lys
370                 375                 380

Val Leu Lys Lys Asp Val Ile Leu Gln Asp Asp Asp Val Glu Cys Thr
385                 390                 395                 400

Met Thr Glu Lys Arg Ile Leu Ser Leu Ala Arg Asn His Pro Phe Leu
                405                 410                 415

Thr Gln Leu Phe Cys Cys Phe Gln Thr Pro Asp Arg Leu Phe Phe Val
                420                 425                 430

Met Glu Phe Val Asn Gly Gly Asp Leu Met Phe His Ile Gln Lys Ser
                435                 440                 445

Arg Arg Phe Asp Glu Ala Arg Ala Arg Phe Tyr Ala Ala Glu Ile Ile
450                 455                 460

Ser Ala Leu Met Phe Leu His Asp Lys Gly Ile Ile Tyr Arg Asp Leu
465                 470                 475                 480

Lys Leu Asp Asn Val Leu Leu Asp His Glu Gly His Cys Lys Leu Ala
                485                 490                 495

Asp Phe Gly Met Cys Lys Glu Gly Ile Cys Asn Gly Val Thr Thr Ala
                500                 505                 510

Thr Phe Cys Gly Thr Pro Asp Tyr Ile Ala Pro Glu Ile Leu Gln Glu
                515                 520                 525

Met Leu Tyr Gly Pro Ala Val Asp Trp Trp Ala Met Gly Val Leu Leu
530                 535                 540

Tyr Glu Met Leu Cys Gly His Ala Pro Phe Glu Ala Glu Asn Glu Asp
545                 550                 555                 560

Asp Leu Phe Glu Ala Ile Leu Asn Asp Glu Val Val Tyr Pro Thr Trp
                565                 570                 575

Leu His Glu Asp Ala Thr Gly Ile Leu Lys Ser Phe Met Thr Lys Asn
                580                 585                 590

Pro Thr Met Arg Leu Gly Ser Leu Thr Gln Gly Gly Glu His Ala Ile
                595                 600                 605

Leu Arg His Pro Phe Phe Lys Glu Ile Asp Trp Ala Gln Leu Asn His
610                 615                 620

Arg Gln Ile Glu Pro Pro Phe Arg Pro Arg Ile Lys Ser Arg Glu Asp
625                 630                 635                 640

Val Ser Asn Phe Asp Pro Asp Phe Ile Lys Glu Glu Pro Val Leu Thr
                645                 650                 655

Pro Ile Asp Glu Gly His Leu Pro Met Ile Asn Gln Asp Glu Phe Arg
                660                 665                 670

Asn Phe Ser Tyr Val Ser Pro Glu Leu Gln Pro
                675                 680

<210> SEQ ID NO 39
<211> LENGTH: 376
<212> TYPE: PRT
```

<213> ORGANISM: Human

<400> SEQUENCE: 39

```
Met Met Ala Ser Tyr Pro Glu Pro Glu Asp Ala Ala Gly Ala Leu Leu
1               5                   10                  15

Ala Pro Glu Thr Gly Arg Thr Val Lys Glu Pro Glu Gly Pro Pro Pro
            20                  25                  30

Ser Pro Gly Lys Gly Gly Gly Gly Gly Gly Thr Ala Pro Glu Lys
        35                  40                  45

Pro Asp Pro Ala Gln Lys Pro Pro Tyr Ser Tyr Val Ala Leu Ile Ala
    50                  55                  60

Met Ala Ile Arg Glu Ser Ala Glu Lys Arg Leu Thr Leu Ser Gly Ile
65                  70                  75                  80

Tyr Gln Tyr Ile Ile Ala Lys Phe Pro Phe Tyr Glu Lys Asn Lys Lys
                85                  90                  95

Gly Trp Gln Asn Ser Ile Arg His Asn Leu Ser Leu Asn Glu Cys Phe
            100                 105                 110

Ile Lys Val Pro Arg Glu Gly Gly Glu Arg Lys Gly Asn Tyr Trp
            115                 120                 125

Thr Leu Asp Pro Ala Cys Glu Asp Met Phe Glu Lys Gly Asn Tyr Arg
    130                 135                 140

Arg Arg Arg Arg Met Lys Arg Pro Phe Arg Pro Pro Pro Ala His Phe
145                 150                 155                 160

Gln Pro Gly Lys Gly Leu Phe Gly Ala Gly Ala Ala Gly Gly Cys
                165                 170                 175

Gly Val Ala Gly Ala Gly Ala Asp Gly Tyr Gly Tyr Leu Ala Pro Pro
            180                 185                 190

Lys Tyr Leu Gln Ser Gly Phe Leu Asn Asn Ser Trp Pro Leu Pro Gln
        195                 200                 205

Pro Pro Ser Pro Met Pro Tyr Ala Ser Cys Gln Met Ala Ala Ala Ala
    210                 215                 220

Ala Ala Ala Ala Ala Ala Ala Ala Gly Pro Gly Ser Pro Gly
225                 230                 235                 240

Ala Ala Ala Val Val Lys Gly Leu Ala Gly Pro Ala Ala Ser Tyr Gly
            245                 250                 255

Pro Tyr Thr Arg Val Gln Ser Met Ala Leu Pro Pro Gly Val Val Asn
        260                 265                 270

Ser Tyr Asn Gly Leu Gly Gly Pro Pro Ala Ala Pro Pro Pro Pro Pro
    275                 280                 285

His Pro His Pro His Pro His Ala His His Leu His Ala Ala Ala Ala
290                 295                 300

Pro Pro Pro Ala Pro Pro His His Gly Ala Ala Ala Pro Pro Pro Gly
305                 310                 315                 320

Gln Leu Ser Pro Ala Ser Pro Ala Thr Ala Ala Pro Pro Ala Pro Ala
            325                 330                 335

Pro Thr Ser Ala Pro Gly Leu Gln Phe Ala Cys Ala Arg Gln Pro Glu
        340                 345                 350

Leu Ala Met Met His Cys Ser Tyr Trp Asp His Asp Ser Lys Thr Gly
            355                 360                 365

Ala Leu His Ser Arg Leu Asp Leu
        370                 375
```